US012599447B2

(12) United States Patent
Johnson et al.

(10) Patent No.: US 12,599,447 B2
(45) Date of Patent: Apr. 14, 2026

(54) SURGICAL ROBOTIC SYSTEM

(71) Applicant: GLOBUS MEDICAL, INC., Audubon, PA (US)

(72) Inventors: Norbert Johnson, North Andover, MA (US); David C. Paul, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/635,439

(22) Filed: Apr. 15, 2024

(65) Prior Publication Data

US 2025/0288376 A1      Sep. 18, 2025

Related U.S. Application Data

(63) Continuation-in-part of application No. 18/603,494, filed on Mar. 13, 2024.

(51) Int. Cl.

| | |
|---|---|
| *A61B 34/32* | (2016.01) |
| *A61B 17/70* | (2006.01) |
| *A61B 50/13* | (2016.01) |
| *A61B 90/00* | (2016.01) |
| *A61B 90/50* | (2016.01) |
| *A61B 17/56* | (2006.01) |
| *A61B 34/20* | (2016.01) |

(52) U.S. Cl.
CPC .......... *A61B 34/32* (2016.02); *A61B 17/7074* (2013.01); *A61B 50/13* (2016.02); *A61B 90/37* (2016.02); *A61B 90/50* (2016.02); *A61B 2017/564* (2013.01); *A61B 2034/2055* (2016.02)

(58) Field of Classification Search
CPC .......................... A61B 34/32; A61B 2034/304
See application file for complete search history.

(56) References Cited

U.S. PATENT DOCUMENTS

| | | | |
|---|---|---|---|
| 9,131,986 | B2 | 9/2015 | Greer et al. |
| 9,220,567 | B2 | 12/2015 | Sutherland et al. |
| 10,136,948 | B2 | 11/2018 | Jensen |
| 10,667,876 | B2 | 6/2020 | Maillet et al. |
| 11,116,589 | B2 | 9/2021 | Cohen et al. |
| 11,141,229 | B2 | 10/2021 | Sweeney et al. |
| 11,213,359 | B2 | 1/2022 | Shelton, IV et al. |
| 11,399,906 | B2 | 8/2022 | Shelton, IV et al. |
| 11,399,908 | B2 | 8/2022 | Diolaiti et al. |
| 11,413,102 | B2 | 8/2022 | Shelton, IV et al. |
| 11,419,688 | B2 | 8/2022 | Kang |
| 11,472,030 | B2 | 10/2022 | Ho et al. |
| 11,529,198 | B2 | 12/2022 | Wu |
| 11,548,140 | B2 | 1/2023 | Meglan et al. |
| 11,564,688 | B2 | 1/2023 | Swayze et al. |
| 11,583,351 | B2 | 2/2023 | Kerdok et al. |
| 11,638,999 | B2 | 5/2023 | Itkowitz et al. |

(Continued)

*Primary Examiner* — Andrew Yang

(57)          ABSTRACT

Devices, systems, and methods for a robot-assisted surgery. A surgical robotic system with integrated navigation and multiple surgical arms may assist a user with one or more surgical procedures. In addition to the multiple surgical arms, the robotic system may also have peripheral arms to position a navigation camera and surgeon displays. The robotic system is collaborative to allow for easy integration into procedural workflows, for example, to install pedicle screws, interbody implants, or other surgical devices.

19 Claims, 45 Drawing Sheets

(56) References Cited

U.S. PATENT DOCUMENTS

| | | | |
|---|---|---|---|
| 11,666,413 B2 | 6/2023 | Azizian et al. | |
| 11,684,488 B2 | 6/2023 | Roh et al. | |
| 11,691,268 B2 | 7/2023 | Hosek et al. | |
| 11,723,729 B2 | 8/2023 | Shelton, IV et al. | |
| 11,903,658 B2 | 2/2024 | Farritor et al. | |
| 2020/0281670 A1 | 9/2020 | Moskowitz et al. | |
| 2021/0186615 A1 | 6/2021 | Shmayahu et al. | |
| 2021/0375439 A1 | 12/2021 | Mckinnon et al. | |
| 2022/0031397 A1 | 2/2022 | Dace et al. | |
| 2022/0096188 A1 | 3/2022 | Ellman et al. | |
| 2022/0104878 A1 | 4/2022 | Weiss et al. | |
| 2022/0125535 A1 | 4/2022 | Janna et al. | |
| 2022/0151714 A1 | 5/2022 | Zehavi et al. | |
| 2022/0192701 A1 | 6/2022 | Junio | |
| 2022/0218428 A1 | 7/2022 | Junio | |
| 2022/0241031 A1 | 8/2022 | Junio | |
| 2022/0241032 A1 | 8/2022 | Zucker et al. | |
| 2022/0280168 A1 | 9/2022 | Turgeman et al. | |
| 2022/0346882 A1 | 11/2022 | Zehavi et al. | |
| 2022/0395342 A1 | 12/2022 | Weiss et al. | |
| 2023/0115849 A1 | 4/2023 | Zucker et al. | |
| 2023/0181263 A1 | 6/2023 | Reimer et al. | |
| 2023/0240754 A1 | 8/2023 | Rotman et al. | |
| 2023/0240774 A1 | 8/2023 | Sandelson et al. | |
| 2023/0255699 A1 | 8/2023 | Ellman et al. | |
| 2023/0293244 A1 | 9/2023 | Turgeman et al. | |
| 2023/0296121 A1 | 9/2023 | Shiels et al. | |
| 2023/0346492 A1* | 11/2023 | Keret .................... | A61B 34/77 |
| 2023/0380916 A1 | 11/2023 | Bar | |

* cited by examiner

Deployed System

Docked System

SURGICAL ROBOTIC SYSTEM

CROSS-REFERENCE TO RELATED APPLICATION

This application is a continuation-in-part of U.S. patent application Ser. No. 18/603,494 filed Mar. 13, 2024, which is incorporated by reference herein in its entirety for all purposes.

FIELD OF THE INVENTION

The present disclosure relates to medical devices, and more particularly, robotic surgical systems and related devices and methods.

BACKGROUND OF THE INVENTION

Computer-assisted technology may be used during surgery, for example, to improve accuracy, reduce surgical time, and lower potential radiation exposure. In general, navigation gives surgeons better visualization in minimally invasive procedures while surgical robotics assists with trajectory alignment and positioning of the implants. The combination of robotics and navigation enhanced computer-assisted technology as robotics automated the positioning of the navigation. In addition, a robotic arm may be used to precisely align and hold the desired trajectory for the surgeon during the procedure.

There are several limitations to current robotic navigation systems, however. For example, systems may be limited by: navigation fiddle factors, such as inaccurate registrations or poor line of sight by the robotic camera; issues with passive guidance, such as possible patient movement, inability to actively move the system during the procedure, and difficulty working with long surgical constructs; having only a single robotic arm limiting methodology to one surgical action at a time; surgeons or assistants lacking visibility of the monitor to oversee the procedure; and overall system movement being hindered intraoperatively and/or during transport.

Thus, there remains a need for improved systems and methods for robot-assisted surgeries with robotic navigation systems that act as a tool and true assistant to the surgeon throughout the surgical procedure with the flexibility and adaptability for various clinical applications and approaches.

SUMMARY OF THE INVENTION

To meet this and other needs, devices, systems, and methods for robot-assisted surgeries are provided. A surgical robotic system with integrated navigation and multiple surgical arms may assist a user with one or more surgical procedures. End effectors may be attached to each surgical arm to engage instrumentation and perform the desired surgery. In addition to the surgical arms, the robotic system may also have peripheral arms to position the navigation camera and surgeon displays. The robotic system is collaborative such that motorized sub-systems may be controlled both by the system software and manually by the user. These collaborative sub-systems may include all robotic arms, base motion, and base lock-out/stabilization. The collaborative design enables easy integration into procedural workflows, for example, to install pedicle screws, interbody implants, or other surgical devices.

According to one embodiment, a multi-arm surgical robotic system includes a moveable base station, including an on-board computer, a display electronically coupled to the computer, a camera electronically coupled to the computer and configured to detect one or more tracking markers, a pair of surgical arms electronically coupled to the computer and movable based on commands processed by the computer, and an end effector electronically coupled to each surgical arm. The surgical arms may be configured to synchronize with respect to one another. The surgical arms may be configured to perform independent surgical tasks simultaneously. The surgical arms may be configured to perform independent surgical tasks sequentially. Each of the surgical arms may be configured to be controlled by different users. One of the surgical arms may be configured to perform one type of task while the other surgical arm may be configured to perform a different type of task. One of the surgical arms may control the other surgical arm during a pantograph mode. The surgical arms may automatically perform a verification procedure.

According to one embodiment, an active fixation method of a surgical robotic system having a moveable base station, including an on-board computer, a navigation camera mounted to the base station with a camera arm, a display mounted to the base station with a display arm, and a pair of surgical arms mounted to the base station, each surgical arm having an end effector, the method including: (a) identifying a first portion of bone, attaching the end effector of a first surgical arm to a first identified location, and leaving the first surgical arm rigidly attached to the first identified location; and (b) identifying a second portion of bone, attaching the end effector of a second surgical arm to a second identified location while the first surgical arm remains rigidly attached to the first identified location, and once attached, removing the first surgical arm while leaving the second surgical arm rigidly attached to the second identified location, wherein at least one of the first and second surgical arms remain attached to bone at all times to act as a navigation source for enhanced navigation of the surgical robotic system.

The active fixation method may include one or more of the following features. The bone may include one or more vertebrae. The first identified location may be a vertebral osteophyte, and after the second surgical arm is rigidly attached to the second identified location, the osteophyte may be removed with the first surgical arm. The first identified location may be a facet, and after the second surgical arm is rigidly attached to the second identified location, the facet may be removed with the first surgical arm. The first identified location may be a lamina, and after the second surgical arm is rigidly attached to the second identified location, the lamina may be removed with the first surgical arm. The first or second identified location may be a pedicle. The method may also include sequentially performing a procedure while always leaving one surgical arm rigidly affixed to the last location, thereby enhancing navigation.

According to one embodiment, an active fixation method of a surgical robotic system having a moveable base station, including an on-board computer, a navigation camera mounted to the base station with a camera arm, a display mounted to the base station with a display arm, and a pair of surgical arms mounted to the base station, the method including: (a) guiding a first surgical arm of the surgical robotic system to a location on bone of a patient and attaching the first surgical arm to the location on the bone; (b) navigating a second surgical arm of the surgical robotic system based on the first attached surgical arm; and (c) performing a surgical task while one surgical arm remains rigidly attached to the bone to act as a fixation anchor point for the bone and for providing spatial information about a location of the bone to the surgical robotic system.

The active fixation method may include one or more of the following features. The first surgical arm may be guided to a facet, and the second surgical arm may navigate off the facet. The first surgical arm may be guided to a lamina, and the second surgical arm may navigate off the lamina. The first surgical arm may be guided to an osteophyte, and the second surgical arm may navigate off the osteophyte. The surgical task may include a decompression procedure, such as an osteotomy, laminectomy, or facetectomy.

According to one embodiment, an active fixation method of a surgical robotic system having a moveable base station, including an on-board computer, a navigation camera mounted to the base station with a camera arm, a display mounted to the base station with a display arm, and a pair of surgical arms mounted to the base station, each surgical arm having an end effector, the method including: (a) identifying an osteophyte, attaching the end effector of a first surgical arm to the osteophyte, and leaving the first surgical arm rigidly attached to the osteophyte; (b) navigating the end effector of a second surgical arm based on the first surgical arm while the first surgical arm remains rigidly attached to the osteophyte, and attaching the end effector of the second surgical arm to another location, and once attached, removing the first surgical arm while leaving the second surgical arm rigidly attached; and (c) removing the osteophyte while leaving the second surgical arm rigidly attached to bone. The end effector may include a powered end effector for cutting bone. The osteophyte may be a vertebral osteophyte. Once the second surgical arm is rigidly attached, the first surgical arm may be navigated to the osteophyte, and then the osteophyte may be removed.

Also provided are kits including implants of varying types and sizes, instruments, and other components for performing the procedures.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Figure 1:
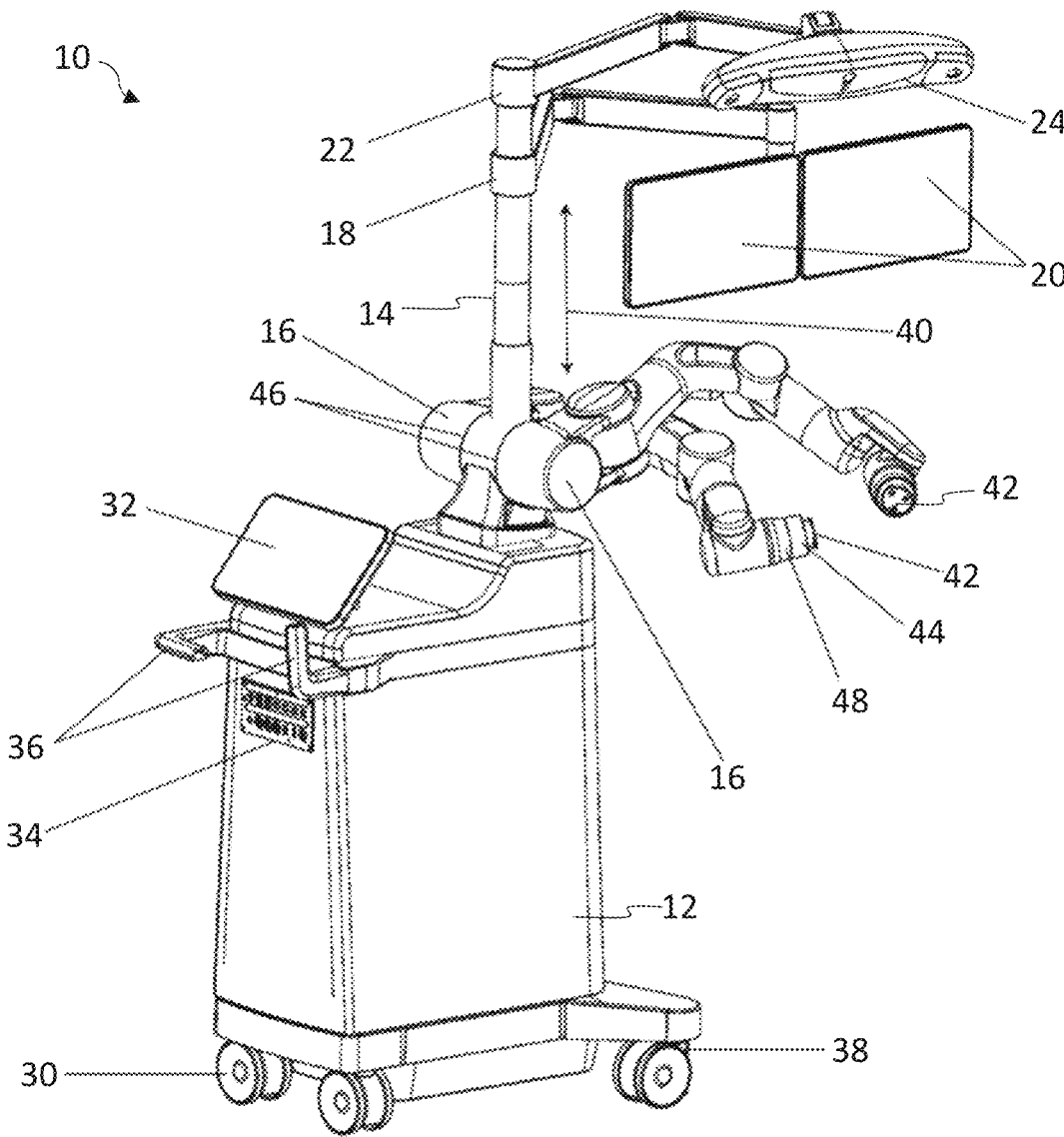
FIG. 1 illustrates a surgical robotic system having two surgical arms in accordance with one embodiment.
Figures 2A, 2B:
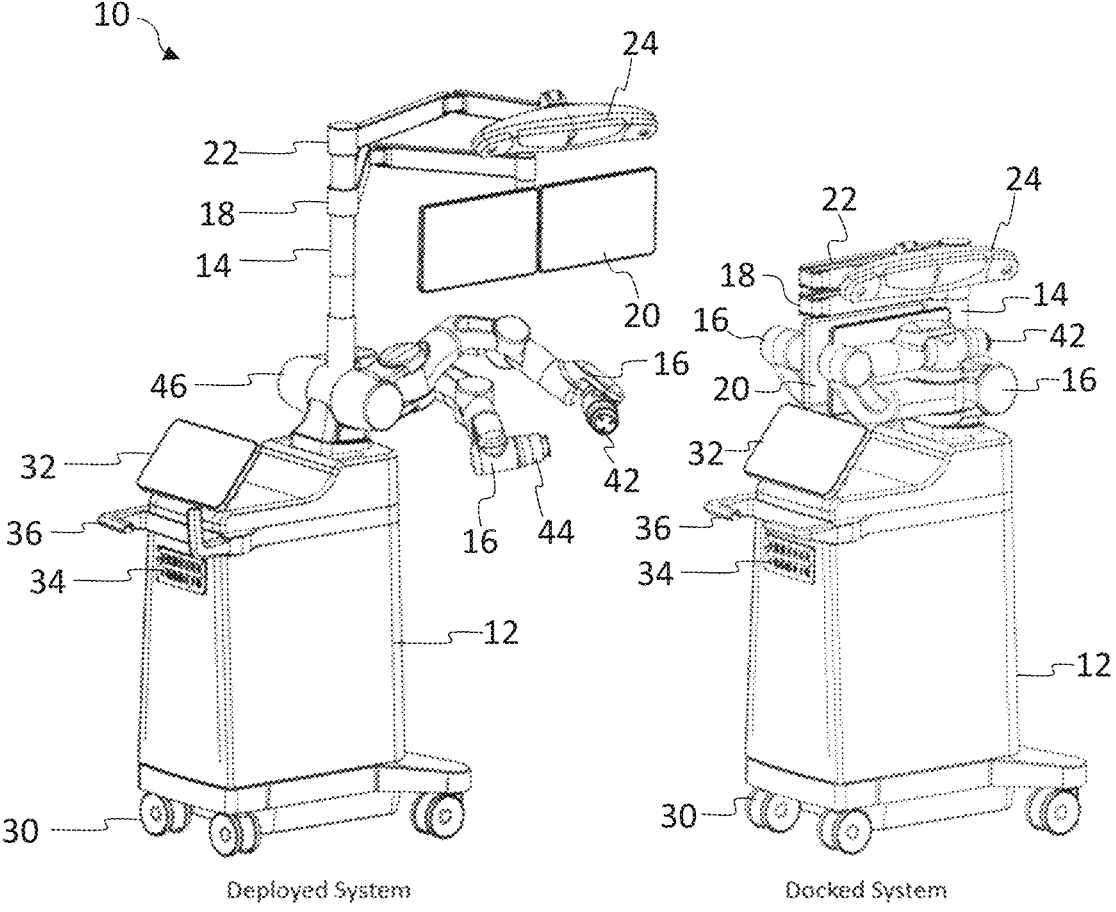
FIGS. 2A-2B show the surgical robotic system of FIG. 1 in deployed and docked system configurations, respectively.
Figures 3A, 3B:
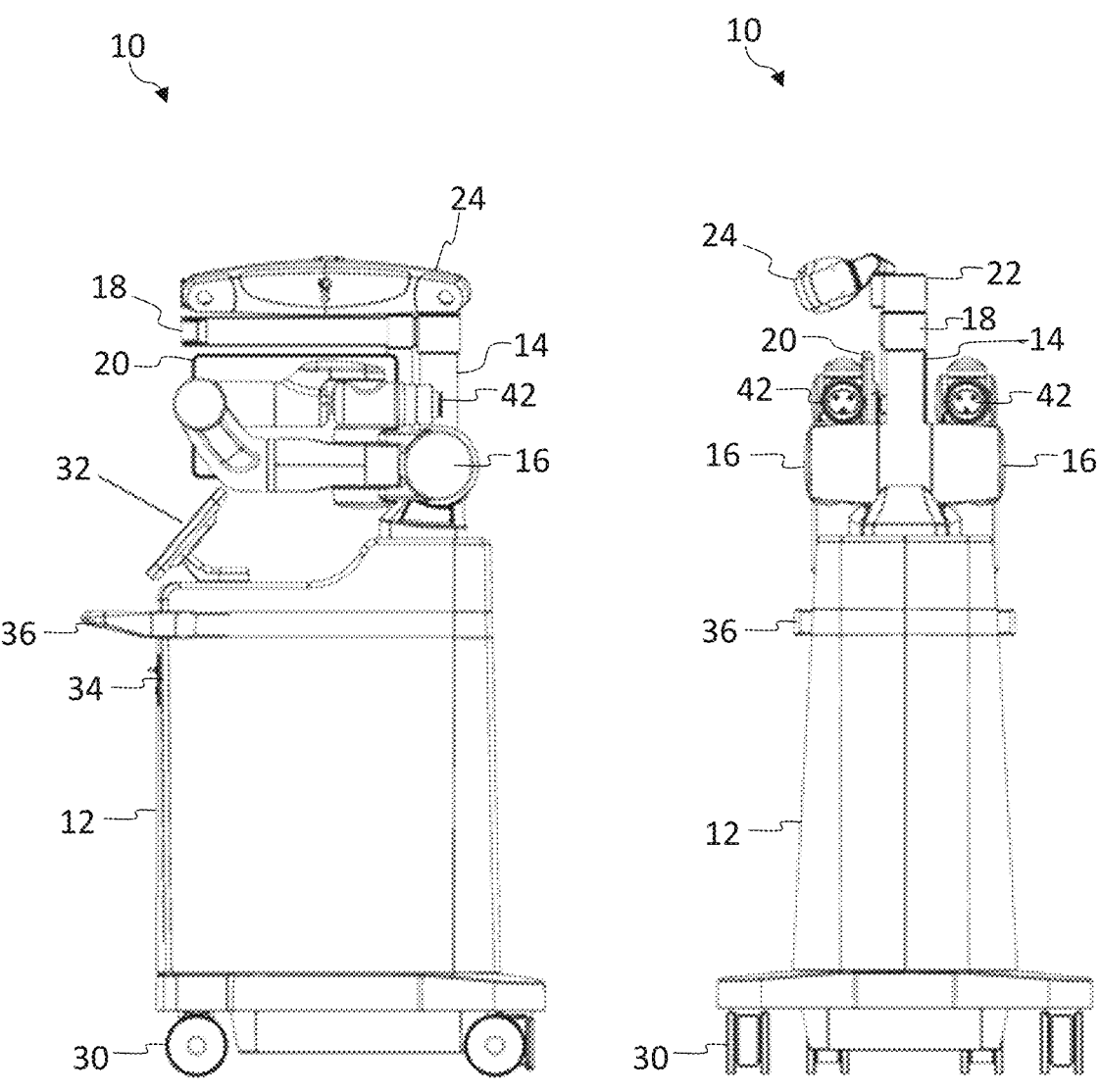
FIGS. 3A-3B show profile and front views, respectively, of the docked system according to one embodiment.

Embodiments of the disclosure are generally directed to surgical robotic systems and related devices and methods. In particular, the surgical robotic systems may include integrated real-time surgical navigation with multiple surgical arms configured to assist a user with one or more surgical tasks. End effectors may be attached to each surgical arm to guide the trajectory of specialized surgical instruments and perform the desired surgery. For example, the robotic system may include a pair of surgical arms, which guide the instruments to follow the trajectories specified by the user. A multi-arm system may provide opportunities to greatly expand the capabilities of computer-assisted technology in surgery. The multiple surgical arms allow the robotic system to assist with more surgical procedures and improve the accuracy of the procedures. The advanced multi-arm highly automated platform may allow for simultaneous interaction by one or more surgeons, technicians, and the patient.

The surgical robotic systems may be configured for full navigation and accurate alignment during spine surgery. The surgical robotic systems may allow for locating anatomical structures in open or minimally invasive surgical (MIS) procedures and navigation of surgical instruments and devices in real-time. For example, the surgical arms and attached end effectors may be used during spinal surgery to position and install pedicle screws, interbody implants, or perform or other surgical techniques. Although generally described herein with reference to performing spinal surgery, it will be appreciated that the systems and methods described herein may be applied to other orthopedic locations in the body as well as other medical procedures, such as trauma applications, cranial procedures, and oncology applications.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures may have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Multi-Arm Surgical Robotic System

Turning now to the drawing, FIG. 1 illustrates a multi-arm surgical robotic system or platform 10 in accordance with one embodiment. The multi-arm surgical robotic system 10 is configured to complete multiple surgical tasks, simultaneously or sequentially, which may improve the accuracy of the overall procedure and reduce surgical time. Surgical robotic system 10 may include, for example, a robotic base station 12, an arm positioner 14 attached to the base station 12, and multiple arms 16, 18, 22 attached to the positioner 14. Two or more surgical arms 16 may help to guide instruments or perform the surgical tasks, for example, using an end effector 26. A monitor arm 18 is configured for supporting one or more displays or monitors 20. A camera arm 22 is configured for supporting one or more navigation cameras 24, for example, for detecting and tracking markers, such as active and passive markers. Unlike other robotic systems which may utilize a separate viewing/control station or separate camera stand/station, all of the system components are integrated into a single mobile unit for robotic system 10. The integration of all components into one mobile platform may improve usability and accuracy of the system 10, while also reducing the overall footprint in the operating room.

The robotic base station 12 may include a mobile cabinet or portable frame, for example, on casters or wheels 30. The base station 12 houses an on-board computer or computing unit for controlling all functionality of the robotic system 10. The on-board computer may include a central processing unit (CPU), memory, and an input/output interface. The central processing unit carries out the instructions of a computer program or software by performing arithmetical, logical, control, and input/output (I/O) operations specified by the instructions. The memory may include volatile and non-volatile memory storage that temporarily or permanently store data and instructions that are currently in use or will be needed by the central processing unit. This may include, for example, random access memory (RAM), read-only memory (ROM), and storage devices like hard drives. The input/output interface allows the computer system to interact with the user, take in information, and deliver results, and may include devices such as a monitor, keyboard, mouse, network interface for internet connectivity, and so forth.

As shown in the embodiment of FIG. 1, the multi-arm surgical robotic system 10 may include one or more user interfaces, such as displays or monitors 20, 32 including touchscreen displays, which may be operated by one or more surgeons or other users. Before or during the medical procedure, two-dimensional (2D) and/or three-dimensional (3D) images, such as computed tomography (CT) scans, may be taken of a desired surgical area of a patient 62 and provided to the on-board computer. The surgeon may use the images to program a desired point of insertion and trajectory for one or more surgical instruments 28 to reach a desired anatomical target within or upon the body of the patient 62. The desired point of insertion and trajectory may be planned on the images, which may be displayed on monitor(s) 20, 32. The system 10 includes 2D & 3D imaging software that allows for preoperative planning, navigation, and guidance throughout the surgical procedure. Further details of surgical robotic and navigation systems can be found, for example, in U.S. Patent Publication No. 2019/0021795 and U.S. Patent Publication No. 2017/0239007, which are incorporated herein by reference in their entireties for all purposes.

In one embodiment, a pair of monitors 20 may be affixed to monitor arm 18, which is part of the sterile field. The pertinent information may be displayed and manipulated by the surgeon(s) on touchscreen monitors 20 before or during the procedure. Unlike systems with only a single monitor viewable by the surgeon, the dual monitor display may provide access to a secondary surgeon or assistant, and may allow for separate control of each of the respective surgical arms 16. The monitors 20 may be arranged side-by-side, back-to-back, or in another suitable configuration for accessibility and visibility by the user(s). The base station 12 may further include a cabinet-mounted terminal or touchscreen control display 32. The cabinet-mounted touchscreen display 32 may be accessible to a user when the system 10 is docked, during transport, or during the procedure. During the surgery, cabinet display 32 may be used for non-sterile user control or observation, for example, by an assistant. It will be appreciated that one or more of the displays 30, 32 may be supplemented or replaced with an optional wireless tablet or other suitable device.

The surgical robot system 10 may also utilize a camera 24, for example, affixed to camera arm 22. The camera arm 22 is configured to move, orient, and support the camera 30 in a desired position. The camera 24 may include any suitable camera or cameras, such as one or more infrared cameras (e.g., bifocal or stereophotogrammetric cameras), able to identify, for example, active and passive tracking markers in a given measurement volume viewable from the perspective of the camera 24. The tracking markers may be arranged in a specific array or pattern, which may help to identify the instrument, for example. In an exemplary embodiment, the camera 24 is a machine vision navigation camera configured to capture visual data from the tracking markers, which may be present on the system 10, on the instrument(s) 28, affixed to the patient, or in any other suitable locations for tracking and navigating the surgical procedure. The camera 24 may scan the given measurement volume and detect the light that comes from the markers in order to identify and determine the position of the markers in three dimensions. For example, active markers may include infrared-emitting markers that are activated by an electrical signal (e.g., infrared light emitting diodes (LEDs)), and passive markers may include fiducials, retro-reflective markers (e.g., spheres or discs) that reflect infrared light (e.g., they reflect incoming IR radiation into the direction of the incoming light), for example, emitted by illuminators on the camera 24 or other suitable device. In one embodiment, the tracking markers may include machined fiducials, reflective discs, reflective spheres, and/or active LEDs, which are visible directly or through surgical draping. The location, orientation, and position of structures having these types of markers may be provided to the on-board computer, which may be shown to the user on the display(s) 20, 32. The navigation camera 24 tracks the positions in real time and provides image(s) on the monitors 20, 32, along with the patient's images, for example, to provide guidance to the surgeon during the operation.

The base station 12 may also include a connector panel 34, which includes external connection ports for various devices, such as an equipotential terminal, a foot pedal connector, a camera connector port, an HDMI connector, an ethernet connector, dual USB 3.0 ports, and the like. It will be appreciated that any suitable hardware, software, or combinations thereof may be implemented for carrying out the operation and functionality of the robotic system 10.

The robotic base station 12 may include a motorized propulsion and positioning system to transport the robotic system 10. In this manner, one or more base wheels 30 may be powered and steerable by the user before or during the procedure. The motorized propulsion and positioning system may include two primary modalities. In a first configuration, the user is able to transport and position the robotic system 10 via one or more handles 36. Powered base motion may be controlled by force input from the user on handles 36. Force feedback may be measured at the handles 36, for example, to regulate the direction and speed of movement. In a second configuration, the user may utilize smart positioning in the operating room for position recall and reachability adjustments. Smart positioning may be achieved via encoders at the wheels 30 and relative positioning tracking with navigation camera 24. Relative tracking with camera 24 may be achieved, for example, with patient reference tracking, simultaneous localization and mapping (SLAM), and/or machine vision. The smart positioning may allow for intraoperative positioning of the system 10, for example, to account for long implant constructs or complex cases. The base station 12 may include a braking and/or stabilizer system 38, to secure the base 12. The stabilizer system 38 may be rigidly fixated to stabilize the system 10 in the operating room and lock the base 12 to the ground during surgery. Stabilization may be engaged and retracted via motor power and manually by the user. In this manner, the braking system may also be used when the system 10 is powered off to assist with transport.

The arm positioner 14 is affixed to the base station 12 and controllable via the on-board computer. In one embodiment, the arm positioner 14 may include a vertical column, which provides for telescoping movement along z-axis 40, thereby functioning as a prismatic joint. Thus, the arm positioner 14 may extend or contract in a vertical direction, thereby moving one or more arms 16, 18, 22 of the system 10. As shown in this embodiment, the surgical arms 16 may be coupled to the arm positioner 14 near the base station 12 and the monitor and camera arms 18, 22 may be located toward a distal end of the arm positioner 14. In this manner, vertical movement of the arm positioner 14 may provide for movement of the monitor(s) 20 and camera(s) 24 along z-axis 40. It will be appreciated that other suitable configurations may be used to position the respective robot arms 16, 18, 22.

One or more surgical arms 16 may be provided to perform a wide range of motions and adjustments, for example, mimicking the movements of the human arm, hand, and/or fingers and closely replicating the dexterity and precision of a skilled surgeon. In one embodiment, the surgical arms 16 include a pair of left and right surgical arms arranged about the bottom of the arm positioner 14. Each surgical arm 16 may include a plurality of arm segments or links interconnected by various types of joints, as described in more detail for FIGS. 34A-34B. Each joint may allow for specific types of movement or offer specialized motion. The joints may include rotary joints, prismatic joints, spherical joints, universal joints, cylindrical joints, planar joints, or other suitable joints that contribute to the arm's range of motion, flexibility, and reach. In the embodiment shown, the system 10 includes left and right surgical arms 16, which each allow for movement with seven degrees of freedom (7 DoF). For example, the movement may include three translational movements (along the x, y, and z axes), three rotational movements (around the x, y, and z axes), and an additional rotation or translation for imparting high precision and dexterity. It will be appreciated that the surgical arms 16 may be configured to have any suitable orientation or movement allowing each arm 16 to move forward/backward, left/right, up/down, yaw left/right, pitch tilt up/down, roll around its own axis, or otherwise translate or rotate for complex movement. The surgical arms 16 may be configured with zero backlash to ensure the movements are highly precise, accurate, and directly reflective of the surgeon's commands without any delay.

The distal end of each surgical arm 16 includes an end effector interface 42 for securing the end effector 26 to the end of the surgical arm 16. The end effector 26 is a device or tool, which attaches to the end of the robotic surgical arm 16 to interact with the surgical site. In some cases, the end effector 26 may include a guide tube to provide precise positioning of instruments 28 placed therethrough. In other cases, the end effector 26 may include an active or workable instrument, such as a retractor for retracting soft tissues, which is controlled by the system 10 or manually. The end effector 26 may be provided as a separate component, which is sterilized prior to use. The end effector interface 42 may include mechanical and/or electronic coupling of the end effector 26 to the distal end of the surgical arm 16. The end effector interface 42 includes a power and communication interface for the end effector 26. The end effector interface 42 allows for a rigid connection of the end effector 26 to the surgical arm 16 through the sterile drape.

The end effector 26 may be configured to guide or hold an integrated or separate navigated instrument 28. For example, the end effector 26 may include a tubular element or guide tube aligned along a planned trajectory. A separate navigated instrument 28 may be positioned through the guide tube and along the planned trajectory to perform a given function. For example, the navigated instruments 28 may include drills, taps, drivers or other instruments for inserting screws, for example. The navigated instruments 28 may further include dilators, disc preparation instruments (e.g., curettes, Cobb elevators, osteotomes, rasps, scrapers, etc.), trials, retractors/distractors, inserters, and other instruments for installing interbody implants, for example. It will be appreciated that any suitable instruments may be used for the designated surgical procedure.

Each surgical arm 16 may include one or more load cells 44, 46 configured to monitor and measure forces applied to the surgical arm 16. A distal load cell 44 may be provided near the free end of each surgical arm 16. For example, a 6-axis load cell 44 may be located at the end effector interface 42, which provides collaborative, ad hoc move mode when the user moves the arm 16 by directly applying force to the end of the arm 16 or end effector 26. A base load cell 46, such as a 6-axis load cell 46, may also be provided in each arm 16 near the connection to the arm positioner 14 to provide real-time feedback to the control system of the robot 10.

Each surgical arm 16 may include a ring of information (ROI) 48 for status indications. Each ring of information 48 may provide independent information about the status of each respective arm 16. For example, the ring of information 48 may provide individual colors, such as green for system ready, red for error, yellow for user action, etc., which conveys information to the user. The information ring 48 may also blink or provide other visual indicators to the user(s). The ring of information 48 may be located anywhere along each arm 16 or in another suitable location.

The monitor arm 18 is attached to the positioner 14, for example, near the top of the positioner 14. The monitor arm 18 includes a motorized arm with a plurality of arm segments interconnected by various types of joints 50. The motorized monitor arm 18 may be controlled by the system 10 and/or the user for optimal visibility of the monitor(s) 20. In one embodiment shown in FIGS. 25A-25B, the monitor arm 18 is connected to the positioner 14 at a rotary joint 52, the arm segments are interconnected by a duplex hinge joint 54, and the monitors 20 are coupled to the free end of the monitor arm 18 via two rotary joints 56, 58, respectively. As shown, the monitor arm 18 may allow for movement with four degrees of freedom (4 DoF). For example, the movement may include x, y, z, and yaw with the folding butterfly providing angle control. It will be appreciated that the monitor arm 18 may be configured to have any suitable orientation or movement allowing the arm 18 to support and position in the monitors 20 for optimal visibility.

The camera arm 22 is attached to the positioner 14, for example, at the distal-most end of the positioner 14. The camera arm 22 includes a motorized arm with a plurality of arm segments interconnected by various joints. The motorized camera arm 22 may be controlled by the system 10 and/or the user for optimal line of sight of the camera 24 throughout the procedure. In one embodiment, the camera arm 22 is connected to the positioner 14 at a rotary joint, the arm segments are interconnected by a duplex hinge joint, and the camera 24 is connected to the free end of the arm segments with a pivot or tilting joint. As shown, the camera arm 22 may allow for movement with six degree of freedom (6 DoF). For example, the movement may include x, y, z, yaw, pitch, and tilt. In one embodiment, the navigation camera 24 is mounted to arm 22 in a SCARA configuration (Selective Compliance Articulating Robot Arm) with a prismatic vertical joint for height adjustment followed by two in-plane revolute joints for x-y positioning. The camera itself may have 3-axis of orientation control (pan, tilt, roll) totaling 6-axis camera positioning. All joints may be motorized and use absolute, single-turn encoder feedback, allowing the system 10 to know camera position immediately on system power-up without the need for a homing routine. The camera arm 22 may be bimodal, active and passive, meaning it can be positioned either robotically or by manual surgeon interaction, achieving the collaborative approach for the system 10. Unlike systems which provide the camera on a separate stand, system 10 incorporates the camera 24 into a single cart solution. This may help to improve line of sight for the camera 24, which can only navigate if the camera 24 is able to see the patient reference and instrument of interest. The motorized camera arm 22 also allows for adjustment of the camera 24 during the procedure, which minimizes possible line of sight disruptions and removes the need for any manual positioning of the camera.

Turning now to FIGS. 2A-2B and 3A-3B, the multi-arm surgical robotic system 10 may have a deployed position and a docked position. In the deployed position shown in FIG. 2A, one or more of the robot's arms 16, 18, 22 are extended and positioned for active participation in a surgical procedure. In the deployed configuration, the surgical arms 16 may be arranged to provide optimal access to the surgical site, the camera arm 22 may be extended to provide optimal line of sight for the machine vision navigation camera 24, and the monitor arm 18 may be extended for optimal viewing and participation with the touchscreen monitors 20. In the docked position shown in FIG. 2B, all of the arms 16, 18, 22 are folded in such that the surgical robot 10 is in a compact configuration, for example, for transport or storage. The cabinet touchscreen display 32 remains accessible while the system 10 is docked. With further emphasis on the docked system 10 shown in FIGS. 3A-3B, all robotic arms 16, 18, 22 dock in compact form for easy transport and to enable selective deployment of individual arms 16, 18, 22. This arrangement allows for all four arms 16, 18, 22 in the system 10 to dock in a compact form factor, and allows the user to selectively deploy subsets of the arms 16, 18, 22 depending on the specific use case. For example, a use case where one surgical arm 16 is needed, and the video output is sent to large operating room (OR) monitors rather than using the integrated monitors 20 may result in the monitors 20 staying retracted while one surgical arm 16 is deployed. Deployment and docking may be motorized and automated, which enables a simple and elegant setup where it might otherwise be overwhelming or complicated.

Figure 4:
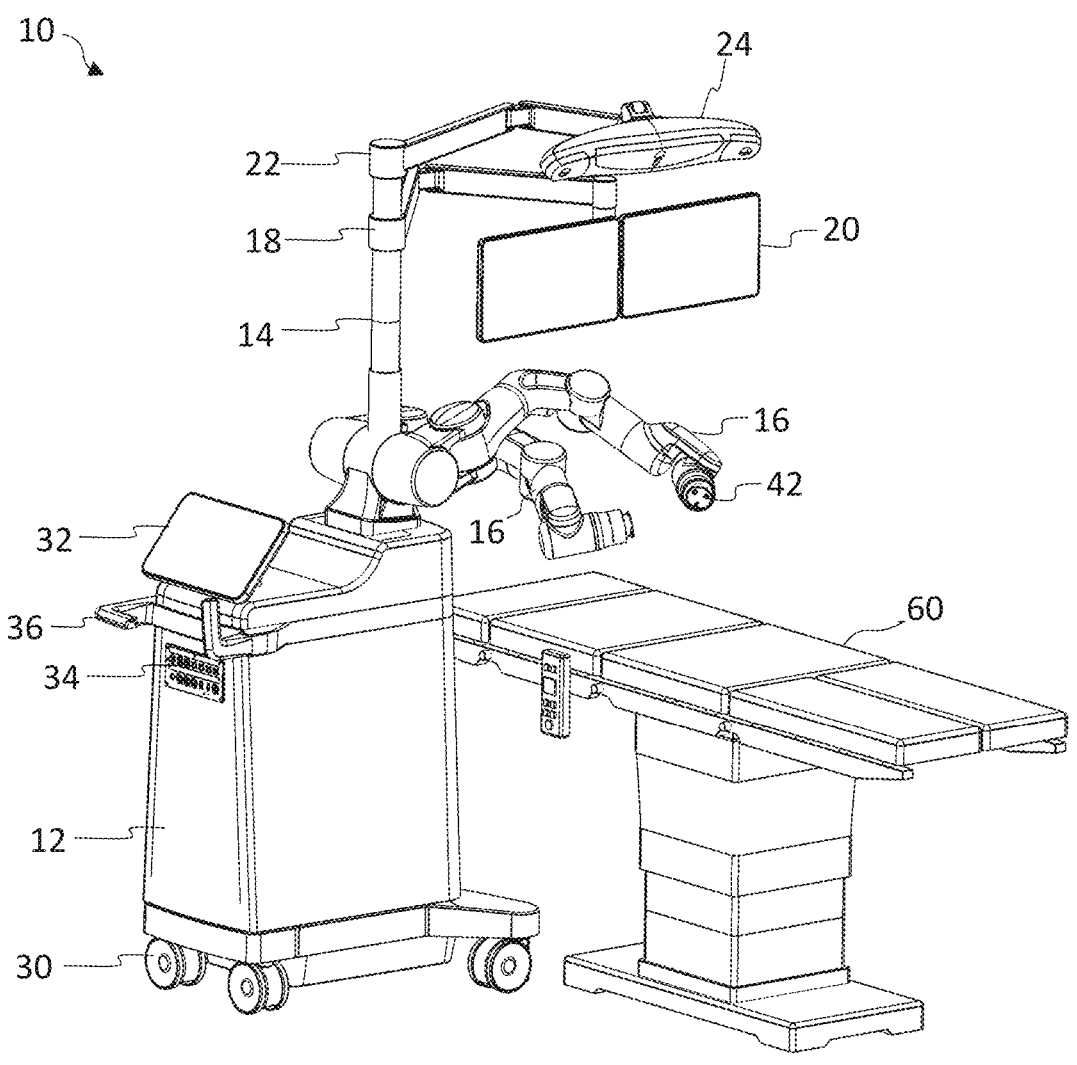
FIG. 4 shows the deployed surgical robotic system positioned next to an operating room table.

Turning now to FIG. 4, system positioning at the operating room table 60 is flexible and may be based on surgeon preference for a given procedure. The multi-arm surgical robotic system 10 may be positioned next to, or across from the surgeon, and may also be located toward the foot or head of the patient 62. In all these combinations, the surgical arms 16 have a large working volume on both sides of the table 60 without moving the system base 12, and the monitors 20 and camera 24 may be positioned along the midline of the table 60. This camera position limits line of sight issues, and the monitor position is more ergonomic for the surgeon than other systems. In the embodiment shown in FIG. 4, both surgical arms 16 are the same in length and configuration. Alternatively, the surgical arms 16 may be different. The length of one arm 16 may be increased, for example, through an attachment at the end between the end of the arm 16 and the end effector 26, or two distinct arm configurations may be provided. This differentiation in length and/or type may lead to a primary arm and a secondary arm when positioning in the OR and deploying for procedures.

Figure 5A:
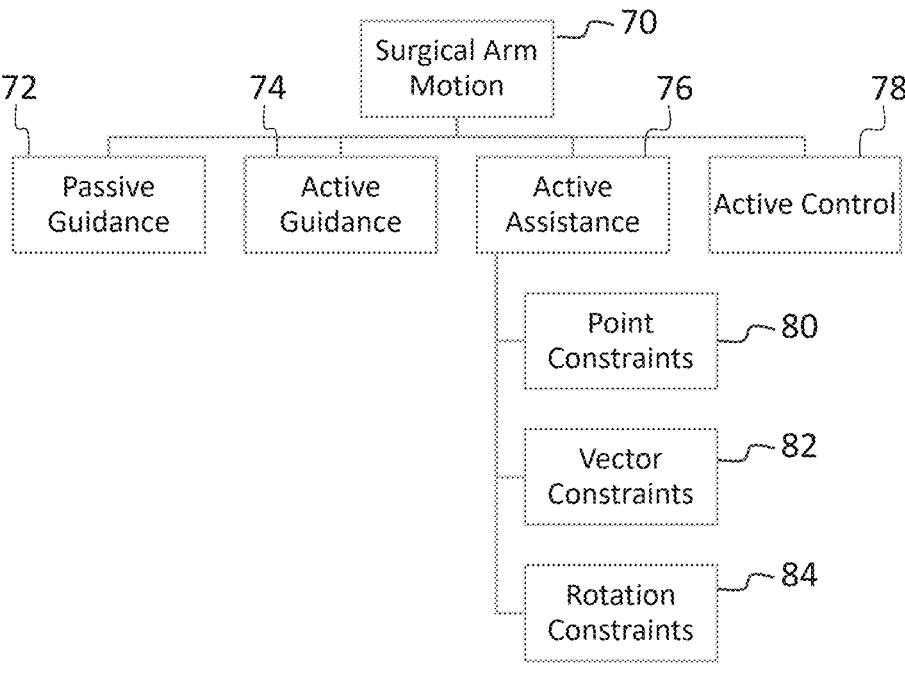
FIGS. 5A-5B demonstrate the surgical arm movement types and functionality including point, vector, and rotation constraints controlled by force-input from the user.
Figure 5B:
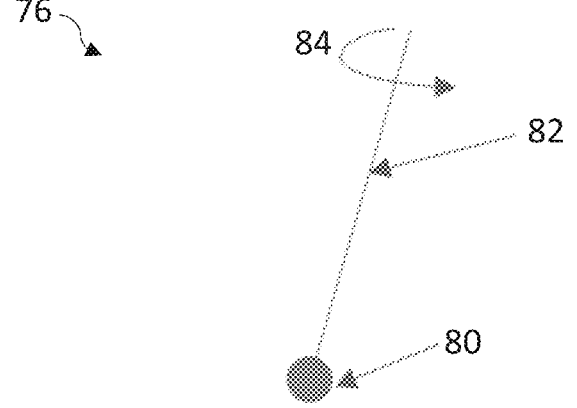

Turning now to FIGS. 5A-5B, the surgical arms 16 may have improvements in accuracy, articulation, and enhanced motion capabilities while directly interacting with the patient 62. The enhanced surgical arm motion 70 may be grouped into four move mode categories: passive guidance 72, active guidance 74, active assistance 76, and active control 78. During passive guidance 72, the system 10 moves the surgical arm(s) 16 to a position and holds that position. Once in position, the system 10 is static and passively guides instruments 28 controlled by the surgeon. During active guidance 74, the system 10 moves the surgical arm(s) 16 to a position and servos in-place, making dynamic adjustments to maintain relative position to the patient 62 as anatomy moves. During active assistance 76, the surgical arm(s) 16 are controlled by force-input from the user, allowing motion within a specified combination of constraints. As shown in FIG. 5B, the constraints may include point constraints 80, vector constraints 82, and rotation constraints 84. The point constraints 80 may include free, defined, on a vector, on a plane, and/or inside a volume. The vector constraints 82 may include free, defined, parallel to vector, and/or normal to plane. The rotation constraints 84 may include free and/or defined. During active control 78, robotic motion based on a plan may be enabled by continuous activation of a dead-man switch. Some examples may include drilling, tapping, screw placement, disc removal, cage placement, and bone removal.

Active modes 74, 76, 78 enable tissue volume removal, such as facetectomy, laminectomy, discectomy, etc., in addition to milling, drilling, tapping, driving screws, and other functions. All active move modes 74, 76, 78 may be enabled by a supervisor safety control system. The supervisor is a redundant control system in parallel with the primary motion control system, which monitors all feedback devices (encoders, switches, force sensors), motor currents, and joint velocities and compares these readings to the primary motion control system. It also compares the readings to the expected values given the commanded motion. If there are any discrepancies between supervisor and the primary motion control system, or between expected values and the supervisor readings, the supervisor control safely stops all motion.

The active movement and multiple surgical arms 16 allow for the system 10 to assist with more surgical procedures, such as active milling, placement of longer instruments, and simultaneous robotic action (e.g., holding a retractor and assisting with disc prep). This may help to improve the accuracy of the overall procedure and reduce the cognitive load of the surgeon. The dual surgical arms 16 and dual monitors 20 also enable multiple surgeons to actively participate in the surgery simultaneously, thereby reducing the overall time of procedure. The non-sterile monitor 32 allows the non-sterile staff to actively assist while not disrupting the surgical monitors 20. The integration of all components into one mobile platform reduces the overall footprint of the computer-assisted technology in the OR. The reduced footprint may also improve the usability of the system 10 for the staff as it is not as disruptive to their standard layout. The automated peripheral arms 18, 22 and overall collaborative motion of the system 10 may streamline the setup and reduce the navigation fiddle factor during the procedure. Automated camera adjustments ensure the patient/robot are in view of the camera 24 so there are no disruptions in active navigation. The enhanced line of sight reduces wasted time by removing manual adjustments, and improves accuracy and overall usability of the system.

Turning now to FIGS. 6-10, the multi-arm surgical robotic system 10 is configured to complete multiple surgical tasks, simultaneously or sequentially, in accordance with some embodiments. For example, in a dual-arm system, each surgical arm 16 is integrated into a single system 10 allowing for coordinated procedural use cases and methods. Each surgical arm 16 may be able to perform an independent operation while working together in a synchronized fashion. Each surgical arm 16 may function at the same time or may coordinate in succession depending on the type of procedure.

During spinal procedures, the surgical arms 16 may be configured to install implants, such as pedicle screws and interbody implants, to optimize workflow of the operation and reduce surgical time. For example, the surgical arms 16 may be positioned to install bilateral pedicle screws in the same vertebra at the same time. The surgical arms 16 may be positioned to install pedicle screws unilaterally for the same spinal rod at the same time. The surgical arms 16 may be coordinated to stepwise install multiple pedicle screws along a series of vertebrae. One or both of the surgical arms 16 may be configured to install interbody implants, for example, through anterior cervical discectomy and fusion (ACDF), posterior cervical fusion (PCF), anterior lumbar interbody fusion (ALIF), transforaminal lumbar interbody fusion (TLIF), posterior lumbar interbody fusion (PLIF), and lateral lumbar interbody fusion (LLIF) procedures. For example, the surgical arms 16 may be positioned to install two interbody implants at multiple levels at the same time or coordinated stepwise. Each surgical arm 16 may be aligned along a different surgical approach, for example, one level positioned through a transforaminal approach and another level positioned through a posterior approach. One surgical arm 16 may be configured to perform one type of task while the other arm 16 performs a different surgical task. For example, one surgical arm 16 may install a pedicle screw while the second surgical arm 16 installs the interbody implant. It is contemplated that the system 10 may be configured to install any suitable implants or perform other surgical tasks in any suitable order to optimize the surgical workflow. These procedures are merely exemplary and other suitable functions and workflows may be used based on the given procedure.

In some cases, the surgical arms 16 may be configured to optimize navigation. For example, navigation may be enhanced by additionally navigating from a specific or identified area of bone during the procedure. For example, one of the surgical arms 16 may be attached to a specific portion of bone, such as an osteophyte, facet, lamina, pedicle, spinous process, transverse process, or other area of vertebra. The bone may also include the femur, tibia, humerus, clavicle, fibula, ulna, bones of the hand, bones of the feet, or other suitable bone(s) or joint(s). Once a portion of bone is identified (e.g., an osteophyte), the end effector 26 of the first surgical arm 16 may attach to the identified location. Another portion of bone may be identified (e.g., a pedicle), the end effector 26 of the second surgical arm 16 may attach to the next identified location while the first surgical arm 16 remains rigidly attached to the first identified location. Once the second surgical arm 16 is attached, the first surgical arm 16 may be removed while leaving the second surgical arm 16 rigidly attached to the next identified location. The procedure may continue such that at least one of the first and second surgical arms 16 remain attached to bone at all times to act as a navigation source for enhanced navigation of the surgical robotic system. With the first surgical arm 16 free, the first surgical arm 16 may complete a surgical task, such as removing the osteophyte, facet, lamina, or the like.

In one embodiment, a method may include (a) guiding a first surgical arm 16 of the surgical robotic system to a location on bone of a patient and attaching the first surgical arm 16 to the location on the bone; (b) navigating a second surgical arm 16 of the surgical robotic system based on the first attached surgical arm; and (c) performing a surgical task while one surgical arm 16 remains rigidly attached to the bone to act as a fixation anchor point for the bone and for providing spatial information about a location of the bone to the surgical robotic system. The first surgical arm 16 may be guided to a facet, lamina, or osteophyte, for example. The second surgical arm 16 navigates off the given facet, lamina, or osteophyte. The surgical task may include a decompression procedure, such as an osteotomy, laminectomy, laminotomy, laminoplasty, facetectomy, discectomy, foraminotomy, corpectomy, annuloplasty, ligament release, interspinous spacer, interbody spacer, or other suitable technique.

In one embodiment, a method may include (a) identifying an osteophyte, attaching the end effector 26 of a first surgical arm 16 to the osteophyte, and leaving the first surgical arm 16 rigidly attached to the osteophyte; (b) navigating the end effector 26 of a second surgical arm 16 based on the first surgical arm while the first surgical arm 16 remains rigidly attached to the osteophyte, and attaching the end effector 26 of the second surgical arm 16 to another location, and once attached, removing the first surgical arm 16 while leaving the second surgical arm 16 rigidly attached; and (c) removing the osteophyte while leaving the second surgical arm 16 rigidly attached to bone. The end effector 26 may include a powered end effector for cutting bone. Once the second surgical arm 16 is rigidly attached, the first surgical arm 16 may be navigated to the osteophyte, and the osteophyte may be partly or fully removed.

During other orthopedic procedures, the surgical arms 16 may be configured to install implants, such as plates, screws, and intramedullary nails, to optimize workflow of the operation and reduce surgical time. For example, the surgical arms 16 may be aligned along different trajectories to secure screws or anchors into a fracture plate or an intramedullary nail for treatment of trauma fractures. The surgical arms 16 may be configured to guide or position one or more components of a knee or hip reconstruction. The surgical arms 16 may be used separately or together for cranial procedures. Each of the surgical arms 16 may execute distinct operations independently, while also operating in unison in a coordinated manner depending on the specific requirements of the surgical procedure.

Although the robot and associated systems described herein are generally described with reference to spine and orthopedic applications, it is also contemplated that the robot system is configured for use in other surgical applications, including but not limited to, surgeries in trauma or other orthopedic applications, cranial, neuro, cardiothoracic, vascular, colorectal, oncological, dental, and other surgical operations and procedures.

Figure 6:
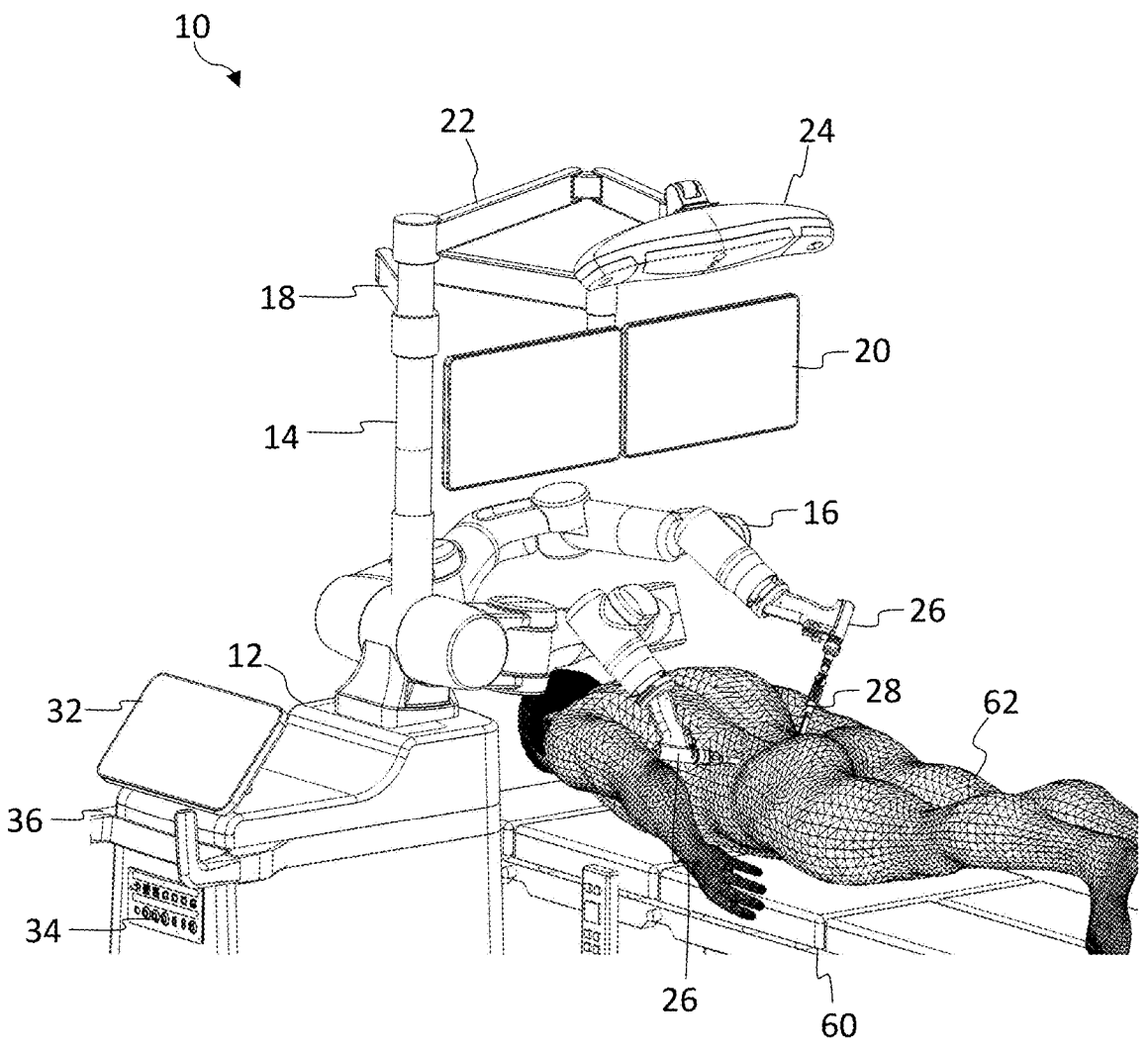
FIG. 6 shows an example of simultaneous active approaches with the surgical arms of the surgical robotic system.

With further emphasis on FIG. 6, a simultaneous active approach of both surgical arms 16 is shown according to one embodiment. During simultaneous active approaches, each surgical arm 16 works in concert to perform multiple surgical tasks actively and independently. In this embodiment, the surgical arms 16 may align the end effectors 26 simultaneously along different respective trajectories or may be mirrored across the patient's midline. For example, the patient 62 may be positioned prone on the OR table 60 such the end effectors 26 may be aligned along trajectories suitable for installation of bilateral pedicle screws. The simultaneous approach may improve efficiency in single position surgeries, for example, having lateral and prone access to a vertebral level at the same time. By moving the surgical arms 16 in concert, the system 10 also facilitates alignment and mating to implants that require secondary actuation stage in situ, such as highly articulated expandable cages, or cross-pinning/cross-screwing, such as plates or threaded spacers. Examples of other active applications may include simultaneous electrode placement in cranial procedures or simultaneous targeting in trauma applications.

According to another embodiment, one or more of the surgical arms 16 may be configured to hold a retractor, distractor, cannula, or other access tools, for example, for minimally invasive surgical procedures. With multiple surgical arms 16 available, one surgical arm 16 may be dedicated to positioning and holding a retractor, for example. Because both of the surgical arms 16 and the patient 62 are tracked, one surgical arm 16 may be used to dynamically adjust the retractor position as the patient moves. In addition, force sensing in the surgical arms 16 may be used to monitor the forces being exerted on the patient. While one surgical arm 16 is dedicated to dynamically positioning the retractor, the remaining arm(s) 16 may work through the opening that the retractor provides, performing surgical tasks, such as volume removal, drilling, driving, etc. Since the surgical arms 16 are controlled by the same system 10, the operative arm 16 may synchronize motion to follow any adjustments made by the retractor arm 16.

In addition to positioning a manually actuated retractor, the system 10 may be used to position a robotically actuated retractor. In other words, the end effector 26 may be replaced with a specialized robotic retractor end effector configured to provide better visibility and access to the surgical site. The surgical arms 16 provide a flexible end effector interface 42 with hard-wired power and communication through a sterile barrier. The end effector interface 42 may be used to power and control the robotically actuated retractor. The robotic retractor may include two, three, or more retractor blades, which may be adjusted and controlled robotically and/or manually. Further details of retractors can be found, for example, in U.S. Pat. No. 11,234,788, which is incorporated by reference herein in its entirety for all purposes. Force sensors may also be integrated into the retractor to characterize and monitor the retraction forces induced on the patient.

Figure 7:
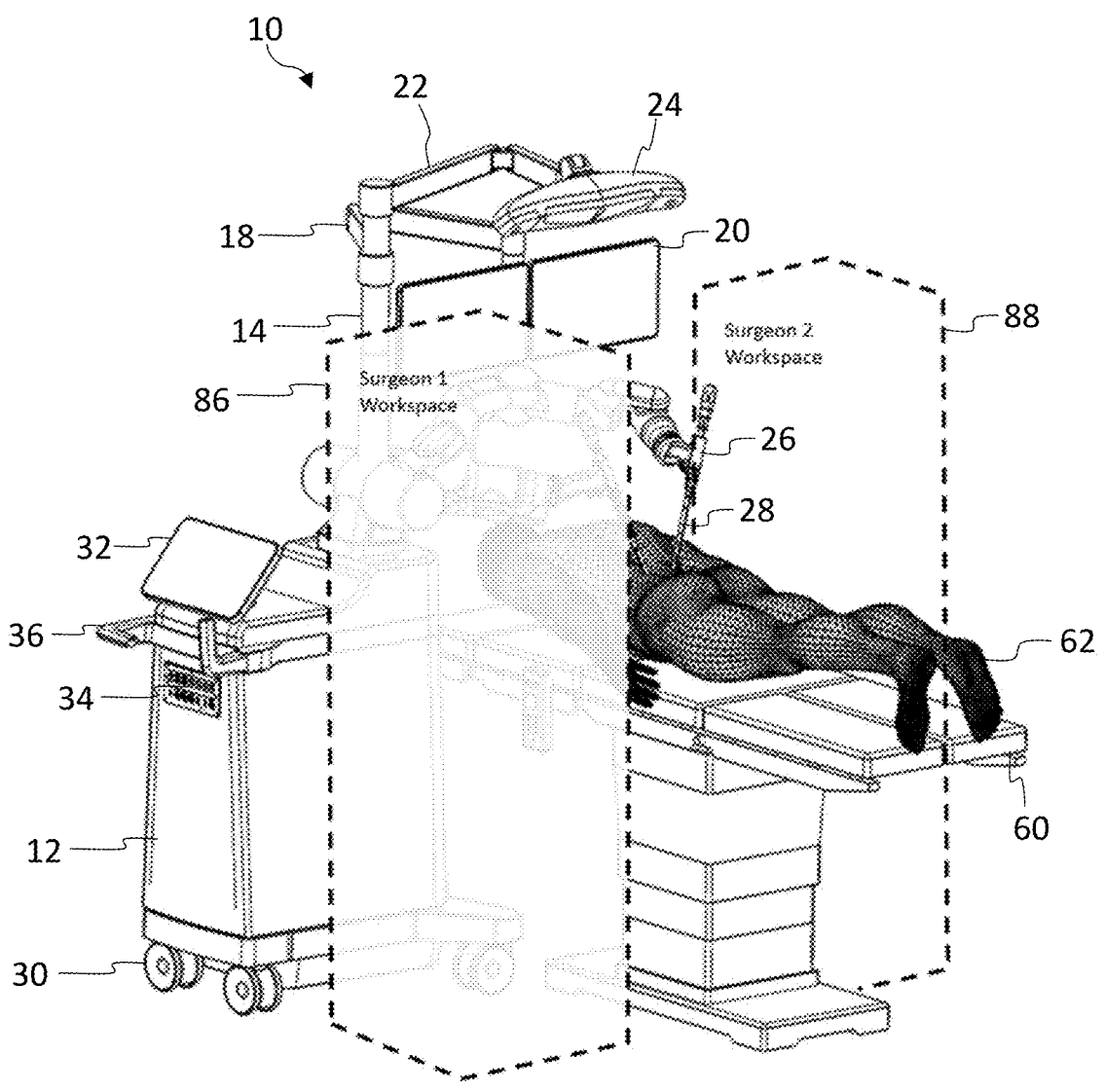
FIG. 7 shows an example of two surgeon workspaces with two active users during the procedure.

With further emphasis on FIG. 7, a multi-player mode may allow for each surgical arm 16 to be controlled by a different user in accordance with one embodiment. In a dual-user mode, two users may have separate workspaces 86, 88 to control each respective surgical arm 16. When there are two surgeons, the first surgeon may have a first workspace 86 and the second surgeon may have a second workspace 88. For example, surgeons may be positioned on either side of the OR table 60 with each surgical arm 16 assigned to an individual surgeon. In this dual-user mode, the system software enables two player mode in which the system 10 understands there are two active users during the procedure. Each surgeon may have customized viewports and can activate their surgical arms 16 independently. The non-sterile monitor 32 may also have a custom viewport, including a mirror of either of the surgical viewports. The system software may be configured to detect and avoid any collisions between the two players and/or the surgical arms 16. This dual-user configuration enables concurrent work, increasing efficiency and decreasing surgical time for the patient 62. An example case for this mode may include placing pedicle screws simultaneously on both sides of the patient 62. Simultaneous screw placement may be valuable in large deformity cases where many screws are used in a construct, thereby streamlining the procedure and decreasing operative time. It will be appreciated that other surgical procedures may also benefit from a dual-user configuration.

With further emphasis on FIG. 8A-8D, an active fixation workflow is shown according to one embodiment. By contrast to single arm robotic systems, having multiple integrated surgical arms 16 allows for multipart workflows, for example, for complex deformity cases. For example, in one workflow, the patient 62 may be positioned prone on the OR table 60 for posterior pedicle screw fixation with the surgical arms 16 located on opposite sides of the patient 62. The surgical arms 16 may be configured to rigidly attach to the pedicle screws in an alternating fashion to act as anchor points, thereby improving accuracy throughout the procedure. This specific use case for pedicle screws can be generalized to apply to any case where bony anatomy is mobile and can benefit from fixation. Some non-limiting examples may include affixing one or more vertebral bodies while correcting a deformity, such as scoliosis, affixing the vertebral body while performing bone removal, affixing the vertebral body while cleaning out adjacent disc space, affixing the vertebral body while placing an interbody spacer, affixing the femur or tibia while performing total or partial knee arthroplasty, affixing one or more bone(s) for treating orthopedic trauma, and other orthopedic procedures.

Figure 8A:
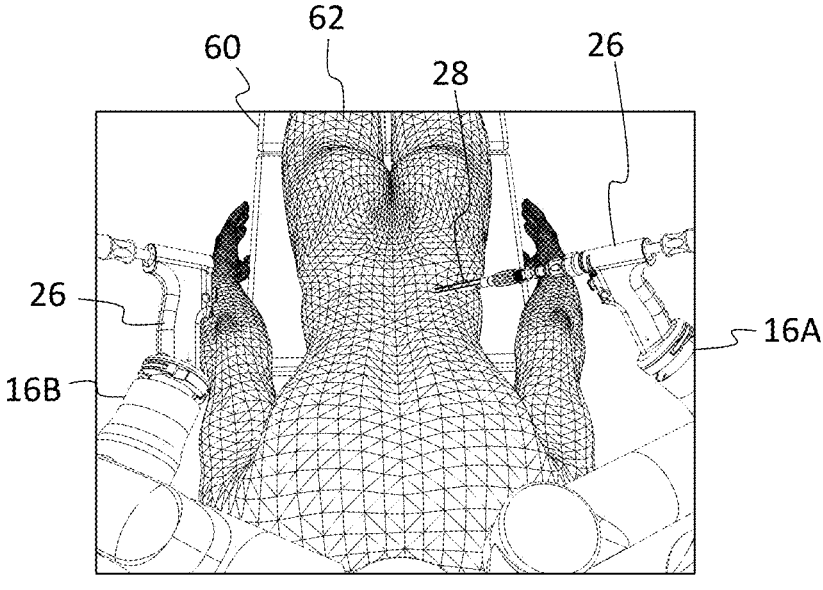
FIGS. 8A-8D show an example of placing pedicle screws with the multiple surgical arms.
Figure 8B:
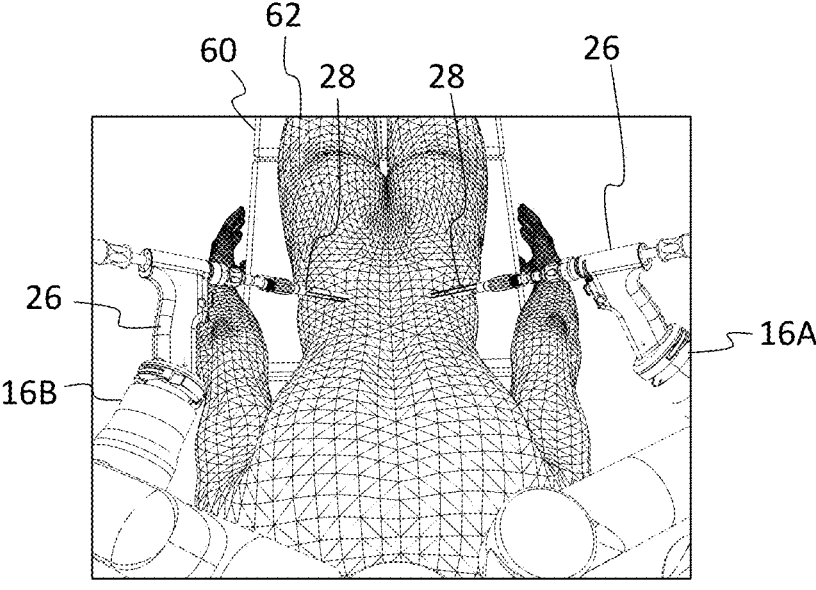
Figure 8C:
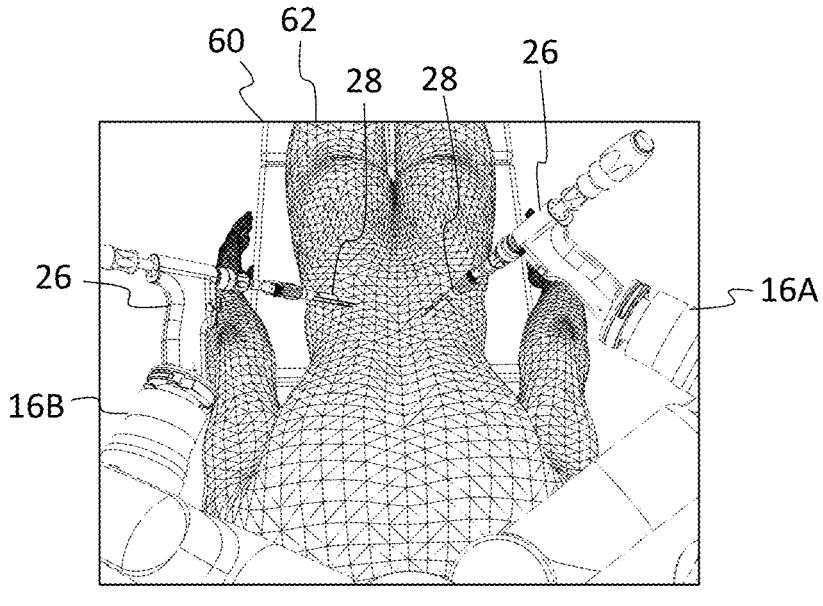
Figure 8D:
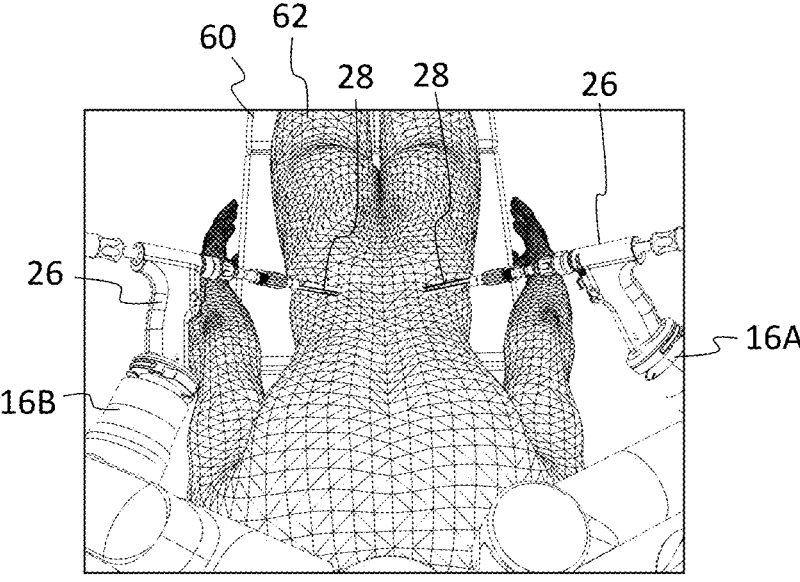

In FIG. 8A, the first surgical arm 16A holds the end effector 26 having a guide tube aligned along the planned trajectory. An instrument 28, such as a first drill, passes through the guide tube, with the least disruption to the anatomy. After drilling, a first tap or screw may be placed. As shown in FIG. 8B, the first robot arm 16A remains rigidly attached to the patient while the free surgical arm 16B drills the contralateral side. The first arm 16A provides a fixation anchor point for the vertebral body, dramatically reducing motion and providing spatial information about the location of the vertebral body through kinematics. The second arm 16B then places its tap or screw, and in turn remains rigidly attached while the first arm 16A is removed and proceeds to the next level. As shown in FIG. 8C, the free arm 16A moves to the next level to install the next pedicle screw. As shown in FIG. 8D, this process is repeated until all screws for the construct are placed. Systematically transitioning from anchor point to anchor point allows the last screw to be as accurate as the first. Maintaining accuracy during long procedures is particularly important for cases where anatomy is highly mobile, such as in the cervical spine. After one or more pedicle screws are installed, the spinal rod may be connected to the pedicle screws to prevent movement and stabilize the spinal segments.

One surgical method for placing pedicle screws may include the following steps: (1) Drill, tap, and drive a first screw and leave the surgical arm 16 rigidly attached to the patient 62 via the screw (as shown in FIG. 8A). (2) Drill, tap, and drive the contralateral screw while the system remains rigidly attached to the first screw (as shown in FIG. 8B). Since the vertebral body is held in place by the first screw, the second screw is placed with improved accuracy. Leave at least one surgical arm 16 rigidly attached to the patient at all times. (3) With the free arm 16, move to the next level to drill, tap, and drive the next screw (as shown in FIG. 8C). Since the system is rigidly holding the adjacent level, accuracy for this third screw is also improved. (4) Repeat this process until all screws for the construct are placed (as shown in FIG. 8D).

Figure 9:
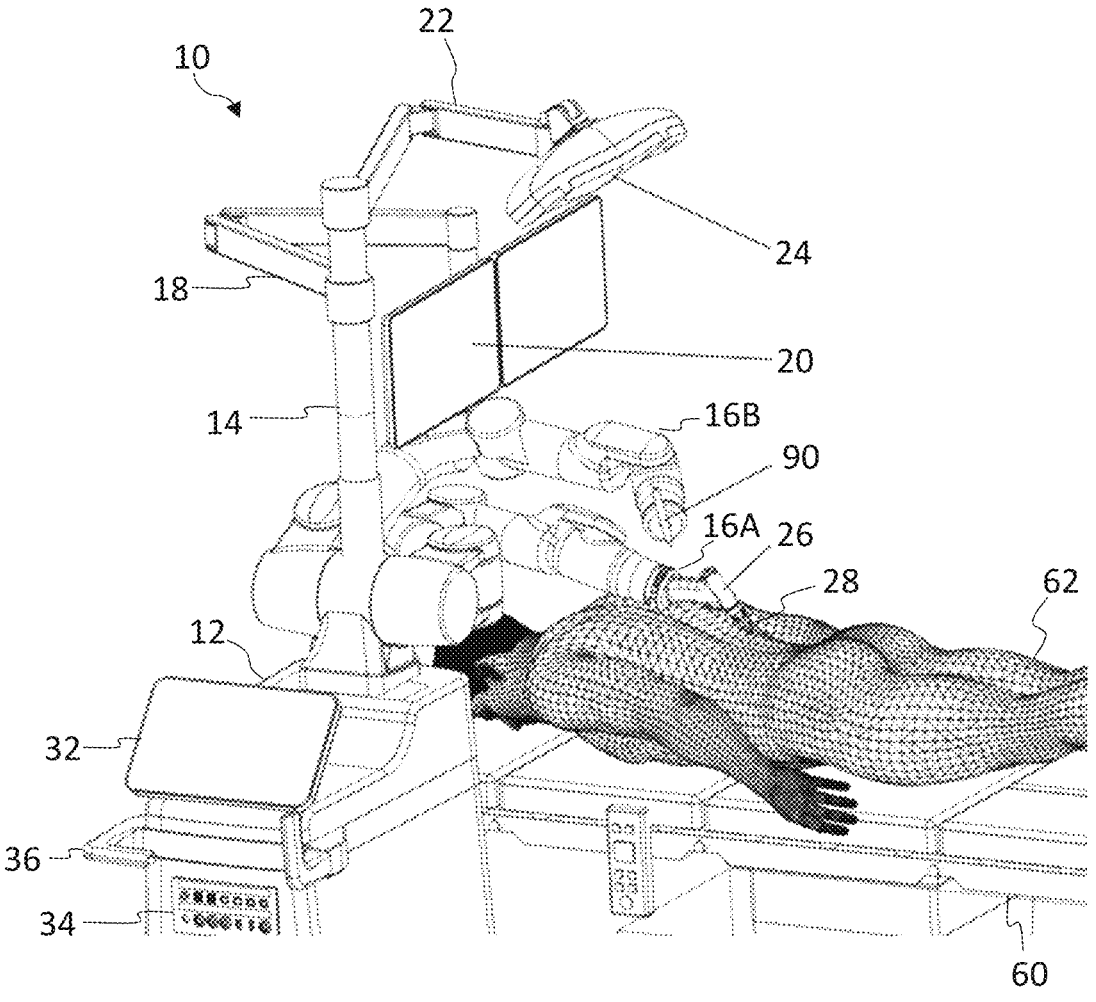
FIG. 9 shows an example of using the surgical robotic system in pantograph mode to magnify working volume and scale for fine adjustments.
Figure 10:
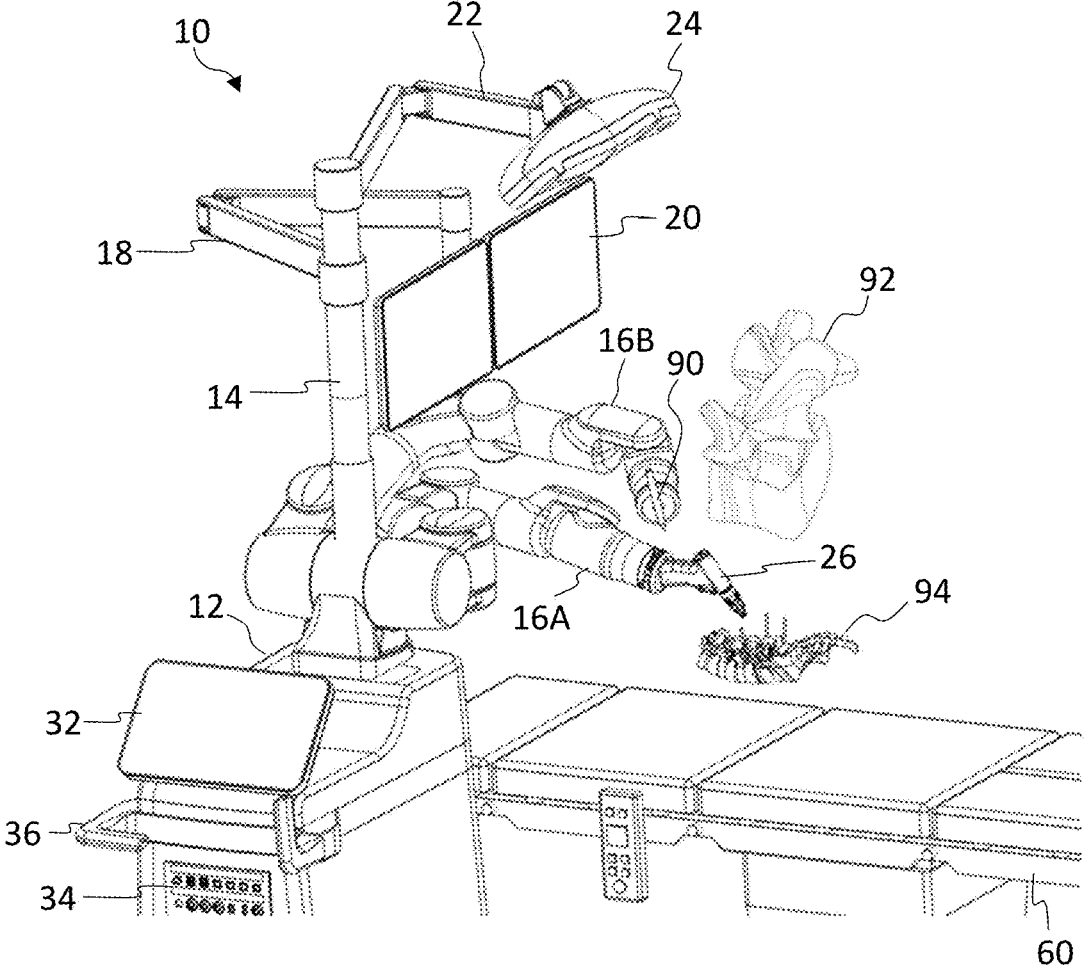
FIG. 10 shows an example of using the surgical robotic system with the pantograph registered with an augmented reality object (only the spine of the patient is shown here)

With further emphasis on FIGS. 9-10, a sterile robotic pantograph or master-slave workflow is shown according to one embodiment. A pantograph is a mechanical linkage used to duplicate tool paths identically or with a scaling factor depending on the ratio of link lengths. With two or more surgical arms 16, the system 10 is configured to robotically emulate pantograph functionality in 3D space, giving surgeons a magnified working volume and scaling their movements down to fine adjustments in the patient 62. In the pantograph mode, one surgical arm 16 controls the other surgical arm 16, which performs the surgical task. As shown in FIG. 9, the patient 62 may be positioned prone on the OR table 60, for example, with the robotic system 10 positioned on one side near the head of the patient 62. The surgeon has the choice to stand next to the system 10 or across from the system 10 in this mode. This enables an unobstructed line of sight by camera 24, and easy viewing of the displays 20, which may show magnified visualization of the surgical site. Each surgical arm 26 has a 6-axis load cell 44 at its distal end.

In the sterile pantograph mode system arrangement, a first surgical arm 16A may include the powered end effector 26 with a tool 28, which performs the surgical task. For example, the first arm 16A may be equipped with typical instrumentation 28 (e.g., a burr), which interacts directly with the patient 62. The second arm 16B is equipped with a tool, such as a stylus 90, for the surgeon interface. The surgeon input stylus 90 may be directly held or manipulated by the surgeon to control the first surgical arm 16A. The stylus arm 16B positions the stylus 90 in space above the surgical site in a way that preserves the surgeon's direct line of sight. The load cell 44 at the end of the stylus arm 16B reads the force input from the surgeon and moves accordingly. Inverse kinematics from the stylus arm 16B are used to control the instrument position and orientation, duplicating the stylus path but scaled down for fine adjustments. Scaling factors are flexible and may be selectable by the user. As the stylus 90 is manipulated in space by the surgeon, the working surgical arm 16A performs the given procedure in real time.

Other notable attributes of the pantograph use mode may include one or more of the following: (1) The system may provide haptic feedback based on forces sensed at the first arm's load cell 44 to the surgeon at the stylus 90 of the second arm 16B, preserving the surgeon's tactile feel. (2) Force input from the surgeon may be decoupled from any reaction forces through the instrument 28 from the patient 62. This decoupling allows the load cell 44 at the instrument arm 16A to use its full dynamic range, sensing forces applied to the patient 62 and implants. (3) The stylus 90 may be integrated into the sterile end effector 26 such that the surgeon can enter and exit the pantograph mode without breaking sterility, and while maintaining natural line of sight to the anatomy. (4) The system may be combined with an endoscope or exoscope to provide magnified visualization of the surgical site and improve visual feedback. (5) As shown in FIG. 10, the system may be combined with an augmented reality solution, such as a headset with anatomical overlay. The input motion is registered with a magnified surgical volume, with the magnified input motions being scaled to the same magnification as the virtual object 92. The augmented virtual object 92 may be a magnified portion of the patient's spine 94, for example. (6) The system may be combined with an additional monitor showing a magnified view of the surgical anatomical 3D volume (CT/MRI) or a cartoon of the anatomy, with which the surgeon interacts using the stylus 90.

Figure 11:
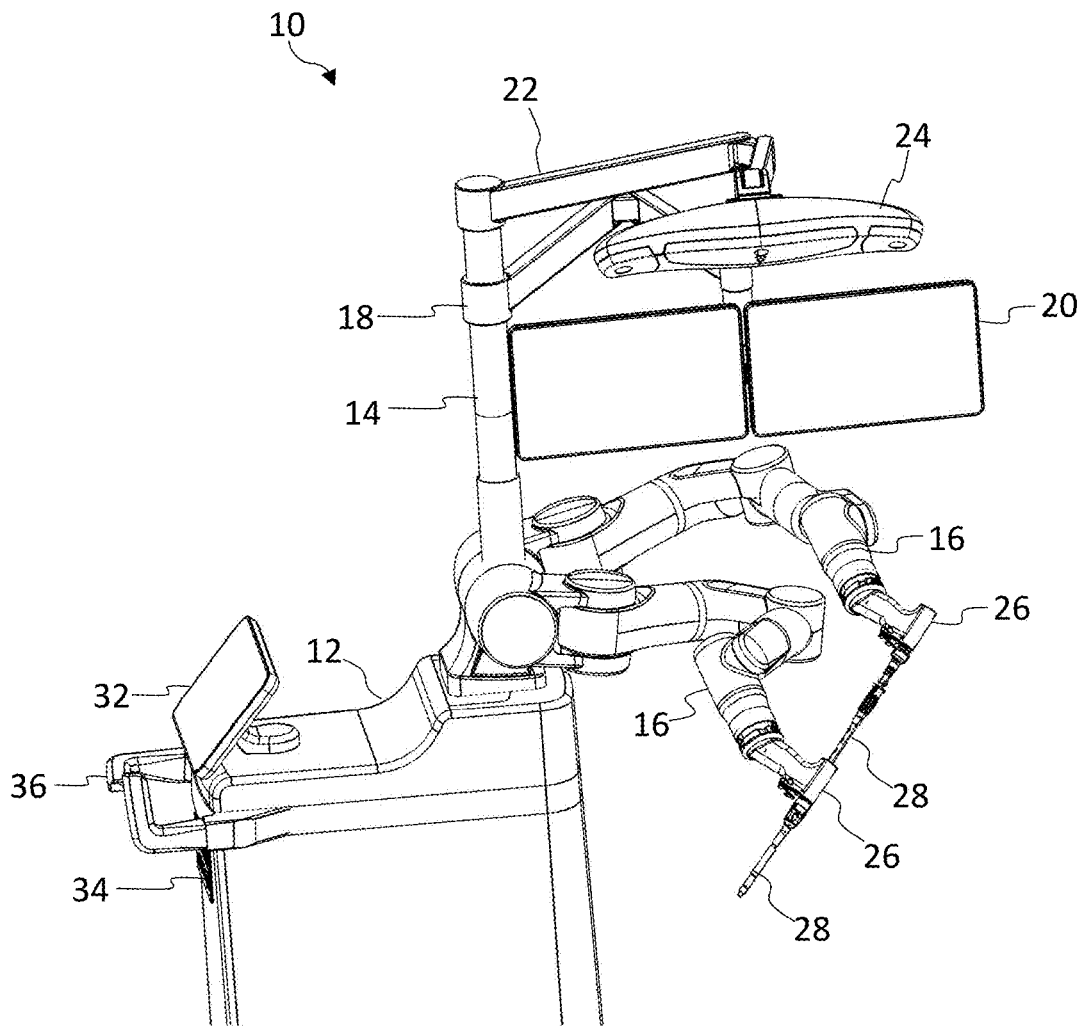
FIG. 11 shows an automated two-armed instrument verification for confirming the instrument tip position according to one embodiment.

Turning now to FIG. 11, a two-armed instrument verification is shown according to one embodiment. During a verification procedure, the tip of any instrument 28 may be seated into a precision divot of another instrument or end effector for software verification. The software verification ensures that the instrument 28 is visible and registered with the robotic software. The navigation camera 24 tracks both arrays while the tip is seated, and thereby confirms the instrument tip position. With two or more surgical arms 16, this procedure may be automated with robotic motion as shown in FIG. 11. One surgical arm 16 positions the tip of the instrument 28 into a divot in the back of the end effector 26 held by the other surgical arm 16. The navigation camera 24 tracks the instruments 28 as they move into verification position, and the camera 24 can continue to be used to verify the tip position. Repeatability for the two-armed verification is dramatically increased compared to the manual process. Alternatively, the process may improve verification accuracy by aggregating camera and kinematic feedback. In another embodiment, the system enables a kinematics only verification that does not require a camera and instead relies on precision encoder feedback in the surgical arms 16. In another embodiment, the system introduces capability for a bent-tip or runout verification by robotically rotating the instrument 28 through know increments and re-checking tip location. In yet another embodiment, the system may move the instrument 28 to the camera's field of view (FOV) for an automatic machine vision identification, verification, and calibration. It will be appreciated that any suitable method may be employed for automatic instrument verification by the dual-arm system 10.

Alternative Robotic Systems

Figure 12A:
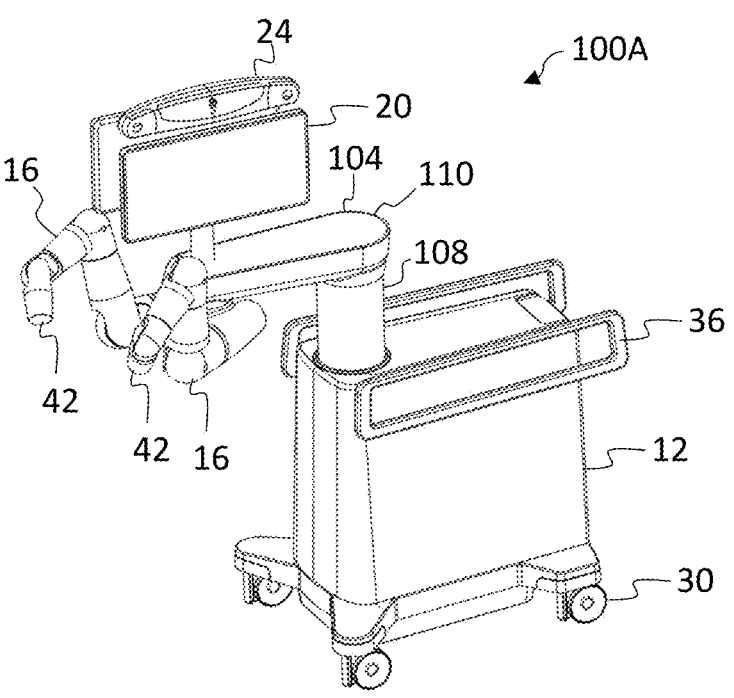
FIGS. 12A-12B show alternative arm configurations for a surgical robotic system having a vertical column and bifurcated arm locations above and below an upper arm, respectively.

Turning now to FIG. 12A-17B, the arrangement of the robotic system components may be modified into different configurations, thereby providing different movement and positioning of the components. With reference to FIGS. 12A-12B, multi-arm surgical robotic systems 100A, 100B are shown with bifurcated arms in accordance with further embodiments. Robot systems 100A, 100B are similar to multi-arm surgical robotic system 10 except the vertical arm positioner 14 is replaced by a 3-axis positioner 104. In this embodiment, all surgical arms, peripheral arms, and non-sterile components are integrated into a single, mobile cart. The integrated cart configuration minimizes the total required footprint in the operating room, while simplifying setup, breakdown, and storage. During use, the mobile cart is positioned at the operating room table 60 to assist with the operation as described herein.

Figure 12B:
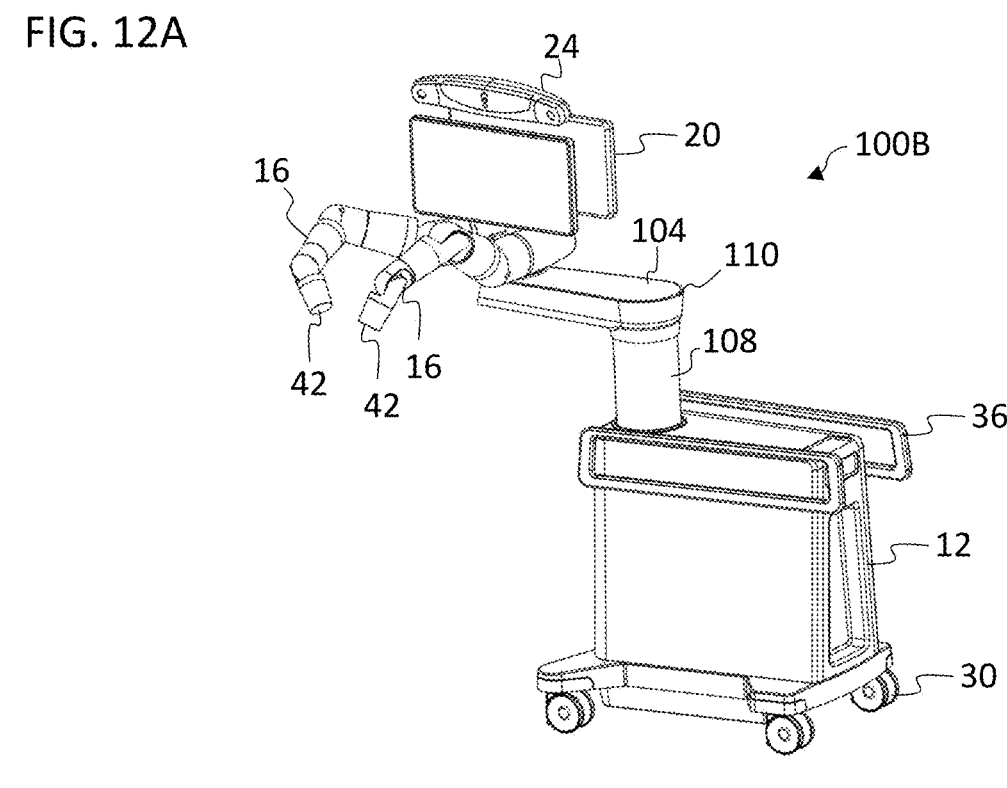

The 3-axis positioner 104 may include a vertical positioner link or arm 108 and a horizontal positioner link or arm 110. The vertical arm 108 provides a prismatic vertical joint, which allow for linear movement along a single vertical axis. The prismatic vertical joint is followed by two parallel revolute joints or rotatory joints, which permit rotation. The prismatic joint allows the 3-axis positioner 104 to reach higher or lower, adjusting the vertical position, while the two parallel revolute joints enable the surgical arms 16 to be extended and positioned optimally in the operating room. For example, the positioner 104 may locate the common swivel point at roughly mid-line of the OR table. The surgical arms 16 may be attached to the free end of the horizontal arm 110 by respective swivel mounts. In FIG. 12A, system 100A includes surgical arms 16, which are mounted below the horizontal positioner link 110. In FIG. 12B, the system 100B includes surgical arms 16, which are mounted above the horizontal positioner link 110. The surgical arms 16 may be similar to the arms described for system 10, where the left and right surgical arms 16 each allow for movement with seven degrees of freedom (7 DoF). For example, the 7 DoF arm arrangement may include roll×pitch×roll×pitch×roll×pitch×roll. The monitors 20 and navigation camera 24 may be mounted to the free end of the horizontal positioner arm 110, for example, with a vertical post. The monitors 20 and camera 24 may be stationary or coupled via auxiliary arms to position the respective components. As shown, the monitors 20 may be positioned back-to-back, such that an assistant may view the procedure from outside the surgical space. Similar to system 10, the multi-arm surgical robotic systems 100A, 100B may have deployed and docked system configurations.

Figure 13:
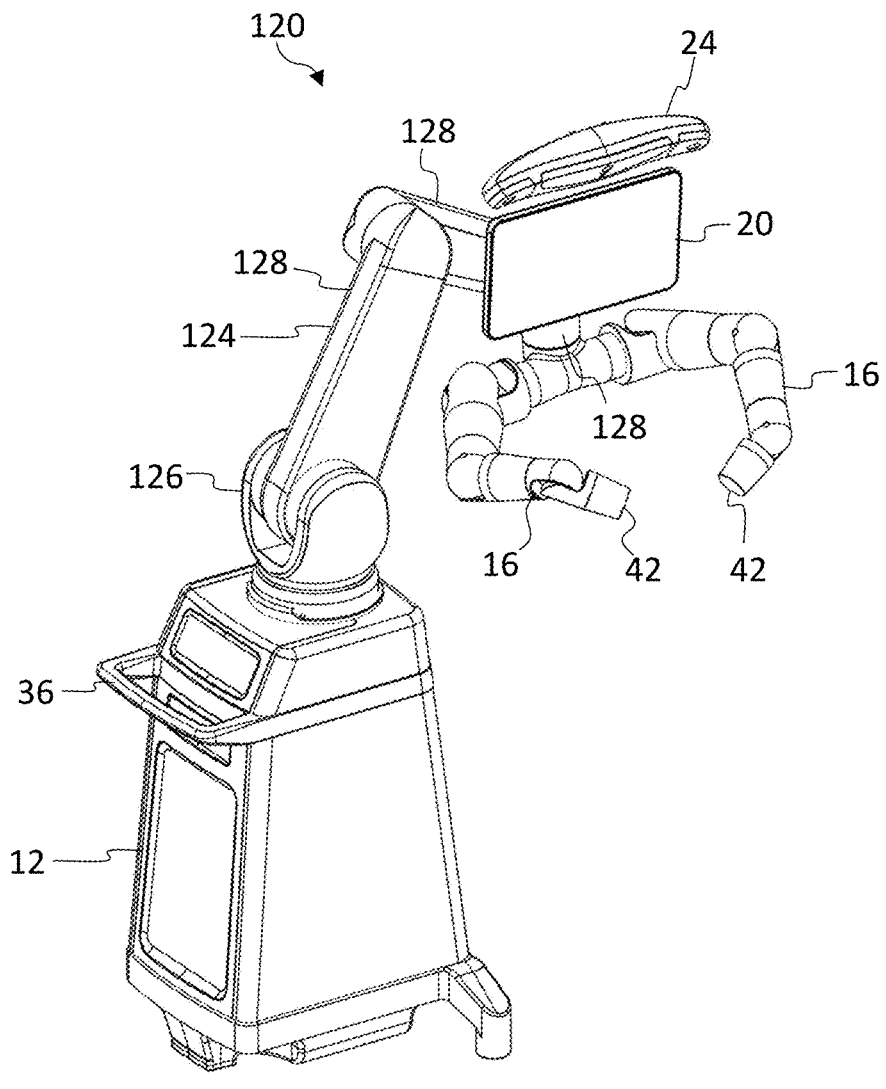
FIG. 13 shows a surgical robotic system having a positioner with revolute joints for five degrees of freedom according to one embodiment.

With reference to FIG. 13, a multi-arm surgical robotic system 120 is shown according to one embodiment. In robot system 120, the vertical arm positioner 14 is replaced by a five degree of freedom positioner 124. Robotic system 120 has a pedestal configuration where the positioner 124 sits atop of the system 120. Unlike the vertical axis on system 10, the positioner 124 is located on top of the base 12 without extending into the body of the system. This allows the overall size of the cabinet 12 to be reduced compared to system 10. In this embodiment, a single monitor 20 and navigation camera 24 may be mounted to the free end of the positioner 124 with the surgical arms 16 located beneath the monitor 20.

The positioner 124 may include a plurality of positioner links or arms 128 with revolute joints therebetween. In one embodiment, the positioner 124 includes a five degree of freedom (5 DoF) arrangement. For example, the 5 DoF arm arrangement may include roll×pitch×pitch×pitch×roll. A clevis 126 may attach to the base 12 about a first roll joint, which allows the clevis 126 to rotate around the base 12. A first positioner arm 128 attaches to the clevis 126 at a first pitch joint, which enables to the positioner 124 to tilt forward and backward. A second positioner arm 128 attached to the first positioner arm 128 about a second pitch joint, which provides an additional degree of up and down tilting. A third positioner arm 128 attached to the second positioner arm 128 about a third pitch joint, which provides further ability to adjust its angle forward and backward. The third positioner arm 128 terminates at surgical arms 16 with a second roll joint, which allow for rotation of the respective surgical arms 16. The surgical arms 16 may be attached to the free end of the positioner 124 by respective swivel mounts. Similar to other surgical arms 16, the system 120 may include left and right surgical arms 16, which each allow for movement with seven degrees of freedom (7 DoF), namely, roll×pitch×roll×pitch×roll×pitch×roll. The positioner 124 may be extended and positioned optimally in the operating room for the procedure. For example, the positioner 124 may locate the common swivel point at roughly mid-line of the OR table. The system 120 also includes a docked configuration to minimize the system's footprint.

Figure 14:
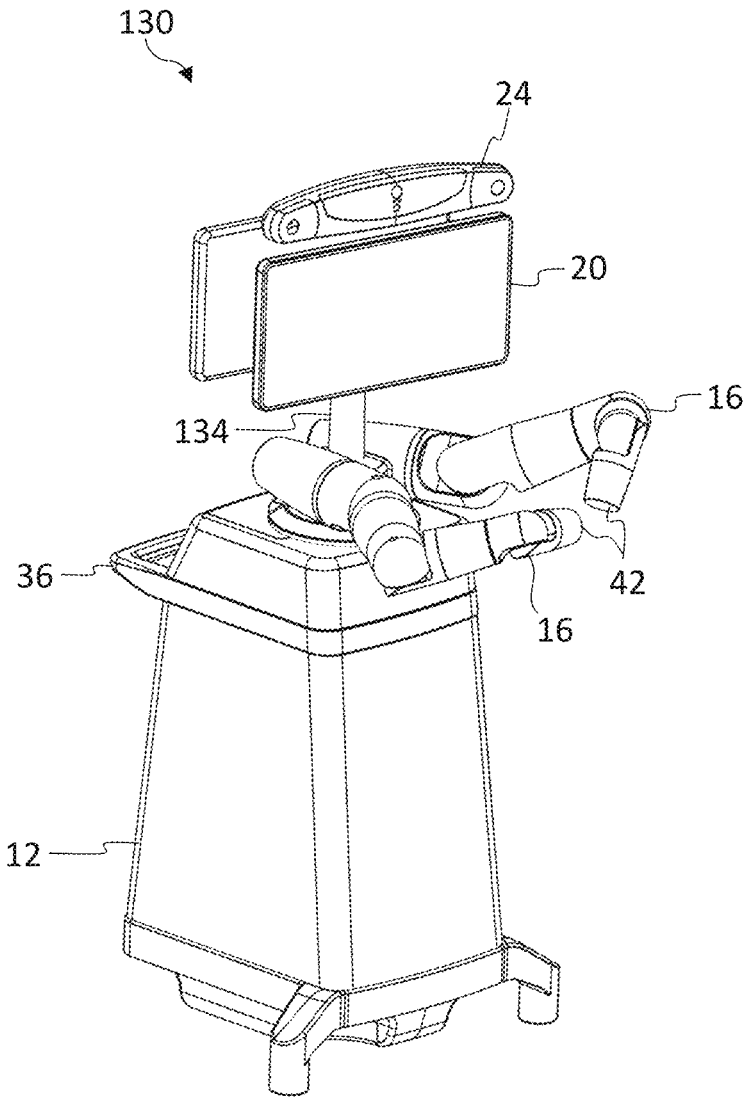
FIG. 14 shows a pedestal style robot with surgical arms starting at the base cabinet according to one embodiment.
Figure 15:
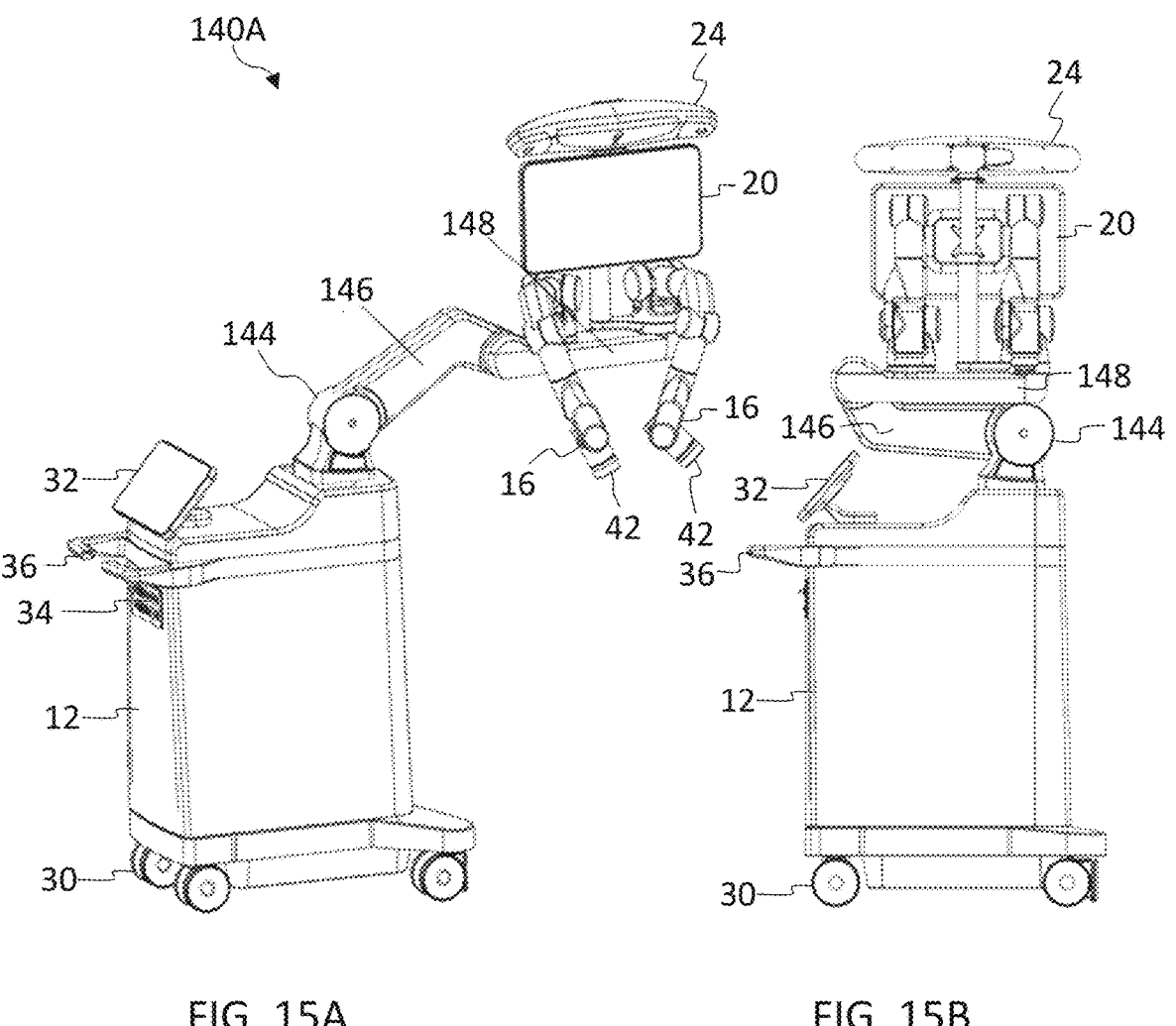
FIGS. 15A-15B show a surgical robotic system having a parallelogram positioner in extended and docked positions, respectively, according to one embodiment.

With further emphasis on FIG. 14, a multi-arm surgical robotic system 130 is shown according to one embodiment. Robot system 130 is a pedestal-style robot with dual surgical arms 16 starting at the base cabinet 12. The dual-arm pedestal robot may only include a single degree of freedom. For example, a vertical arm positioner 134 may include a swivel mount to the base cabinet 12 to provide for one degree of freedom (1 DoF). The swivel mount may allow for rotational movement around the axis of the vertical arm 134. As shown, the monitors 20 may be positioned back-to-back on the top of the vertical arm 134, such that an assistant may view the procedure from outside the surgical space. The camera 24 may be located above the monitors 20. The swivel positioner 134 may be common to both surgical arms 16. Similar to other surgical arms 16, the system 130 may include left and right surgical arms 16, which each allow for movement with seven degrees of freedom (7 DoF). Limiting the robot's movement to one degree of freedom simplifies the design and focuses the robot's capability on its specific task(s).

With further emphasis on FIGS. 15A-15B, a multi-arm surgical robotic system 140A is shown according to one embodiment. In robot system 140A, the arm positioner 144 includes a parallelogram positioner configured to extend the surgical arms 16 into the surgical space. The parallelogram positioner 144 includes a first positioner link 146 and a second positioner link 148, which supports the surgical arms 16. The first positioner link 146 may be a one axis positioner where both pitch joints are tied together with a timing belt or chain, thereby synchronizing movement of the pitch joints. The second positioner link 148 may be always parallel to the ground with the mechanism controlled by a single motor. The parallelogram linkage ensures that as the mechanism articulates, the second positioner link 148 remains parallel to the ground. The use of a single motor simplifies the control system and may improve reliability and reduce maintenance needs. Alternatively, both positioner joints may be decoupled and controlled by independent motors, allowing for the second positioner link 148 to achieve arbitrary angles relative to ground. When in use, the positioner 144 may locate both of the surgical arms 16 roughly midline of the OR table. Similar to other surgical arms 16, the system 140A may include left and right surgical arms 16, which each allow for movement with seven degrees of freedom (7 DoF). The surgical arms 16 may be located on top of the second positioner link 148. The monitor 20 and camera 24 may also be mounted to the second positioner link 148, and positioned above the surgical arms 16. Similar to system 10, the multi-arm surgical robotic system 140A may have deployed and docked system configurations. FIG. 15A shows the surgical robotic system 140A in a deployed position, and FIG. 15B shows the surgical robotic system 140A in a compact docked position.

Figure 16:
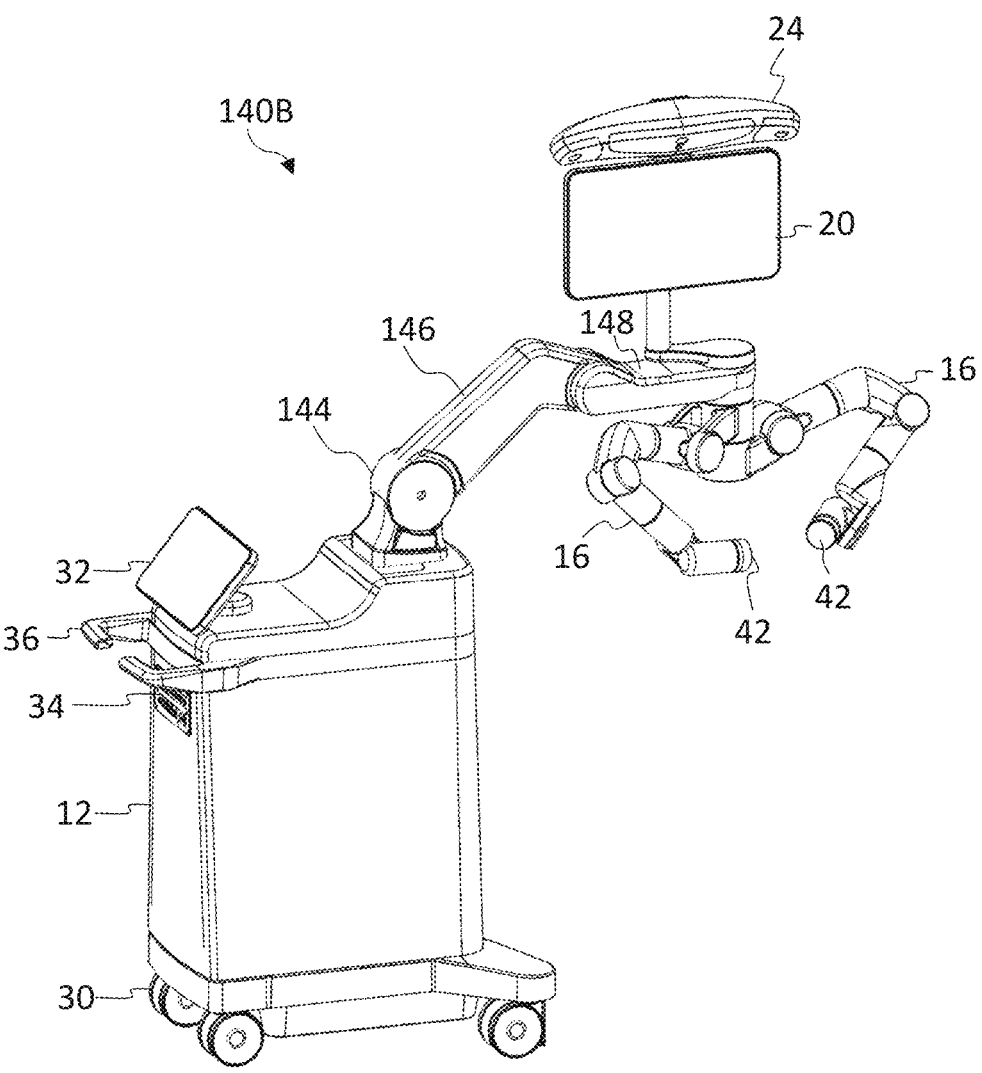
FIG. 16 shows a surgical robotic system having a parallelogram positioner with a floating column according to one embodiment.

With further emphasis on FIG. 16, a multi-arm surgical robotic system 140B is shown according to one embodiment. Robotic system 140B is similar to system 140A except the surgical arms 16 are attached beneath the second positioner link 148, such that the arms 16 dangle downward. The monitor 20 and camera 24 may still be mounted to the top of the second positioner link 148. In this embodiment, the surgical arms 16 are mounted from a bottom of the second positioner link 148, with first links of each surgical arm 16 mounted in series forming a hanging column. The parallelogram positioner 144 acts as an overhead support for the pair of surgical arms 16. During the procedure, the positioner 144 is configured to locate the two 7 DoF surgical arms 16 roughly midline of the OR table. This allows the surgical arms 16 to hang over the workspace without obstructing the area below, thereby maximizing spatial efficiency. The parallelogram configuration also allows for compact docking of the system 140B.

Figures 17A, 17B:
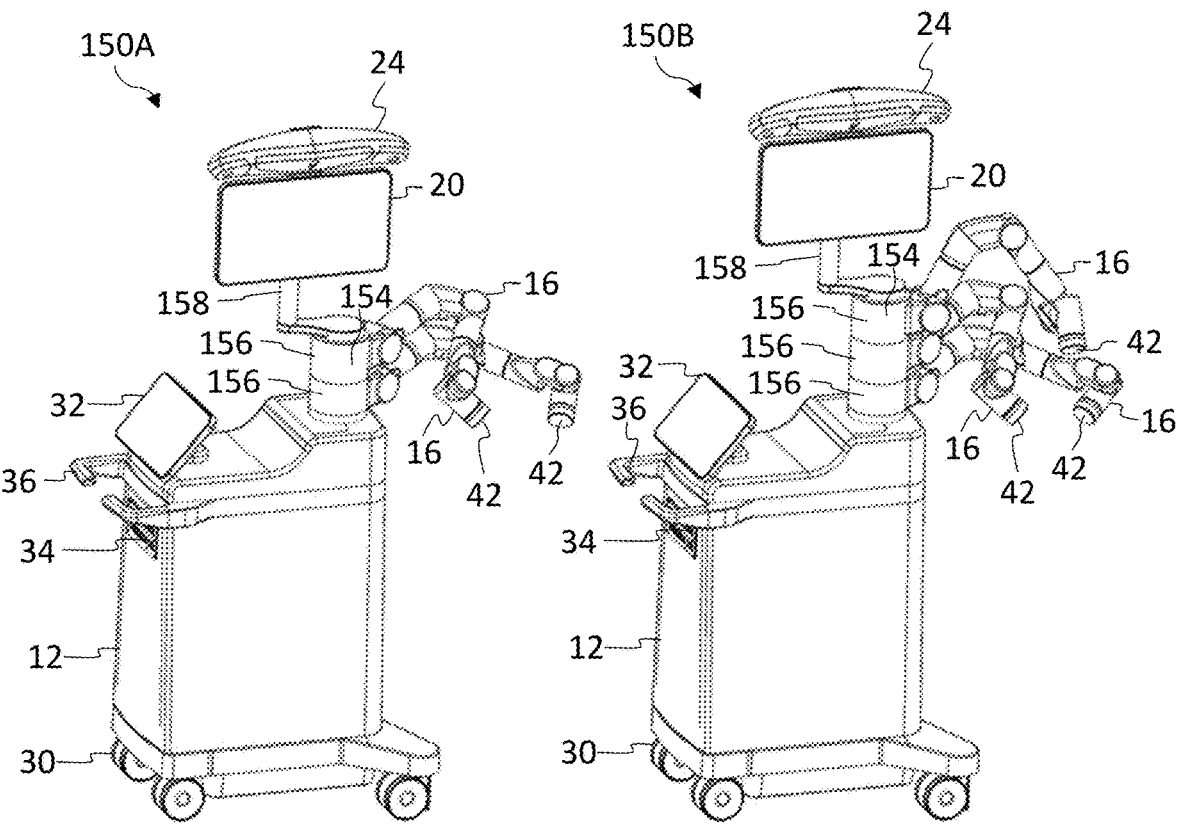
FIGS. 17A-17B show examples of a stacked column with two surgical arms and three surgical arms, respectively.

With further emphasis on FIGS. 17A-17B, multi-arm surgical robotic systems 150A, 150B are shown in accordance with further embodiments. In these embodiments, the surgical arms 16 may be mounted directly to the base 12 without a positioner, thereby forming a stacked column 154. The first link 156 of each surgical arm 16 may be mounted in series on the base 12, forming the column shape. The first link 156 of each arm 16 may define a revolute or rotary joint, which permits rotation about a single axis. The links 156 may be coaxial such that all links 156 rotate about the same vertical axis. Similar to other surgical arms 16, the systems 150A, 150B may provide surgical arms 16 having movement with seven degrees of freedom (7 DoF). The surgical arms 16 may extend laterally from the first links 156. FIG. 17A shows system 150A with two stacked links 156 supporting two surgical arms 16, and FIG. 17B shows system 150B with three stacked links 156 supporting three surgical arms 16. The stacked links 156 may have an "n" number of surgical arms 16 by stacking more arms 16 vertically, thereby increasing the overall column height. The monitor 20 and camera 24 may be mounted to the top of the stacked arm column 154, for example, with one or more positioners 158. The positioners 158 may include any suitable joints for positioning the monitor 20 and camera 24, which may be offset relative to the axis of the stacked column 154. Similar to the other systems, the multi-arm surgical robotic systems 150A, 150B may have deployed and docked system configurations.

Turning now to FIGS. 18-21D, distributed systems may be provided such that the main system components (surgical arms, navigation camera, and surgeon displays) are decoupled, either fully or into different subset permutations. For the fully decoupled option, each element may be positioned to optimize its own individual task. Specifically, the surgical arm(s) 16 may be arranged to be on their own mobile platform. The precise number of surgical arms 16 needed for a given portion of the surgery may dynamically adjust, either by positioning additional surgical arms 16, or by removing excess surgical arms 16. A separate viewing station with one or more monitors 20 may be positioned for surgeon use or external monitors in the OR suite may receive the video out signal from the system. The navigation camera 24 may also be positioned for optimal line of sight. In one embodiment, a subset system may be arranged to have the surgical arm(s) 16 decoupled while used in concert with a separate full navigation and control system. In another embodiment, a subset system may integrate the surgical arm(s) 16 into a full navigation and control system while the camera is separate from the system for line-of-sight optimization. It will be appreciated that different components may be coupled together or decoupled to optimize the outcome.

Figure 18:
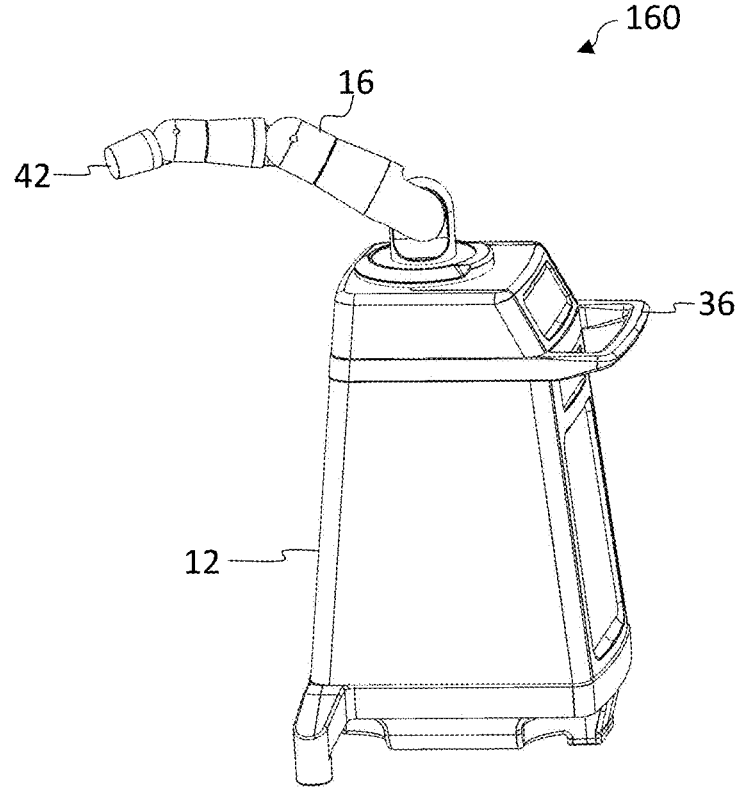
FIG. 18 shows a surgical robotic system having a stand-alone pedestal arm according to one embodiment.

With further emphasis on FIG. 18, a stand-alone pedestal arm system 160 is shown according to one embodiment. In this embodiment, a single surgical arm 16 is attached to the top of the base 12. The surgical arm 16 may be attached to the base 12, for example, with a swivel mount to allow for rotational movement of the arm 16 about the base 12. The surgical arm 16 may work alone or in concert with another stand-alone pedestal arm system 160 or other system. As shown, the navigation camera 24 and surgeon displays 20, 32 are absent from this decoupled system 160. Accordingly, additional stations with these components may be combined to complete the distributed system.

Figure 19:
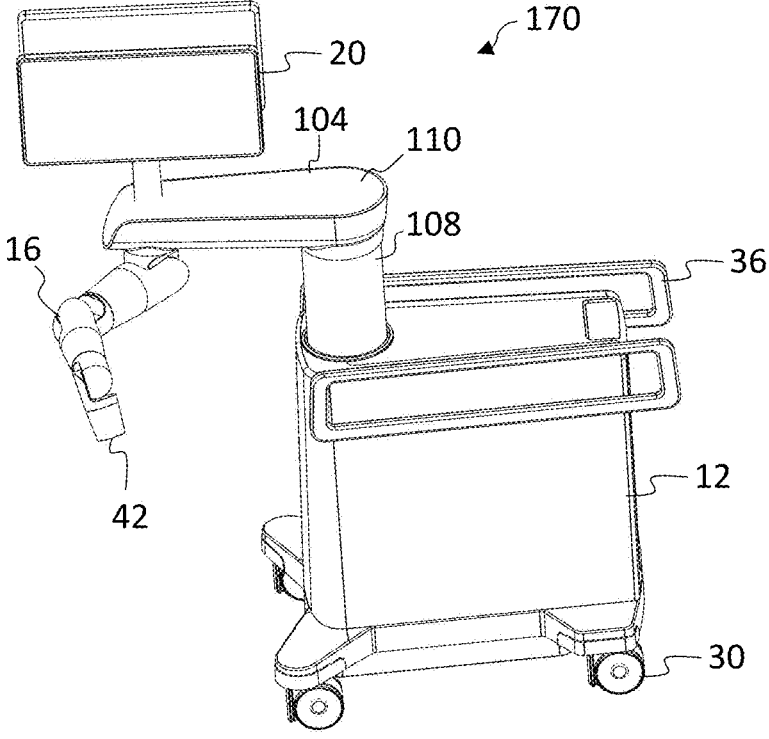
FIG. 19 shows a surgical robotic system having a decoupled surgical arm having ten degrees of freedom according to one embodiment.

With further emphasis on FIG. 19, a distributed subsystem 170 is shown according to one embodiment. Subsystem 170 is similar to system 100A except sub-system 170 has only a single surgical arm 16 and the navigation camera 24 is omitted from the system 170. The single surgical arm 16 may be used alone or may be combined with another armed robotic system. The navigation camera 24 may be supplied on a separate stand, permanently mounted in the operating room, or otherwise provided in another robotic or navigation system to provide the optimal line of sight.

Figure 20:
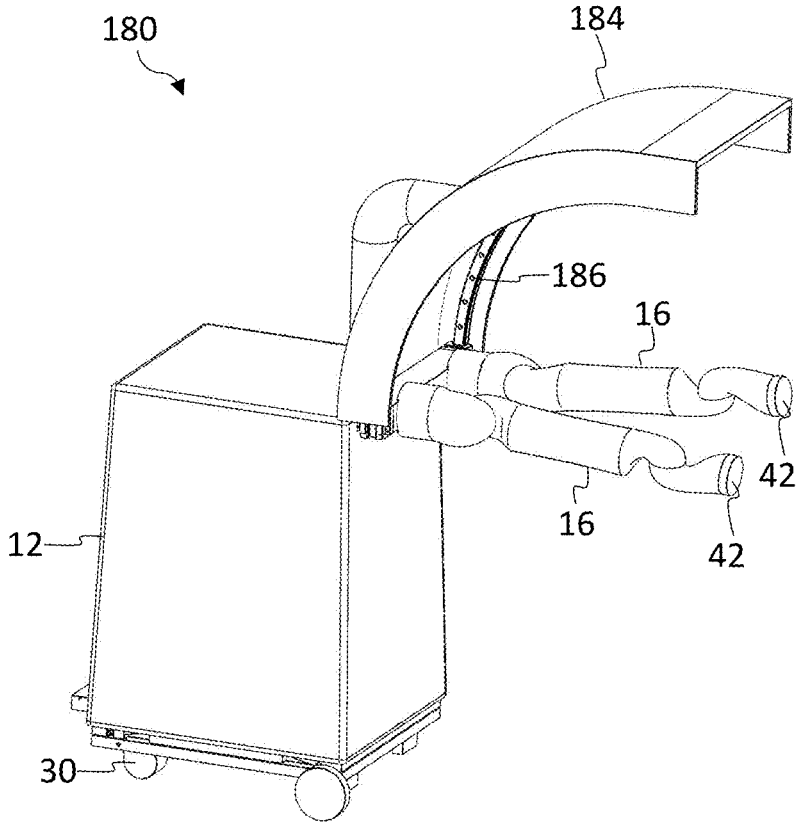
FIG. 20 shows a surgical robotic system with a curvilinear gantry to position dual surgical arms about the patient according to one embodiment.

With further emphasis on FIG. 20, a dual-arm sub-system 180 is shown according to one embodiment. The dual-arm sub-system 180 may utilize a curvilinear arm positioner 184, such as a C-shaped gantry, for positioning the surgical arms 16. Similar to other surgical arms 16, the sub-system 180 may include a pair of surgical arms 16, which each allow for movement with seven degrees of freedom (7 DoF). In this embodiment, the arm positioner 184 may curve or bend along a non-linear path. The arm positioner 184 may include one or more curvilinear tracks 186 configured to position the surgical arms 16 about the patient. A pair of parallel curved tracks 186 may be offset to guide each of the respective arms 16. Alternatively, the tracks 186 may take different pathways to guide the arms 16 to different positions. In the embodiment shown, the tracks 186 allow the attached surgical arms 16 to move along the semi-circular or open curve of the curvilinear arm positioner 184. The center of rotation for the arm positioner 184 may be roughly co-axial with the long axis of the OR table, providing a large, clinically relevant working volume with a relatively simple mechanism.

Figures 21A, 21B, 21C, 21D:
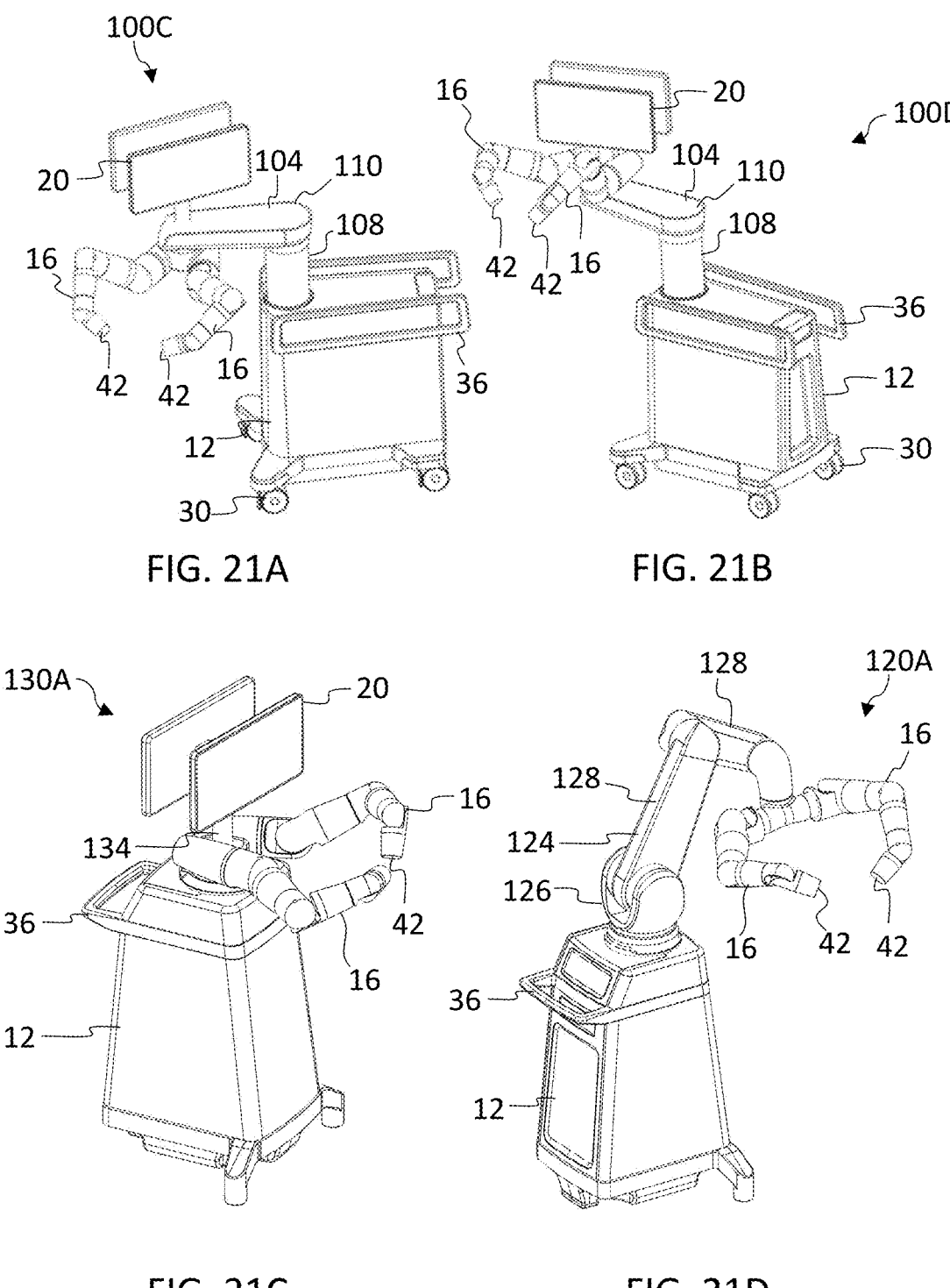
FIGS. 21A-21D show examples of the decoupled single cart systems without a camera.

With further emphasis on FIGS. 21A-21D, multi-arm surgical robotic sub-systems 100C, 100D, 130A, 120A are shown in accordance with further embodiments. Each of these sub-systems are provided without a navigation camera 24. FIG. 21A shows multi-arm surgical robotic sub-system 100C, which is the same as multi-arm robotic system 100A with the navigation camera 24 omitted. FIG. 21B shows multi-arm surgical robotic sub-system 100D, which is the same as multi-arm robotic system 100B without the navigation camera 24. FIG. 21C shows multi-arm surgical robotic sub-system 130A, which is the same as multi-arm robotic system 130 with the navigation camera 24 omitted. FIG. 21D shows multi-arm surgical robotic sub-system 120A, which is the same as multi-arm robotic system 120 with the monitor 20 and navigation camera 24 omitted. The navigation camera 24 may be supplied on a separate stand, permanently mounted in the operating room, or otherwise provided in another robotic or navigation system to provide the optimal line of sight. When needed, the surgeon display(s) 20 may be provided on a separate viewing station, wireless tablet, or other external monitor. The distributed sub-systems may be combined in any suitable combinations to optimize the surgical procedures. It is further envisioned that any of the system, sub-systems, or components described herein may have a permanent installation. For example, one or more surgical arms 16 may be integrated and mounted into the OR ceiling or floor or integrated into the OR table.

Smart Arm Positioning

The multi-arm surgical robotic system 10 may be configured with advanced and automated adjustment of the surgical arm(s) 16, the monitor arm 18, and/or the camera arm 22. Smart positioning may allow the arms 16, 18, 22 to automatically adjust to predefined positions or proactive adjustment. For example, the surgical arms 16 may automatically adjust for optimal access to the surgical site, collision avoidance, and/or ergonomic support. The monitor arm 18 may be automated for optimal viewing positions or synchronization with surgical phases. The camera arm 22 may be automatically adjusted for optimal viewing angles at various stages of the procedure.

Figure 22:
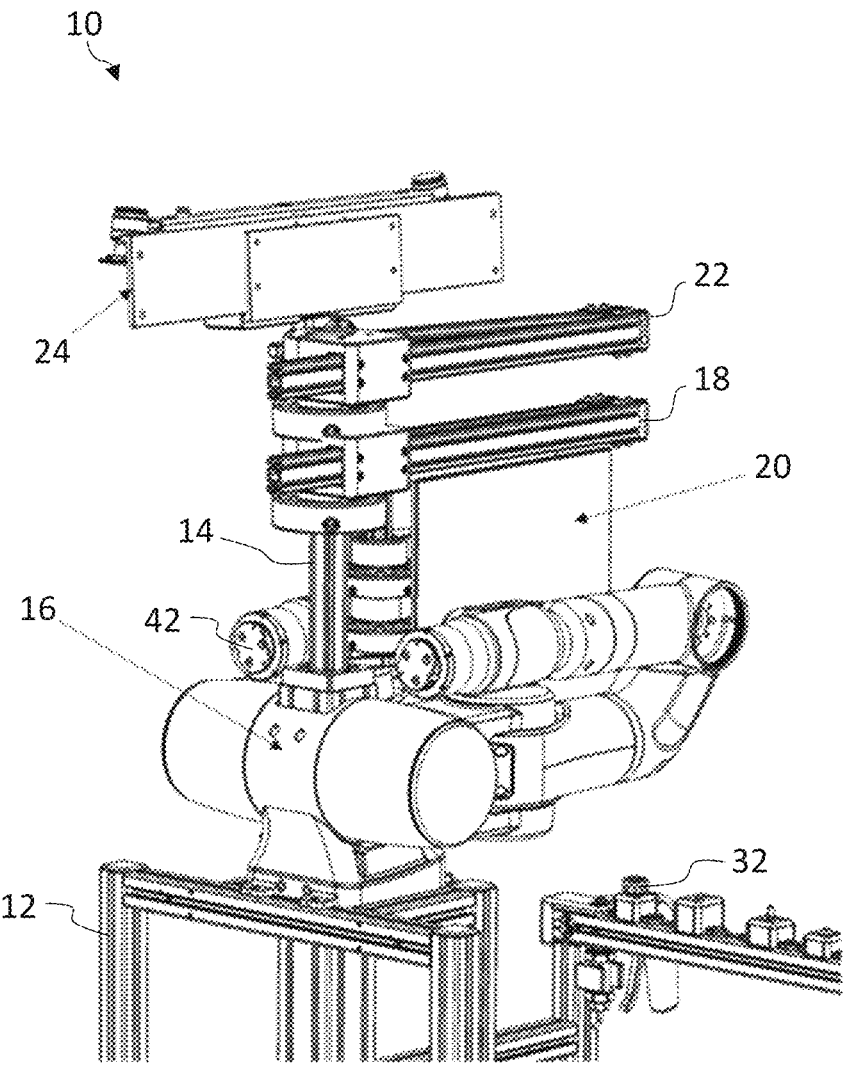
FIG. 22 shows a surgical robotic system in a docked position ready for setup.
Figure 23A:
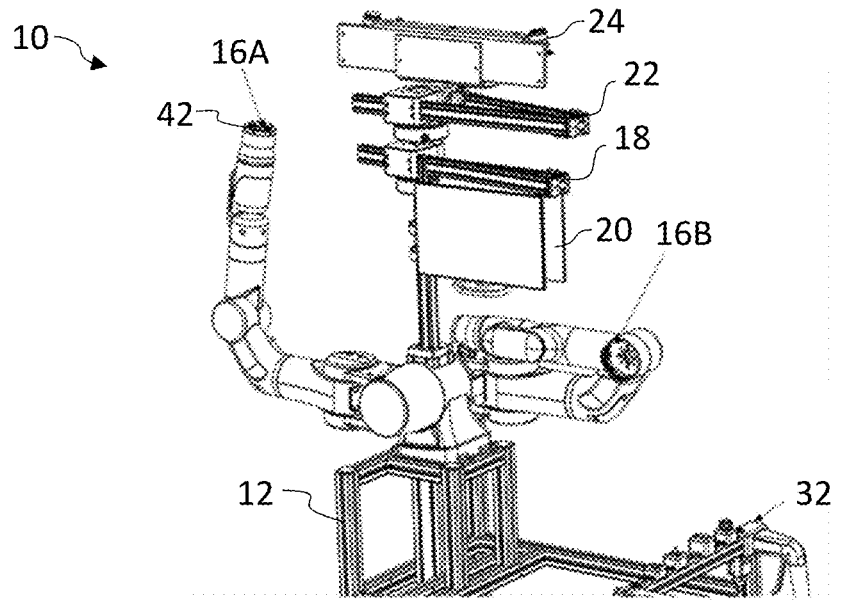
FIGS. 23A-23B show examples of pre-set positions for draping the robot in single arm and multi-arm procedures, respectively.
Figure 23B:
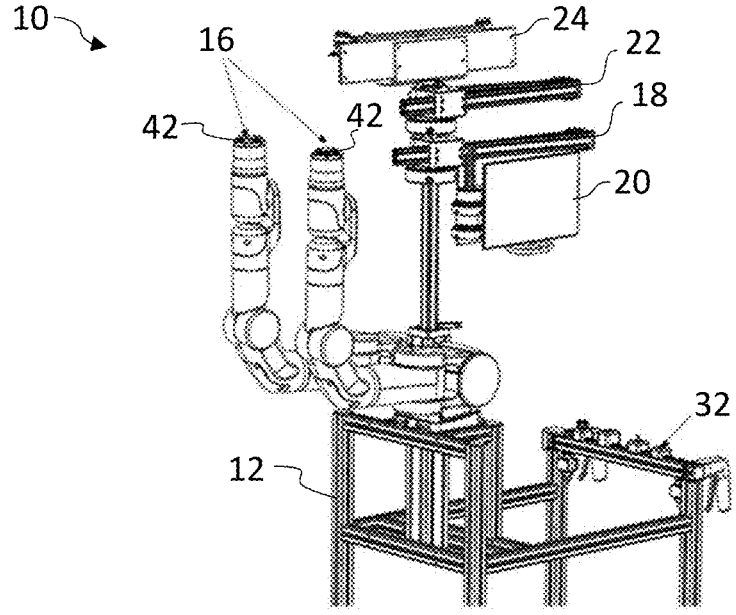

Turning now to FIGS. 22 and 23A-23B, examples of predefined draping techniques are shown. Surgical draping is a safety operation to ensure sterility of the surgical field. The operation is often complex due to both the geometry being draped and the drape itself. The process requires sterile and non-sterile personnel to execute. The surgical robotic platform 10 may leverage the dexterity of the surgical arm(s) 16 to facilitate draping along with embedded control at the non-sterile terminal 32. In this embodiment, the surgical arms 16 may be draped in the same manner as a surgeon donning a gown and gloves. FIG. 22 shows the surgical robotic system 10 in the docked position, which is how the system 10 may enter the operating theater for subsequent setup.

Once in position in the surgical space, the system 10 may be deployed for surgical draping. From the non-sterile display or terminal 32, a technician or assistant may deploy the system 10 for draping, for example, with a simple press of a button. The surgical arm(s) 16 may move to a pre-set draping position, for example, as shown in FIGS. 23A-23B, mimicking a surgeon position for gown and gloves. FIG. 23A shows draping for a single arm procedure where a single arm 16A is extended upward for draping and the additional arm(s) 16B remain docked. FIG. 23B shows draping for a multi-arm procedure, in this case, where both surgical arms 16 are extended vertically upward for draping. For example, the arm(s) 16 may bend at an elbow and then extend straight upwards with the arms 16 aligned in parallel. From this position, a sterile technician may apply the surgical drape to the arm(s) 16. The position of the arm(s) 16 facilitates in-process stability of the drape, preventing the drape from falling onto the floor and compromising sterility. From this point, a non-sterile technician may finish drape installation onto the rear of the system 10. If the procedure at-hand requires a single arm 16, the non-utilized arms 16 may remain un-draped and in the docked position as shown in FIG. 23A. The pre-set posture allows for easy and sterile application of the drape ensuring that the drape envelops the system 10 without contaminating the sterile field.

Similarly, the monitor and camera arms 18, 22 may deploy to a draping position with the simple press of a button. The system 10 may provide guidance on the steps the user should take to drape each element, while accommodating flexibility if the case only calls for a sub-set of robotic arms 16 to be used. Because all four arms 16, 18, 22 are robotically controlled, the system 10 has knowledge of each arm position and can ensure there are no collisions between arms, or movements that would compromise sterility of the newly draped arms.

The draping strategy of mimicking the orientation of a surgeon during draping greatly facilitates the application of the drape to the sterile portion of the robot 10. It also reduces the amount of people required to complete draping which streamlines setup. The vertical position of the arm(s) 16 maintains the in-process stability of drape so it cannot fall off of the arm(s) 16 before a non-sterile tech is able to finish securing the drape to the rear of the system 10. The ability to deploy a single arm 16, or any number of arms 16 to complete a procedure represents an efficiency for the hospital by way of avoiding the time and cost associated with draping non-utilized components. The ability for additional arms 16 to remain out of the field during procedures also makes the most efficient use of space in an environment where space is at a premium.

Figure 24A:
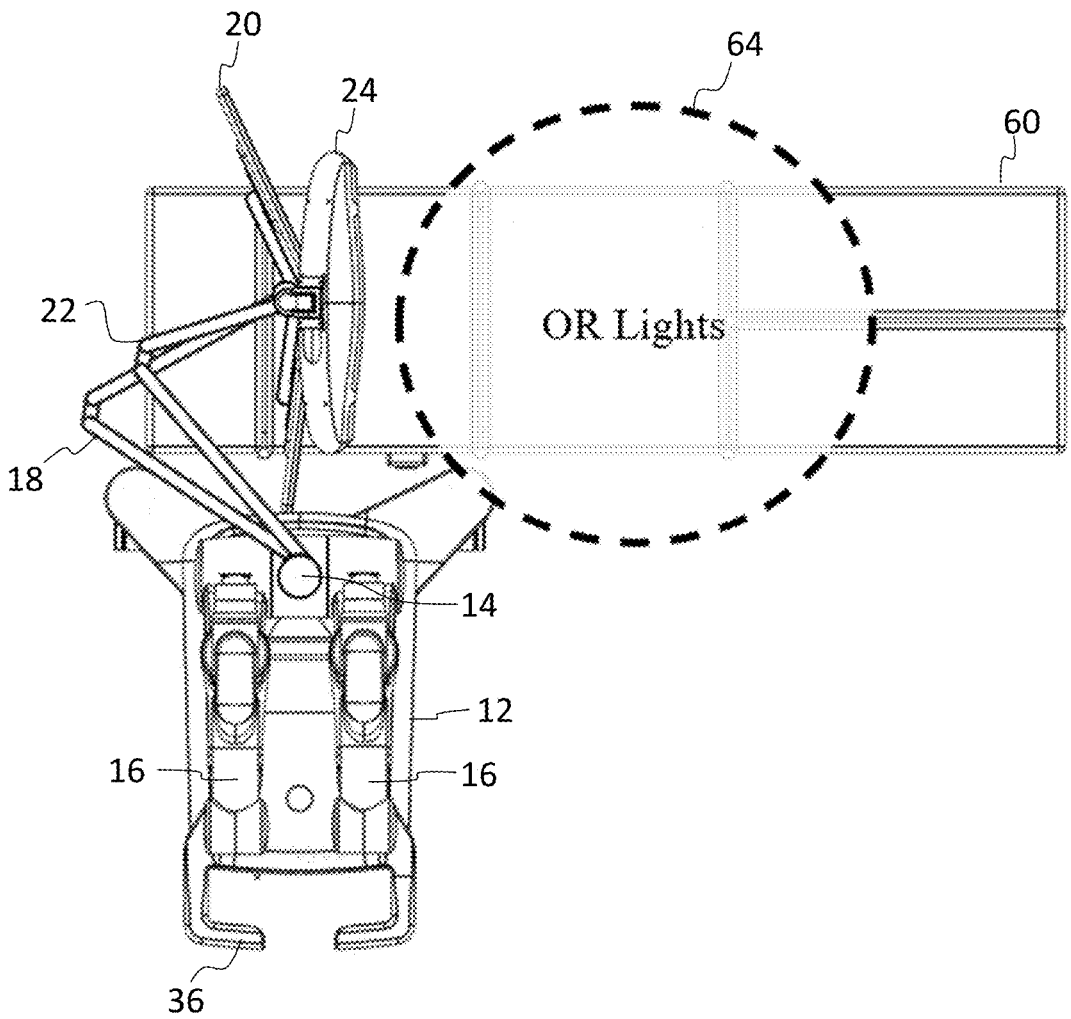
FIGS. 24A-24B show examples of arrangements for positioning the navigation camera for optimal line of sight while avoiding operating room lights.
Figure 24B:
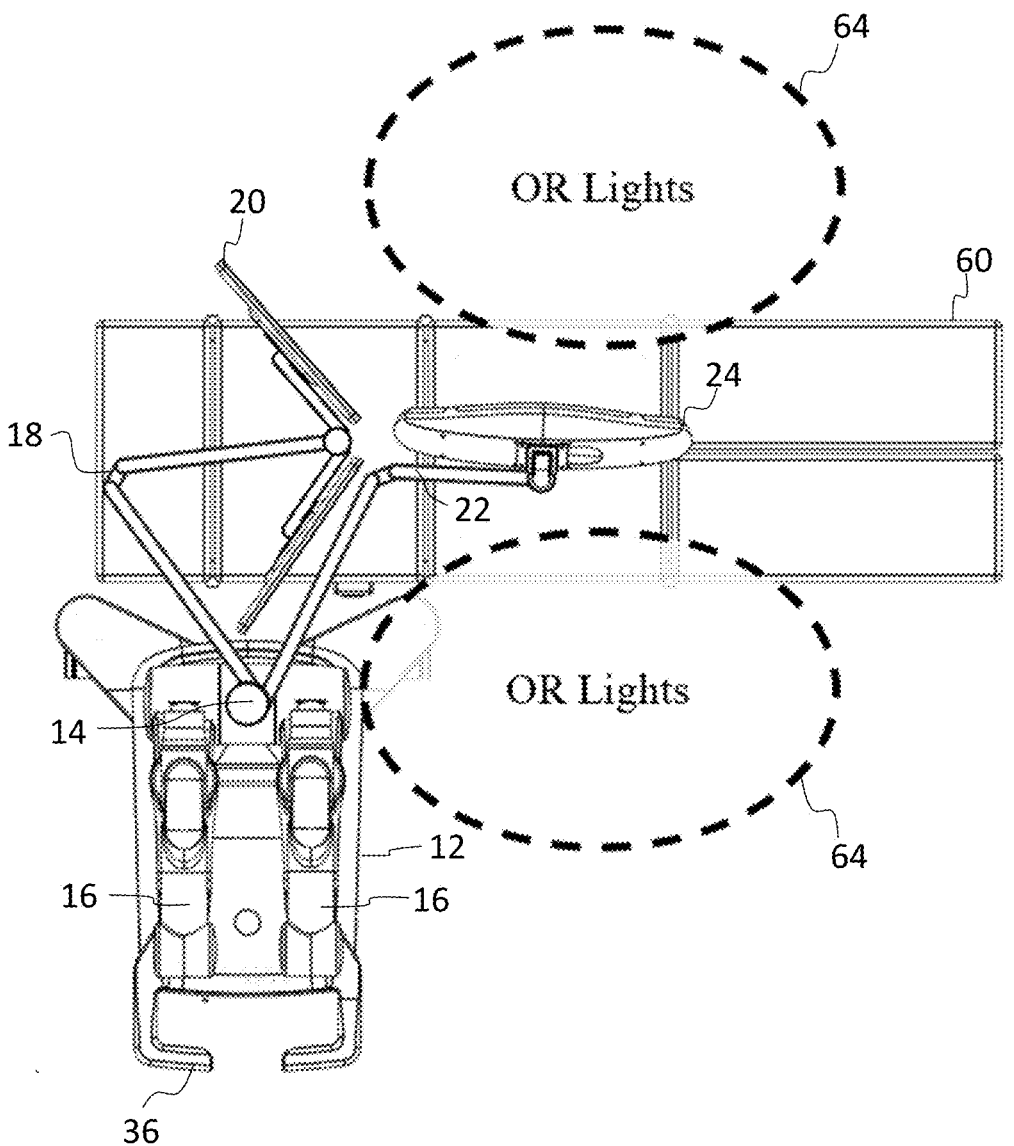

Turning now to FIGS. 24A-24B, examples for positioning the navigation camera 24 with optimal line of sight while avoiding operating room lights 64 are shown. The camera arm 22 is configured to position the camera 24 above the OR table 60 and track the procedure from top-down. This vantage point provides a direct field of view to the surgical site, and minimizes occlusions from staff or equipment in the operating room. A challenge with this tracking approach is ensuring that the camera 24 does not interfere with the OR lights 64 above the table 60 while still achieving the necessary line of sight. The arm arrangement may allow the camera 24 to avoid the OR light's illumination space either by placing the camera 24 adjacent to the OR lights 64 (as shown in FIG. 24A), or between the OR lights 64, if there are two sets of lights at the table 60 (as shown in FIG. 24B). In all cases, positioning the camera 24 above the patient table 60 ensure optimal line of sight to capture a clear, unobstructed view of the operating area.

The motorized camera positioning arm 20 may be configured to dynamically and automatically optimize tracking throughout the procedure. Because the camera position control is integrated with the procedural application, the system 10 knows the full set of objects to be tracked during the procedure. The system 10 anticipates when objects enter and exit the scene as the procedure progresses, and knows the hierarchy of importance for given objects in the scene depending on the procedural step. With this contextual knowledge, the system 10 can track all objects of interest in the scene, and center the field of view on the relevant objects by physically moving the camera 24. Centering the field of view may be performed on request from the user, on an automated-periodic basis, or on a fully continuous basis.

In addition, the camera positioner 14, 22 may use full system kinematics and procedural context to predict when the monitors 20 and surgical arms 16 may be in the camera's field of view. The camera 24 may be actively positioned to minimize self-occlusions from the monitors 20 or surgical arms 16, while optimizing the scene for tracked objects.

One step that often requires large camera manipulations is intra-operative image registration. A fluoroscopy or computer tomography fluoroscopy (CT) image may be taken while both the patient and the imaging system are tracked as a preliminary step to enable navigation. In practice, this requires that the camera 24 must be moved from its position centered on the surgical site to a position where both the patient tracking reference and the tracking array on the imaging equipment are in field of view. After the registration is complete, the camera 24 is moved back to a position centered on the surgical site. With the motorized robotic camera positioner 14, 22, this whole process may be automated, including the large-scale motions and the field of view centering and optimization.

Camera positioning may be controlled by the user, for example, via one of the touchscreen displays 20. Camera positioning may also be controlled from the non-sterile user terminal 32 at the rear of the system 10. The camera view may be directly displayed at the monitor or control panel 20, 32 where a user can visually aim the camera 24 at the region of interest via touch screen control or jogging discrete buttons, for example. Automated and improved navigation continuity provides enhanced navigation and frees the user from tedious camera adjustments. For the user experience, the navigation camera 24 begins to fade into the background and the technology blends into a comfortable workflow focusing on the procedure, not the system, which is a large step toward removing the art of navigation.

Figure 25A:
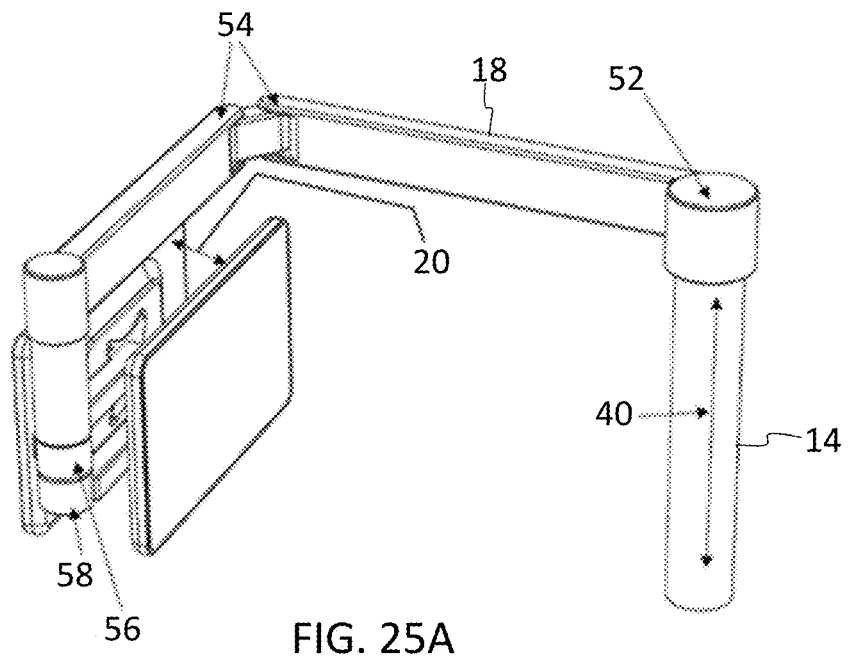
FIGS. 25A-25B show examples of positioning the dual-display monitors with opposing displays and side-by-side displays, respectively.
Figure 25B:
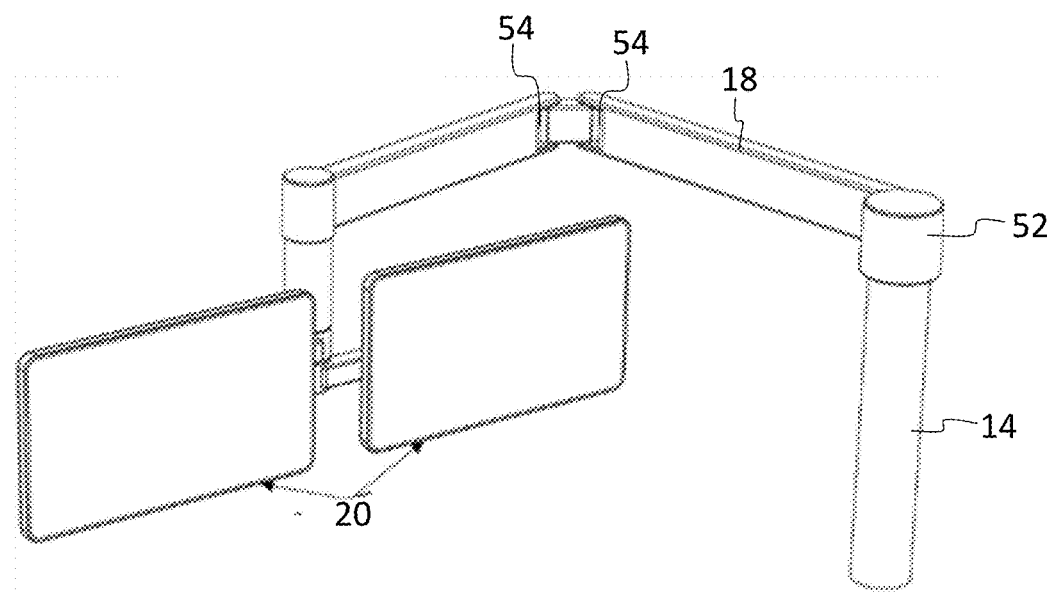
Figure 26:
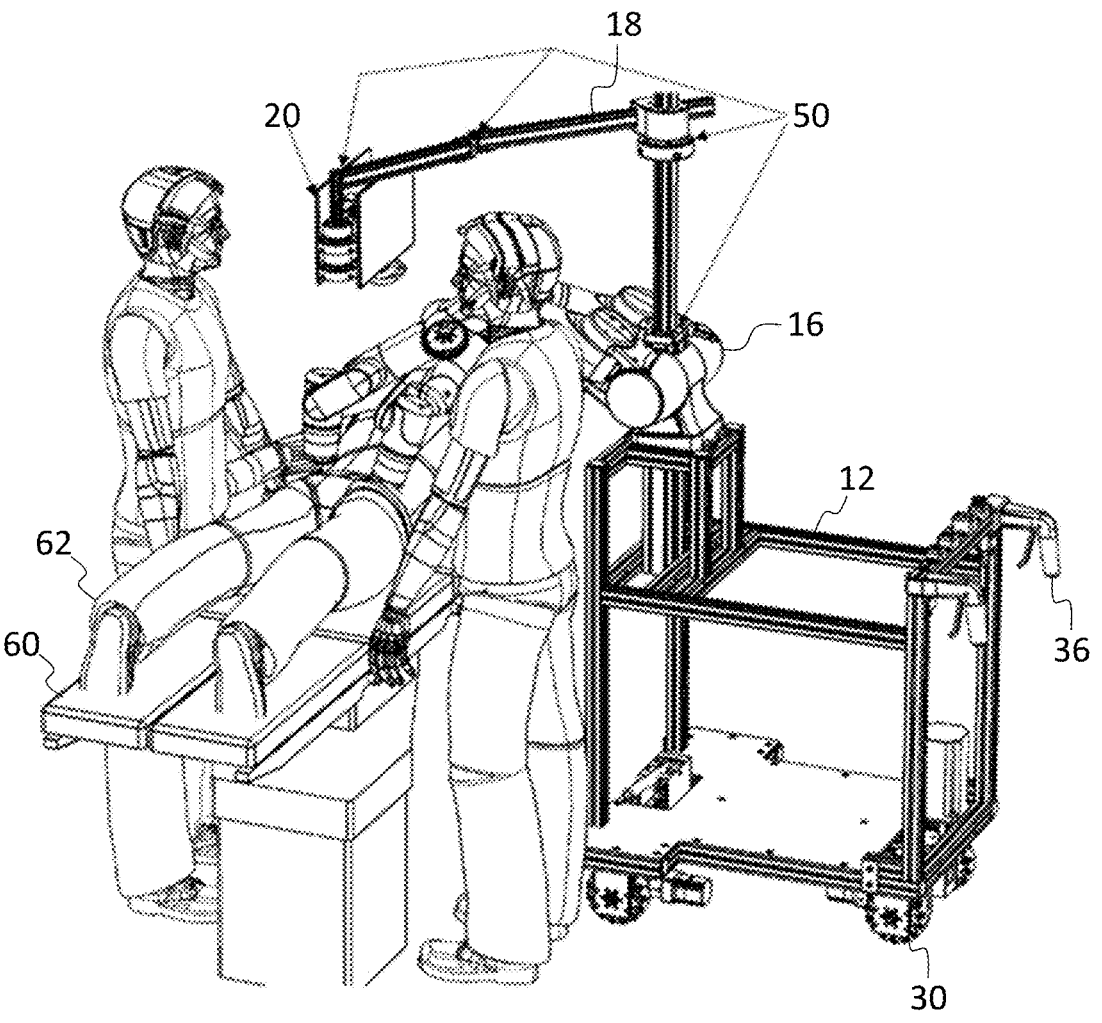
FIG. 26 shows one example of fully opposed displays with multiple surgeons working on opposite sides of the operating room table.

Turning now to FIGS. 25A-25B and 26, one or more intelligent monitors 20 may be used to improve visibility by one or more users of the system 10. Dual intelligent displays 20 allow for visibility of workflow, tracking, and system status from one or both sides of the operating table 60. The displays 20 may be mounted on a highly capable arm 14, 18, which enables extended reach and highly dexterous positioning. The display arm architecture may include numerous joints 50, such as duplex hinges 54 and rotary joints 52, 56, 58. A rotary joint 52 may connect the arm 18 to the vertical positioner 14. The duplex hinges 54 allow the displays 20 to be positioned in the surgeon's location-of-preference. The display-specific concentric rotary joints 56, 58 may control the angular positioning of each display 18 relative to one another. A first display rotary joint 56 may couple one display 20 to the free end of arm 18, and a second display rotary joint 58 may couple the other display 20 to the free end of arm 18. For example, as shown in FIG. 25A, the display pose may include fully opposed displays 20, and in FIG. 25B, the display pose may include adjacent displays 20 in butterfly mode. It will be appreciated that positioning between the displays 20 may be possible at any angle between 0° and 180°.

As shown in FIG. 26, fully opposed displays 20 may be useful when multiple surgeons are working simultaneously on both sides of the operating room table 60. Butterfly mode offers an enhanced user interface for single-surgeon procedures by making both screens 20 available for use and reference by the surgeon. The dual displays 20 may be mounted to a bimodal active/passive arm with encoded, motorized joints so that arm position is known to the system 10 at all times. Specifically, all joints may use absolute, single-turn encoders allowing the system 10 to know arm position immediately on system power-up without need for a homing routine. This allows a unique opportunity for intelligent positioning of the displays 20 to coordinate with the portion of the procedure being executed. The system 10 may have preset and customizable configurations for the monitor arm 18 such that the displays 20 can move toward the surgeon during planning and review, and away during navigation so that viewing is always optimal and ergonomic. If the surgeon has a given preference for a different display position, the position can be manually manipulated to the preferred orientation while maintaining position tracking for future automated moves.

From a user experience, dual monitors 20 represent an improved workflow efficiency. The dual monitors 20 allow a single surgeon to have greater visibility of the procedure and workflow. It also allows multiple surgeons to utilize the robot 10 without competing for resources or compromising on visibility during navigation. The automation of display motion reduces surgeon mental load of having to continually adjust the display 20 during different portions of the procedure. The second monitor 20 also enables additional functionality, such as microscope mode.

Figure 27:
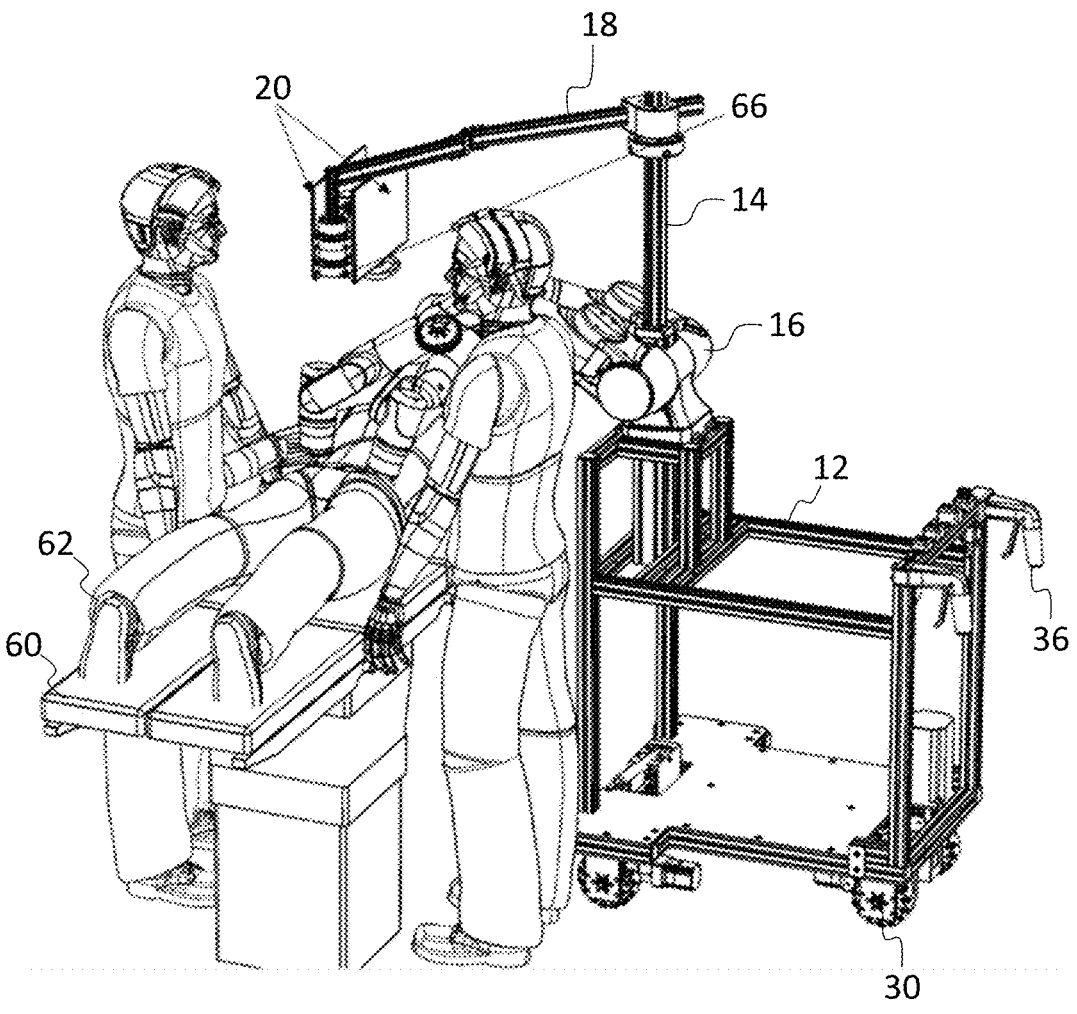
FIG. 27 shows the surgical robotic system configured with opposed displays in a microscope mode having a microscope oriented toward the surgical site for magnified visualization according to one embodiment.

Turning now to FIGS. 27-30, magnified visualization may be incorporated into the surgical robotic platform 10, emulating the function of traditional orthopedic microscopes. In this embodiment, a video feed of the magnified surgical site may be captured via one or more magnification devices 66, such as endoscopes, exoscopes, port-mounted cameras, or other cameras mounted to the robotic system 10. The magnification device 66 may provide variable magnification levels, allowing surgeons to see fine details of the surgical site, such as bone, nerves, and soft tissues, that may not be visible to the naked eye. This integrated magnification function may eliminate the need for a microscope entirely. The magnification device 66 may have integrated lighting, for example, LED-based lighting, to provide bright and focused light directly on the surgical field. The magnification device 66 may deliver high-resolution images to the surgical display(s) 20 enabling surgeons to view the surgical field with clarity. For example, a video feed may be ported to one or both of the surgical displays 20. As shown in the embodiment of FIG. 27, the displays 20 may be presented to both surgeons in the fully folded position directly at eye level, which emulates the workflow and ergonomics that surgeons are already familiar with using microscopes.

A microscope camera 66 may be mounted to the monitor arm 18, one or both of the surgical arms 16 and/or end effectors 26, or another suitable place on the robot 10. In one embodiment, a microscope camera 66 may be mounted to the underside of the monitor arm 18, leveraging the intelligent display arm 18 as both a microscope camera mounting point and positioner. The motorized arm 18 facilitates fine adjustments to the microscope camera position so that the surgeon is able to visualize and magnify the specific anatomy of interest with ease. Fine positioning controls for camera view may be located on the display or non-sterile terminal. Alternatively, the system-mounted microscope camera 66 may have the camera optics mounted to the end effector 26. The end effectors 26 may be centrally located to the surgical site and are unlikely to have an occluded line of sight. The video signal may be externally cabled, or routed internally through the robot arm primary data communication.

Figure 28:
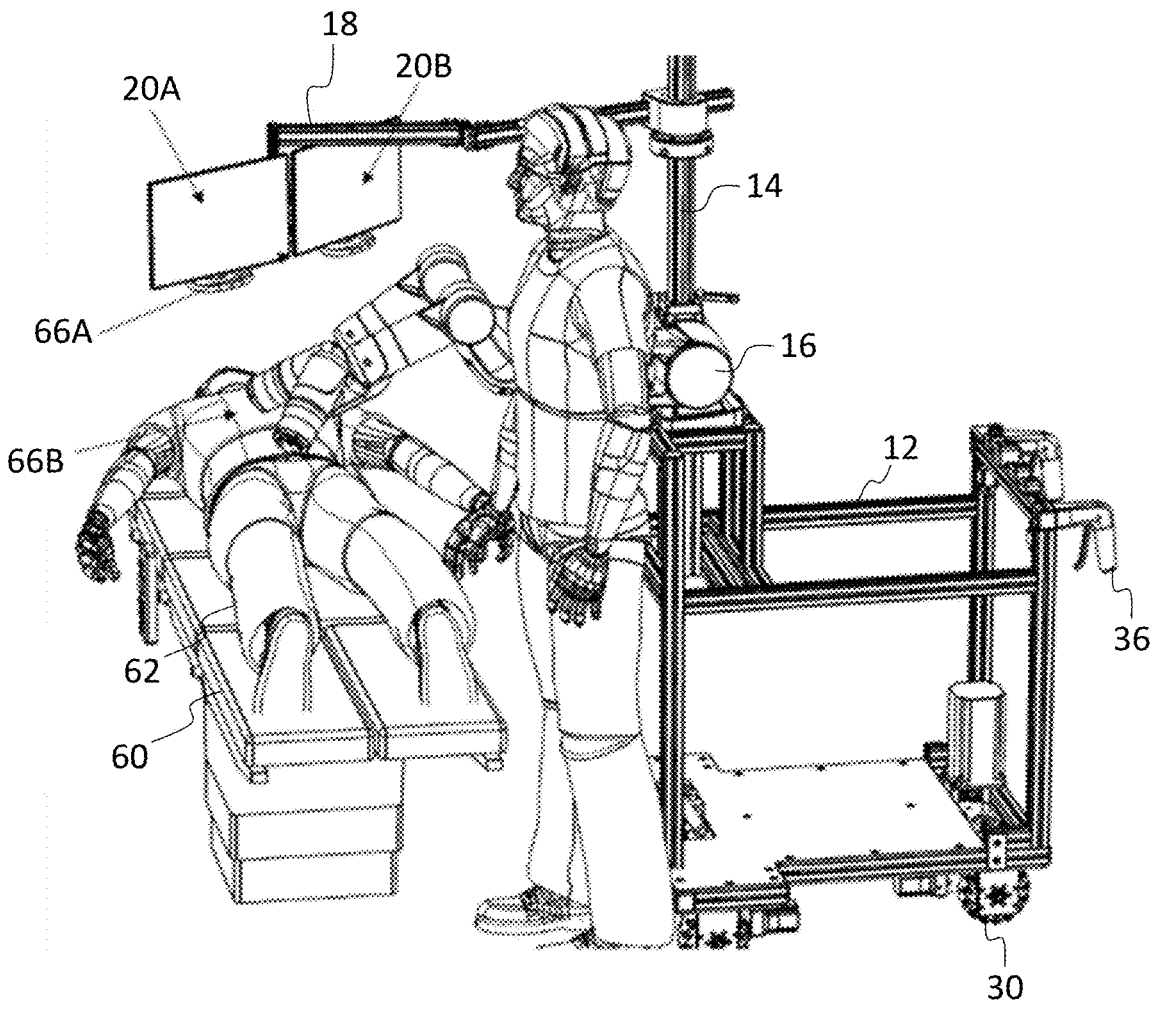
FIG. 28 shows the surgical robotic system with side-by-side displays in microscope mode allowing one display to provide the magnified image and the other display to provide the surgical workflow according to one embodiment.

Alternatively, an untethered magnification camera 66 may be mounted to another remote location. For example, the magnification camera 66 may have a spring-loaded clamping mechanism, such as a chip clip style mount, which enables quick attachment and detachment. This remote camera 66 may be secured to a table mounted arm, retractor previously installed for access, directly onto the patient, or other suitable attachment sites. For MIS cases, the magnification camera 66 may be mounted to view down into a port attached to the patient. As shown in FIG. 28, the system 10 may include downward facing magnification cameras 66A suspended beneath each monitor 20 and a clip-on magnification camera 66B on the surgical port. One monitor 20A may display the magnified camera image of the surgical site for detailed viewing and the other monitor 20B may display the surgical workflow offering a comprehensive view of the procedure's progress and steps.

Figure 29:
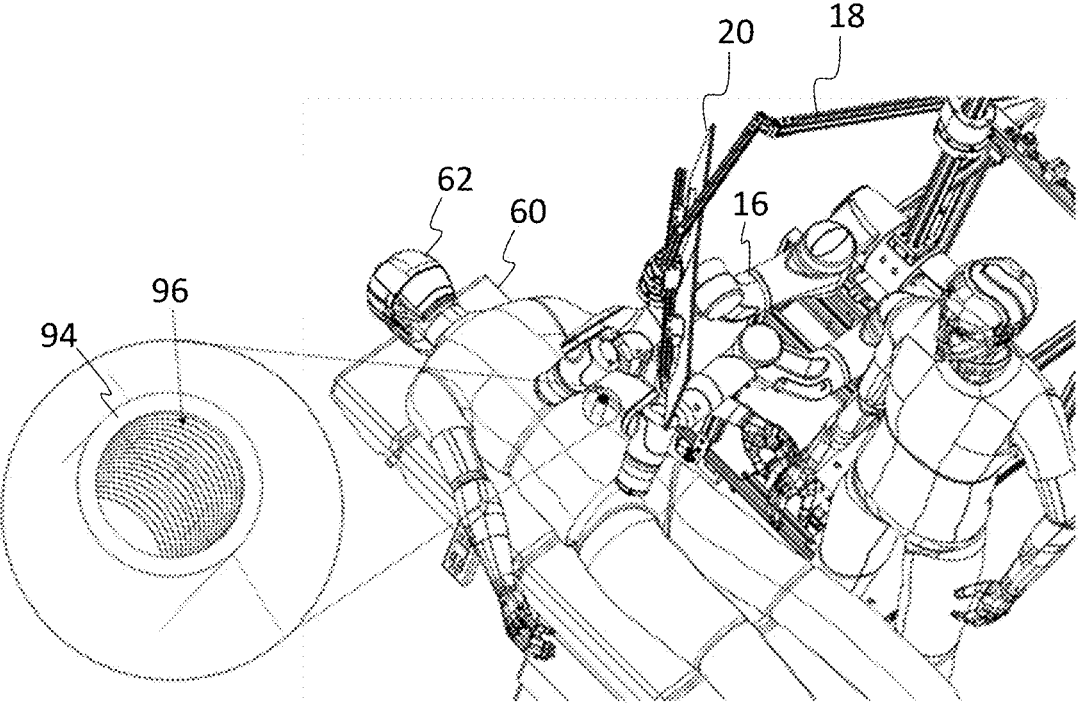
FIG. 29 shows one example of a port with fiducial markings etched into the port to assist in camera dynamic positioning and focusing.
Figure 30:
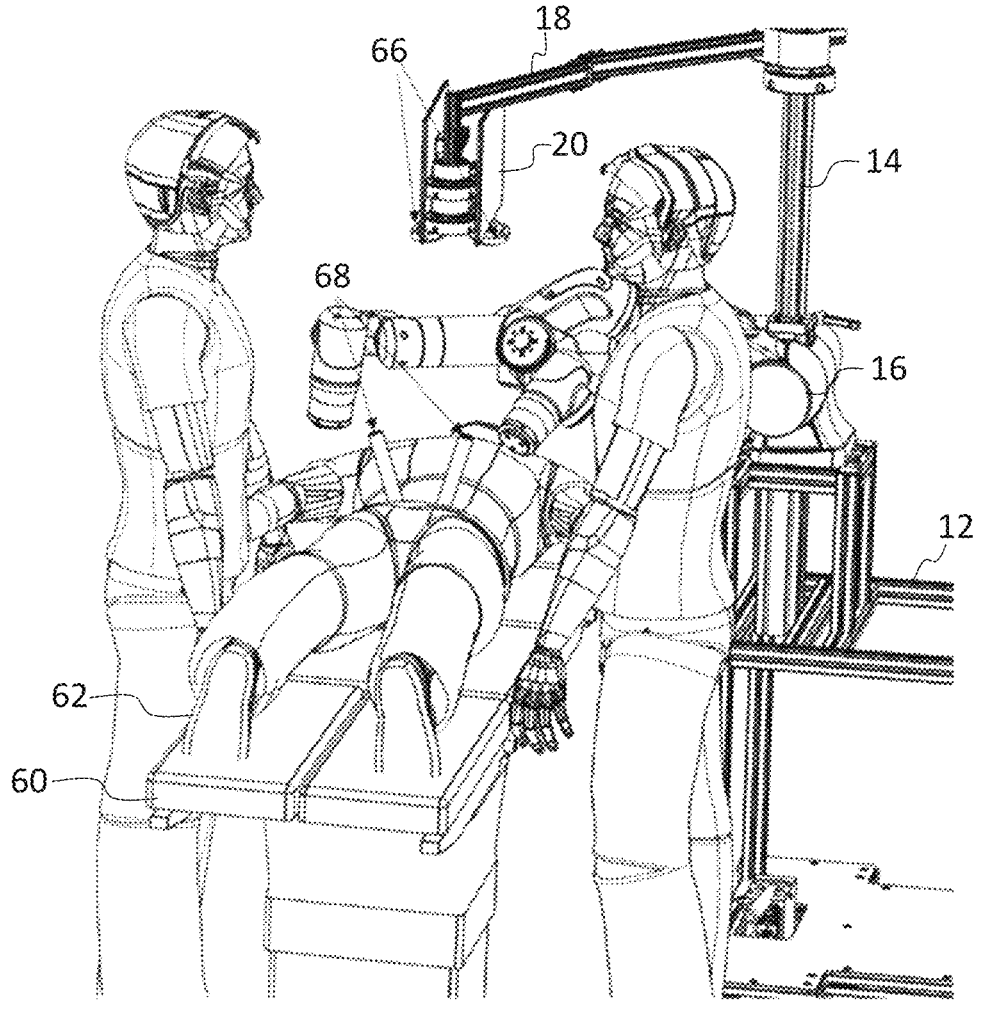
FIG. 30 shows one example of a dual configuration for two surgeons working simultaneously under microscope mode.

With further emphasis on FIG. 29, one or more ports 94 may be attached to the patient 62. The port 94 may include a small tube-like device inserted into the patient 62 to provide direct access to the surgical site. The port 94 may allow surgical instruments to be inserted and maneuvered with precision during minimally invasive surgeries. For magnified embodiments, ports 94 may be customized with fiducial markings 96, such as graduated or incremental markings along the inside of the tube, which act as a reference scale allowing the system 10 and/or surgeon to accurately adjust the magnification on the camera 66. The fiducial markings 96 may assist in establishing camera focal length as well as using the motorized display arm 18 to maintain camera position in a changing field of view due to patient movement.

Microscope mode also lends itself to a dual configuration for two surgeons working simultaneously by duplicating the microscope functionality and leveraging the dual-displays 20. For example, in FIG. 30, the surgeons are located on opposite sides of the patient 62. The displays 20 are positioned in back-to-back mode. Dual microscopes 68 may be positioned on the patient 62 such that the magnified images are sent to the respective displays 20. In this manner, each surgeon has a surgeon-specific view on their display 20 and may activate their surgical arm 16 independently. This dual-user configuration enables concurrent work, increasing efficiency and decreasing surgical time for the patient 62.

Traditionally optical visualization under magnification requires a separate, standalone asset in the operating room and surgical field. With space at a premium, the ability to offer this capability integrated with system 10 without any additional equipment is a significant benefit. Coupling microscope mode functionality with intelligent monitors 20 facilitates automated visualization of magnified patient anatomy further reducing the mental load on the surgeon as they no longer need to manipulate a separate microscope in the surgical field to achieve their desired view.

Figure 31:
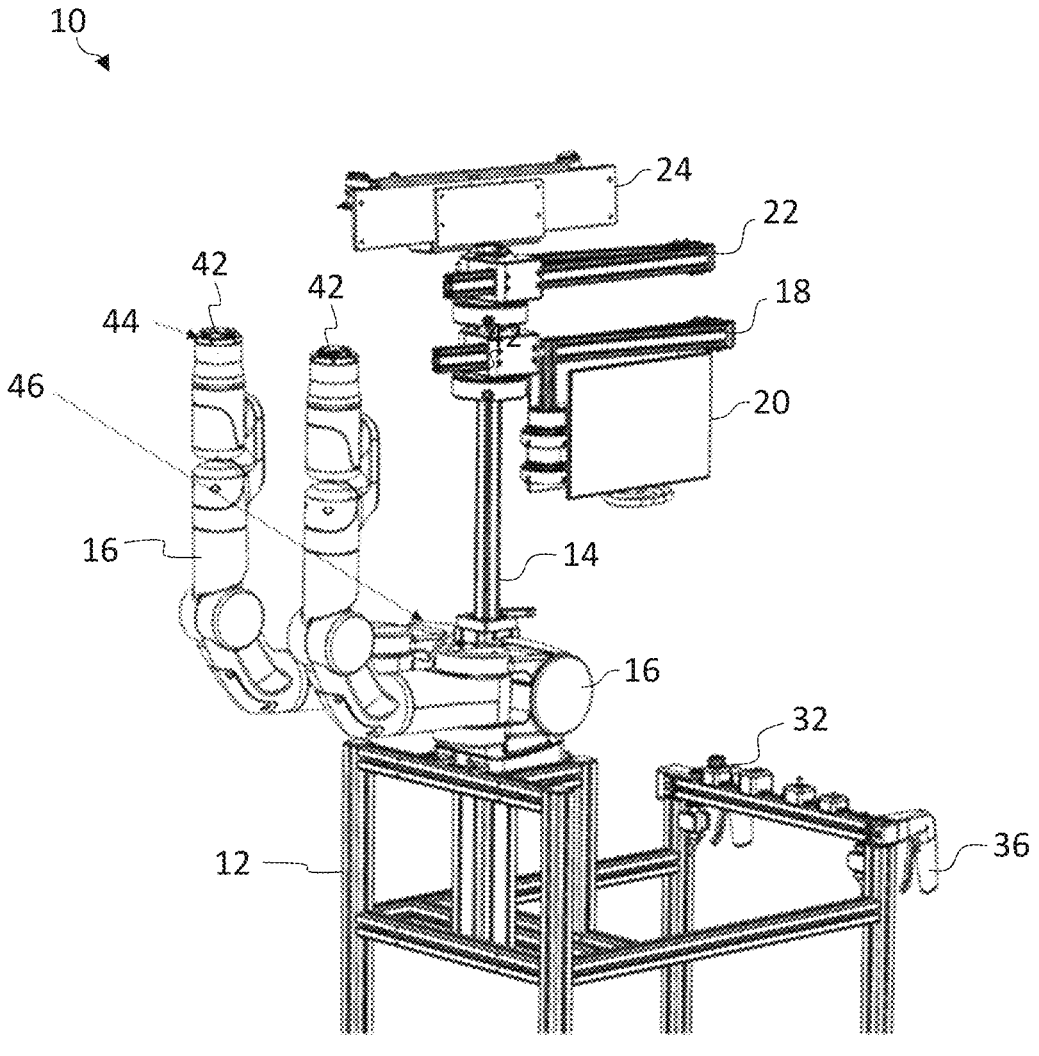
FIG. 31 shows the surgical robotic system with dual load cells at the base and end effector interface of each arm to detect and safely recover from collisions.

Turning now to FIG. 31, the integrated and coordinated robotic system 10 is configured for collision detection and avoidance. The operating room and surgical field are crowded spaces. Encoders may be integrated on not only the robotic arm joints but all moving parts of the deployed system 10. Combined with the known system geometry, it can be ensured that all automated system moves are accomplished without self-contact of different moving components of the system 10. Although not all potential sources of collision are within the system control, the system 10 is configured to detect and safely recover from collisions with external sources.

Each robot axis may have a motor to enable movement. Each motor may have a known and understood power profile to move each joint during different poses under normal operation. If power for movement rises above the expected value, it may be due to the robot encountering an obstruction, either human or inanimate. Although resistance to movement may be regularly encountered during procedural functions, such as bone removal, screw installation, and discectomy, an additional element may help to differentiate between collisions and clinical need for additional power.

In one embodiment, each surgical arm 16 includes a dual load cell configuration: a first six degree-of-freedom load cell 44 at the end effector mount point 42, which is configured to measure procedural loads and a second six degree-of-freedom load cell 46 at the base of the robot arm 16 to measure any load on the surgical arm 16. The duplex load cells 44, 46 may be able to isolate surgical loads from all other loads placed on the arm 16. Therefore, if motor power is above normal and non-surgical loads are detected, it can be inferred that the robot arm 16 is experiencing a collision and initiate safe-stop protocols. Due to the high refresh rate of the robotic kinematics solutions, the remediation actions may be accomplished at a speed to mitigate damage to both patient, staff, and equipment.

Collision detection and avoidance enables the safe, reliable, and predictable use of the surgical robotic platform 10. With the multitude of independently movable arms 16, 18, 22 and axes with susceptibility to unpredictable external inputs, while performing surgery on a patient 62, safety is paramount for both the patient 62 and all hospital staff participating in the procedure. These safety systems are also architected to be leveraged for additional performance gains during robot operation as well.

In accordance with some embodiments, coordinated movement of the robotic arms 16 may be achieved via a layout manager algorithm. In traditional graphical user interface (GUI) design, layout managers are employed to position UI elements based on relative constraints such as upper and lower bounds, alignment preferences, and inter-object spacing. This concept may also apply to the spatial coordination of robotic arms 16 in the surgical environment. With regard to functionality, each robotic arm will have its operational "space" defined relative to others and the surrounding environment, similar to a UI component in a graphical interface. Constraints may be set for each arm 16, taking into account the entire scene of the operating room, including other arms, surgical tools, the patient, and medical staff. These constraints may include distance bounds, alignment directives, and priority levels for movement and positioning. Regarding the algorithm, the robotic system 10 may employ a sophisticated algorithm akin to a layout manager. This algorithm may dynamically calculate the optimal position and trajectory for each arm 16, ensuring that movements are harmonious, non-colliding, and efficient, respecting the established constraints. It may adapt in real-time to changes in the operating environment, like moved equipment or adjusted surgical personnel positions. With regard to integration with existing systems, this coordinated movement may be integrated with existing collision detection and avoidance systems, enhancing overall spatial awareness and operational safety. The system 10 may utilize the encoded joint positions and the duplex load cells 44, 46 to gather real-time feedback on arm positions and exerted forces, ensuring precise and safe movements. By implementing relative positioning and movement constraints, the risk of collisions between arms 16 and with other objects in the surgical field is significantly reduced. The system 10 may optimize the positioning of each arm 16 for surgical tasks, improving procedural efficiency and reducing surgery time. The layout manager allows for easy adaptation to various surgical setups and procedures, making the system 10 highly versatile and scalable for different operating room environments.

In addition to the coordinated movement of robotic arms 16, integration of light detection and ranging (LIDAR) sensors on the motorized displays 20 may be provided to enhance collision avoidance capabilities in the surgical robot system 10. With regard to functionality, the LIDAR sensors may be equipped on the motorized displays 20 to continuously scan their immediate surroundings. This real-time spatial data may be fed into the system's scene modeling algorithms, allowing for a more comprehensive understanding of the operating room environment. The LIDAR sensor may allow for integration with scene modeling. The LIDAR data may complement existing navigation and camera-based systems, offering a more detailed and accurate environmental awareness. This enhanced scene modeling may help in avoiding collisions not only between the displays 20 and the robotic arms 16 but also with other elements in the surgical field such as medical staff, patient, and surgical tools. The algorithm enhancement may include collision avoidance algorithms, which may include the LIDAR input, enabling more precise and proactive adjustments to the positions of the motorized displays 20. This may ensure that the displays 20 maintain optimal positioning for surgical workflow while avoiding any potential collisions. The LIDAR sensors may provide a level of detail and accuracy in environmental sensing that complements camera-based systems, leading to a more robust collision avoidance capability. The integration of LIDAR into collision avoidance systems ensures a safer operating environment by reducing the risk of unintended contact between displays 20 and other elements in the operating room. The use of LIDAR may contribute to the reliable functioning of the robotic system 10, especially in complex and dynamically changing surgical environments.

Alternative Camera and Display Configurations

Figures 32A, 32B:
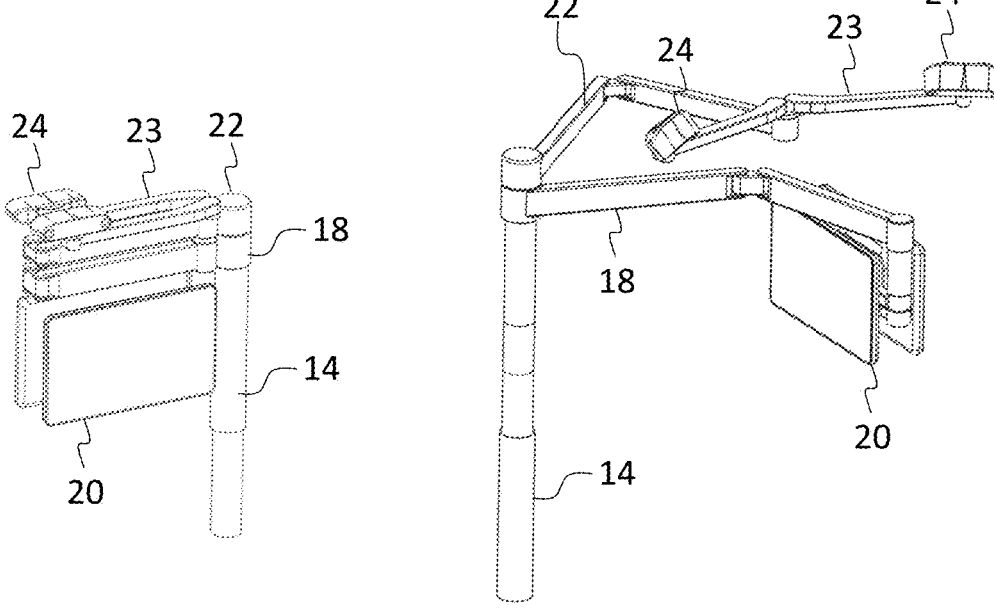
FIGS. 32A-32B show one example of two robotically controlled navigation cameras providing redundancy and reduced line of sight issues in docked and deployed configurations, respectively.

Turning now to FIGS. 32A-32B, the system 10 may include additional navigation cameras 24 to provide redundancy and further reduce line of sight issues. As shown in the deployed configuration shown in FIG. 32B, the camera arm 22 may include a bifurcated distal arm section 23 for supporting two separate navigational cameras 24. The bifurcated distal arm section 23 may include two arm segments attached at a revolute joint or other suitable joint. The split or bifurcation at the distal end of the camera arm 22 enables the cameras 24 to be positioned at different locations or angles, thereby reducing blind spots and improving the overall field of view. As shown in FIG. 32A, the system 10 may include a docked configuration where the arms 18, 22 are retracted and folded in on themselves to protect the cameras 24 and displays 20.

Figure 33A:
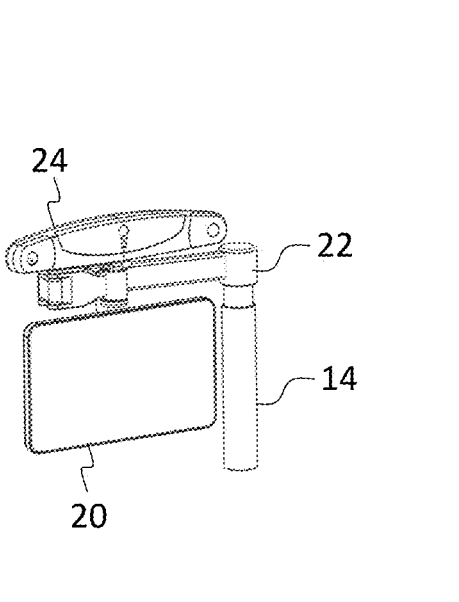
FIGS. 33A-33B show one example of a navigation camera and surgical display mounted to a selective compliance articulating robot arm (SCARA) in docked and deployed configurations, respectively.
Figure 33B:
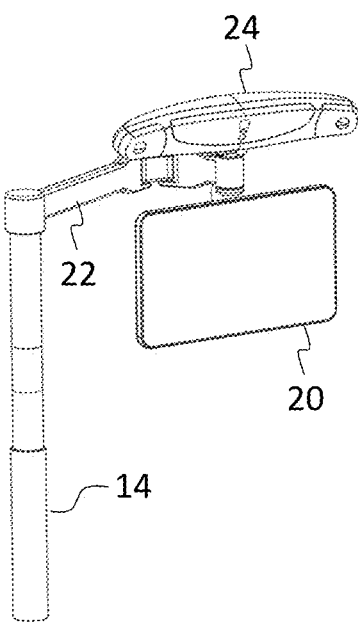

FIGS. 33A-33B show a simplified embodiment where the navigation camera 24 and display 20 share a single positioning arm 22. FIG. 33A shows the camera 24 and surgical display 20 in the docked position and FIG. 33B shows the camera 24 and display 20 in a deployed position. In this embodiment, the navigation camera 24 and surgical display 20 are mounted to a SCARA arm 14, 22. The navigation camera 24 may be located above the arm 22 and the display 20 may hang from beneath the arm 22. This configuration may simplify the system 10 and provide a more user-friendly system.

Surgical Arm Configurations

Turning now to FIGS. 34A-34B and 35-37, a configuration for each surgical arm 16 is shown according to one embodiment. Each surgical arm 16 may include a plurality of arm segments or links interconnected by numerous joints such that the arm 16 is configured to replicate the intricate motions of a human arm, hand, and/or fingers. Each joint may allow for specific types of movement or offer specialized motion. The surgical arm 16 described herein may include one or more of the following: (1) increased degrees of freedom and improved articulation; (2) improved accuracy by encoding the output of each joint and direct machine vision tracking of arm links; (3) enabling collaborative functionality with a faster motion control loop, closed-form kinematics, and haptic feedback; (4) force sensing along the length of the arm for surgeon control and collision detection; (5) improved power transfer to enable powered end effectors; (6) improved communication to enable bi-directional data communication between the end effector and robot for smart instruments; (7) removing the need for system homing which removes potential disruptions to the user, improving confidence and streamlining the workflow; and/or (8) enabling active movement of the arm with motor encoders enabling a safety architecture to the system, facilitating enhanced procedural impact, such as for milling. These improvements may enable the surgical robot to perform more parts of the procedure, creating more value for the surgeon.

Figure 35:
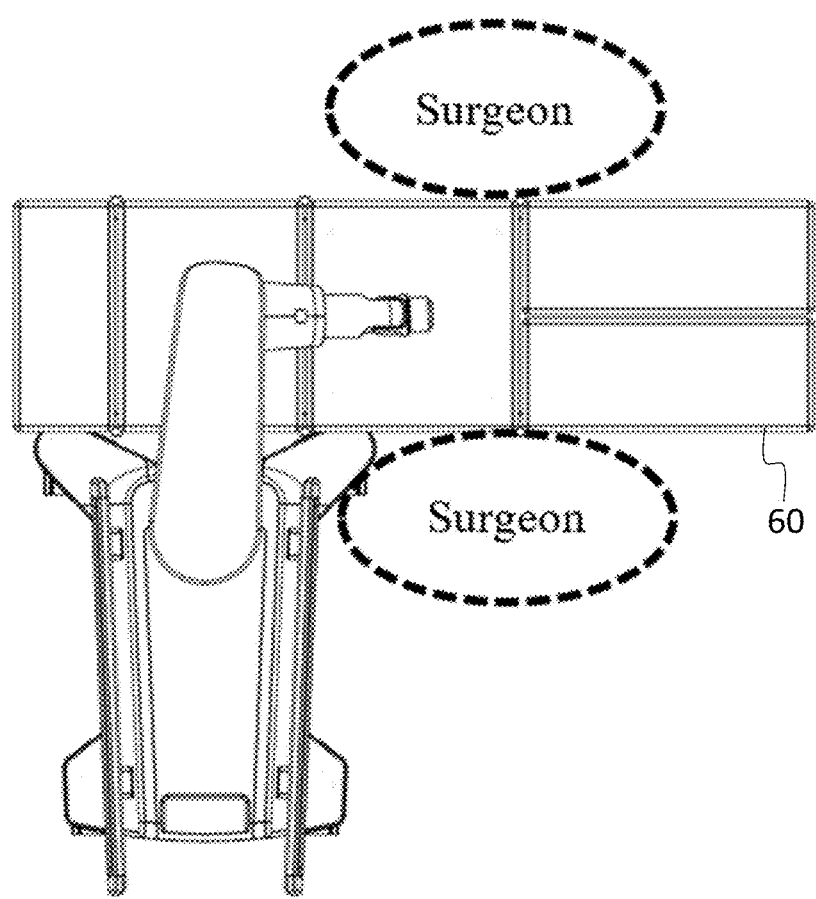
FIG. 35 shows a right angle pose at the operating room table for a surgical robot according to one embodiment.

Typical placement of a surgical robotic system, for example, tailored for orthopedic and neurosurgery procedures, may include positioning the system next to the OR table 60 with the robot arm in a right angle pose as shown in FIG. 35. This allows the surgeon to comfortably stand next to or across from the system without it impinging on their workspace. In addition, the motion and volume of the elbow is generally away from the surgical site. The configuration shown in FIG. 35 only provides five degrees of freedom (5 DoF) and is arranged in such a way that the inverse kinematics do not have a closed form solution. It may be preferred to have a minimum of 6 DoF to achieve a generalized trajectory in 3D space in any orientation. Systems that only have a 5 DoF arm relies on the user to set the 6th DoF, which is rotational position of the instrument in the guide tube. This may be effective in some procedures, particularly for instruments where rotational position control is not important, like drilling and driving screws. However, for a given, reachable trajectory, the 5 DOF system may only be able to achieve the trajectory in one or two specific poses. This limits the system's flexibility to work around other objects that may be in the surgical field, such as retractors, pedicle screw towers, reference arrays, etc.

Figure 34A:
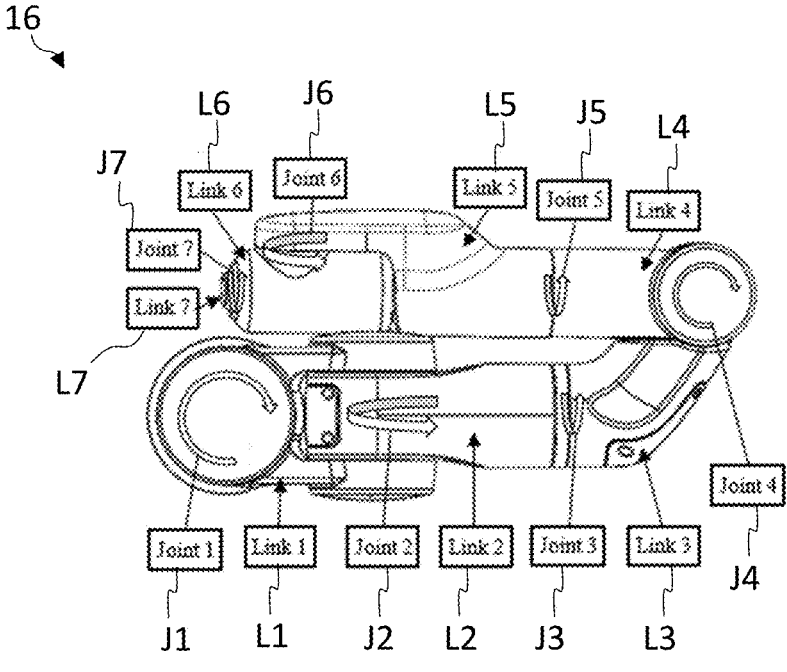
FIGS. 34A-34B show a closed-form inverse kinematic surgical arm configuration in docked and extended positions, respectively, according to one embodiment.
Figure 34B:
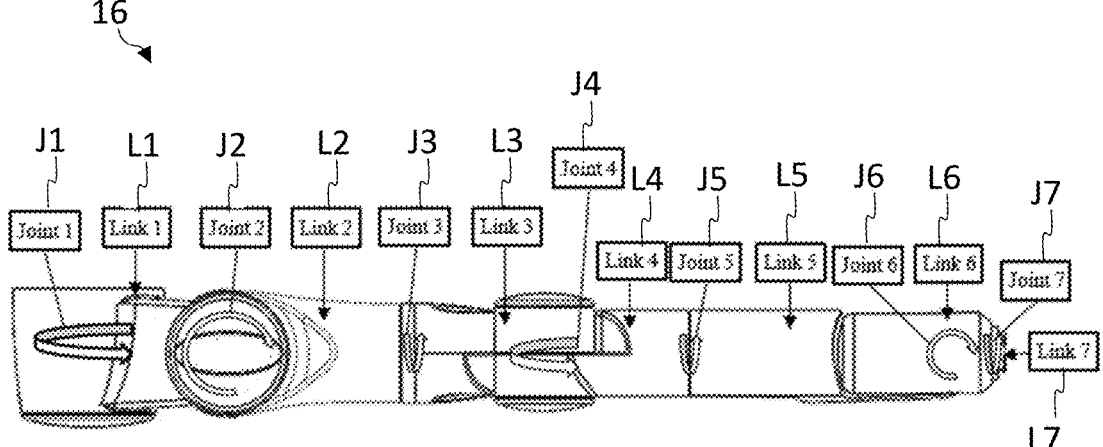

As shown in FIGS. 34A-34B, surgical arm 16 has seven degrees of freedom (7 DoF). The surgical arm 16 may include seven arm segments or links, starting from the base 12 or positioner 14 and ending at a free end at the end effector interface 42 including: first link L1, second link L2, third link L3, fourth link L4, fifth link L5, sixth link L6, and seventh link L7. The seven links may be interconnected via seven joints including: first joint J1, second joint J2, third joint J3, fourth joint J4, fifth joint J5, sixth joint J6, and seventh joint J7. Surgical arm 16 may have seven degrees of freedom (7 DoF) consisting exclusively of revolute joints, which each permit a singular axis of rotation. Each successive joint has an orthogonal rotation axis compared to the previous joint. The seven degrees of freedom provides a redundant axis for a general trajectory solution, and therefore enables a versatile solution space to solve a trajectory with numerous poses. In practice, this allows the user to manipulate the arm's pose, moving the links to provide more clearance where desired, while staying locked on a trajectory.

In FIG. 34A, the surgical arm 16 is shown in a docked position. In the docked position, the fifth, sixth, and seventh links (L5-L7) may align next to the first and second links (L1-L2). For example, the fifth, sixth, and seventh links (L5-L7) may align along an axis, which is generally parallel to an axis of first and second links (L1-L2). The compact docking position allows for the arms 16 to be folded close, for example, for storage or transport. FIG. 34B shows the surgical arm 16 in a deployed position. In this view, the arm 16 is fully extended. It will be appreciated, however, that the arm(s) 16 may be deployed such that the joints are bent and the arm segments are positioned or extended in any suitable manner for active participation in the surgical procedure.

Unlike other systems arranged in a way that the inverse kinematics do not have a closed form solution, surgical arm 16 has closed-form inverse kinematics. To achieve a single trajectory, the motion controller uses numerical methods to iteratively solve a system of equations until converging on a solution. The iterative calculations take time and can limit the speed of the motion control loop. For contrast, closed-form inverse kinematics enable the motion controller to calculate a trajectory by solving a system of equations once per trajectory. In closed-form solutions, the inverse kinematics problem is solved by deriving an exact analytical formula that provides the joint parameters (angles, distances) required to achieve the specified end effector position and orientation. With all else equal, removing the need for iterative calculations dramatically increases the control loop speed. This increase in control loop speed provides a weightless experience for users moving the arm via force input (pushing/pulling on the end effector or arm), and enables haptic user feedback.

Figure 36:
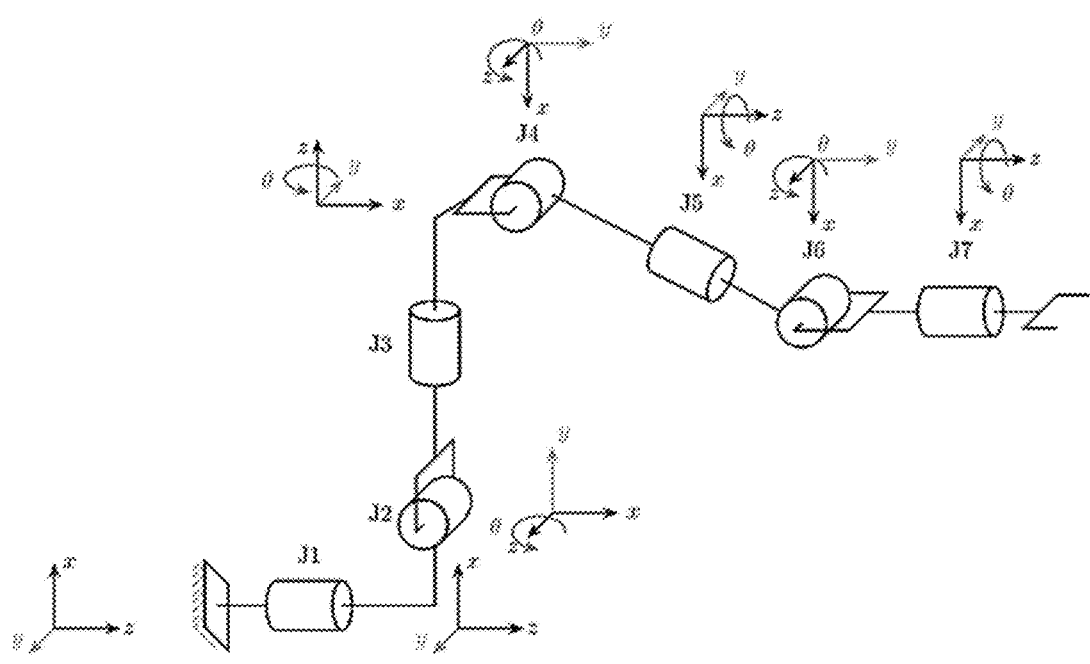
FIG. 36 shows a schematic representation of the joints of the surgical arm according to one embodiment.
Figure 37:
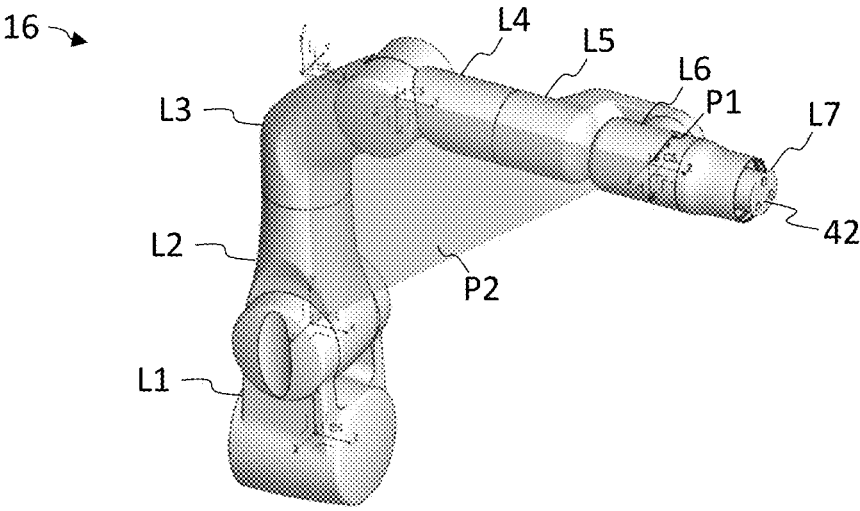
FIG. 37 shows the joint coordinate systems of the surgical arm according to one embodiment.

With reference to FIG. 36, a schematic representation of the joint arrangement is shown according to one embodiment. FIG. 37 shows the joint coordinate systems for surgical arm 16. The joint arrangement is configured to enable the following mathematical assumptions to be used in inverse kinematic calculations: (1) The axis of rotation for the fifth joint J5, sixth joint J6, & seventh joint J7 all intersect at a point P1 and are all orthogonal to their respective previous joint. As best seen in FIG. 37, the coincident origins for joints J5, J6, & J7 intersect at point P1, which allows the system to solve for this single intersection point P1, consolidating three unknowns down to one. (2) The coordinate system origins of second link through to seventh link (L2-L7) are all coplanar. As best seen in FIG. 37, the constant plane for J2-J7 origin, regardless of any joint orientation is plane P2 (depicted as a triangle). The angle of this plane P2 with respect to the ground is set by first joint J1. Again, this given information eliminates unknowns. In this manner, the position and orientation of the surgical arm 16 and end effector 26 are calculated directly from a given set of coordinates or desired pose, using explicit equations.

Figure 38A:
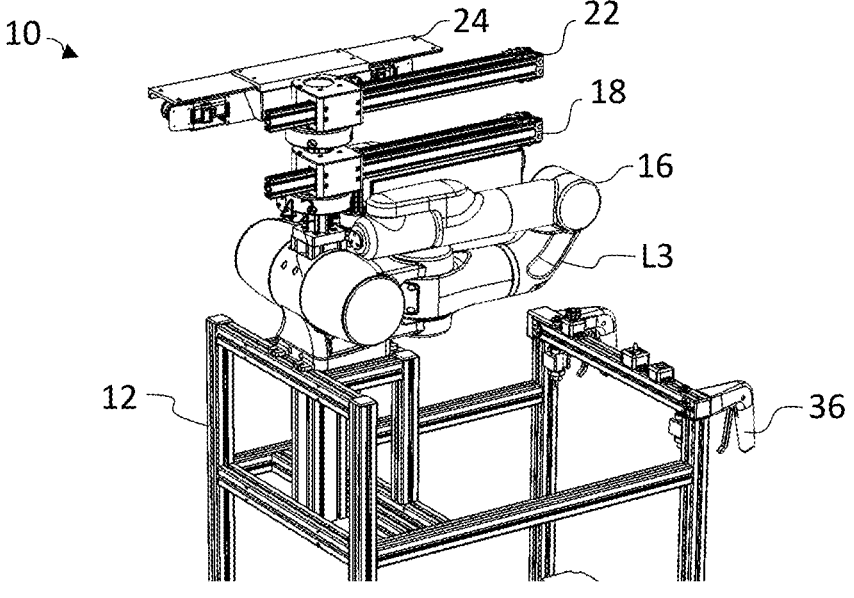
FIGS. 38A-38B show examples of optimized and inefficient docking, respectively, of the surgical arms.
Figure 38B:
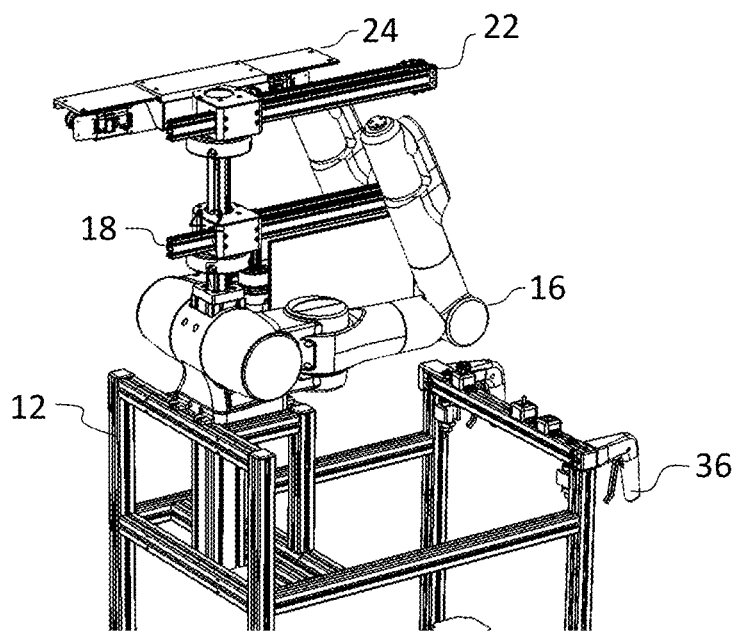

Turning now to FIGS. 38A-38B and 39A-39D, surgical arm(s) 16 are configured to have compact docking and occupy minimal volume while deployed in the surgical field. Compact docking is helpful for visibility while transporting the system 10 and during use in a low-profile, single arm mode, for example. Since two or more arms 16 may be deployed simultaneously, each surgical arm 16 is configured to occupy minimal volume in the surgical field. The docking and volume minimization requirements may be accomplished by an offset in the third link L3 of surgical arm 16. The offset of link L3 may include a bend or curve between the second and fourth links L2, L4. As best seen in FIG. 38A, the offset of link L3 allows the arm 16 to fold back on itself for compact docking. In contrast, FIG. 38B shows an inefficient storage volume when the arms 16 are docked with a straight third link L3. Thus, the offset of link L3 provides an efficient, streamlined, and compact storage solution for the surgical arms 16 when docked. The offset of link L3 is also configured such that the third joint J3 axis and fifth joint J5 axis remain co-planar. Remaining co-planar is important kinematically and to minimize the volume the arms 16 occupy while both are deployed.

Figures 39A, 39B, 39C, 39D:
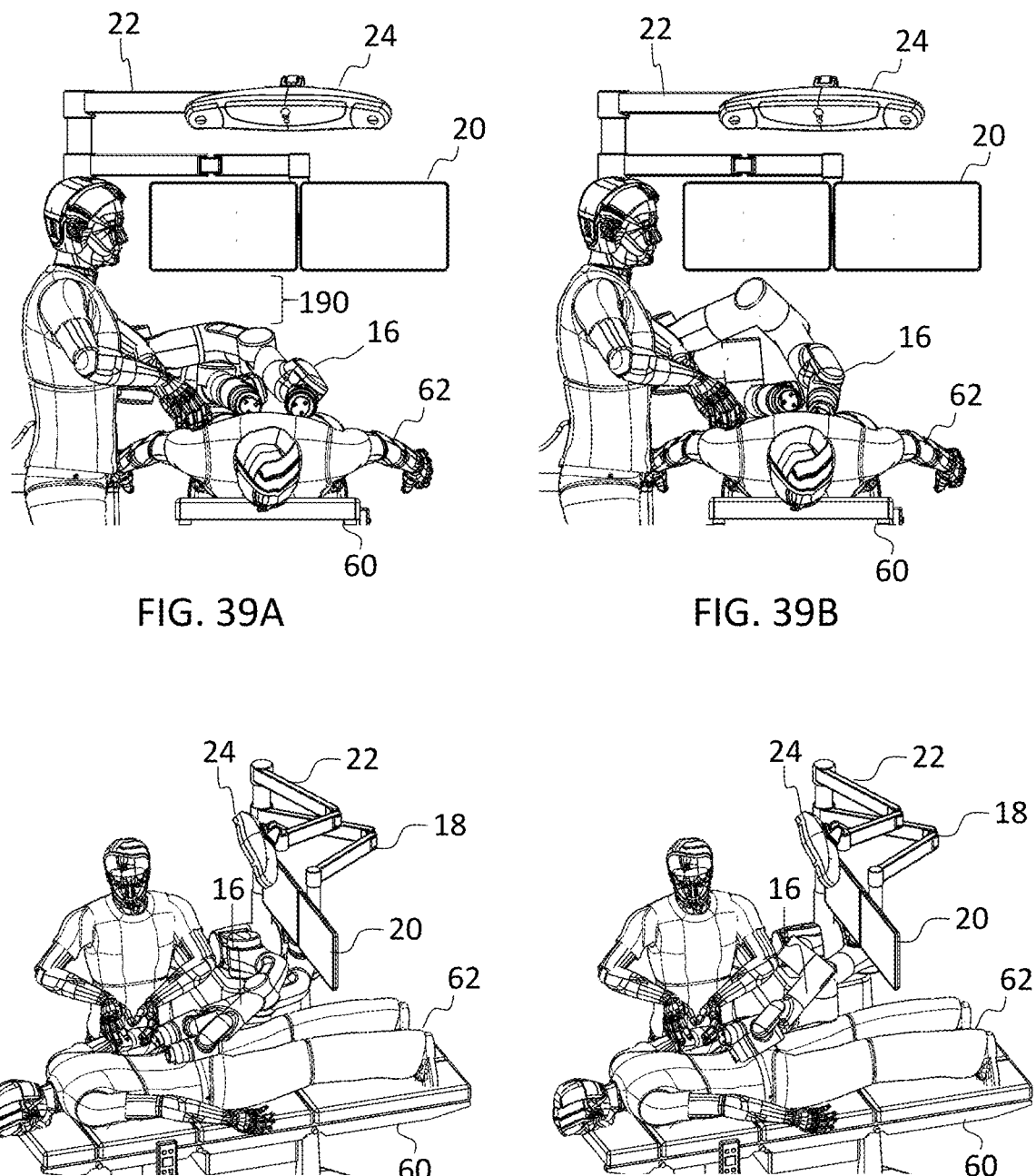
FIGS. 39A-39D show a comparison of right angle crossing pose for different surgical arm configurations.

As shown in FIGS. 39A-39D, an operative workflow with right angle arm crossing is compared for different configurations for link L3. As shown in FIGS. 39A and 39C, the offset of link L3 allows each surgical arm 16 to occupy minimal volume in the surgical space. As best seen in FIG. 39A, the surgical arms 16 claim a reduced space volume 190 when both arms 16 are deployed. In an alternative embodiment, the third joint J3 axis and fifth joint J5 axis may be offset to parallel planes to achieve an equally low-profile docked configuration. However, this causes the arms 16 to occupy roughly twice the volume when in the crossing, right angle pose as shown in FIGS. 39B and 39D. The operative workflow of positioning the robot system 10 in a right angle pose allows the system 10 to be positioned next to the OR table 60, while allowing the surgeon(s) to stand comfortably next to or across from the system 10, and without it impinging on their workspace. The surgical arms 16 are configured to take up minimal space within the surgical area to not overcrowd the operating environment and enhance visibility.

The arm joints and link geometry are arranged to minimize obstruction while deployed in the surgical field and to minimize the envelope volume while docked. The streamlined docking with both arms 16 allow one arm 16 to remain docked and not be obstructive if the procedure only requires one arm 16 to be deployed. The additional degrees of freedom increases the reachability of the robotic arms 16 to facilitate more procedures. The joint configuration also enables the closed loop kinematic solution, which increases the control loop speed leading to better haptics and overall motion.

Turning now to FIGS. 40A-41B, each joint of the surgical arm 16 may be motorized enabling precise automated movements and adjustments of the surgical arm(s) 16. Backlash may influence the controllability of the arm(s). Backlash in motion systems, sometimes called play, may be seen when an axis reverses direction (i.e., changing rotating from clockwise to counterclockwise) and may be defined as the magnitude of input motion required before the output also changes direction. Backlash is typically caused by clearance in a drive train, a classic example being the clearance between spur gear teeth. The clearance allows for gear assembly and allows for free-running motion, but it also introduces play into the system. When the drive gear changes direction, the drive tooth must travel through the clearance zone before the output gear changes direction in turn. While in this clearance window, the system is unable to correct output position, which contributes to positional error and generally decreases accuracy of the arm. Accordingly, surgical arms 16 may be configured with zero backlash to offer precise control and movement accuracy. Zero-backlash may be achieved by using a direct drive input to gearboxes specifically designed to have zero backlash (e.g., cycloidal or strain wave). The direct drive arrangement may ensure that no backlash is introduced from coupling to the motor, as contrasted with a spur, miter, or planetary gear input.

The joints may use frameless motors, meaning that the motor stator (windings) is integrated directly into the link housing, saving volume when compared to motors with self-contained frames. The motor rotor may be attached to a hollow shaft. The gearboxes may also have a through hole, providing a pathway to pass cables and rigid member to be discussed in following sections. Collectively, zero backlash will improve the accuracy of the arm and therefore improve the accuracy of the overall robotic system.

Each joint may use an absolute encoder on the load (output of the gearbox) to directly measure joint position, and an absolute encoder on the motor for commutation feedback. The encoder converts mechanical motion into an electrical signal to determine position, speed, or direction, thereby accurately reflecting the movement of the connected load and providing feedback for controlling the system. Using an absolute encoder on the load ensures that the system knows absolute joint position on power-up or after losing power, eliminating the need to perform a homing routine. This is particularly important to seamlessly resume a procedure in the event of an intermittent power loss. This feature also improves efficiency with which the system can be setup and deployed in a procedure. The encoder on the load also ensures that torsional flex in the gearboxes can be actively compensated, since the joint position after and including any flex is directly measured.

Figure 40A:
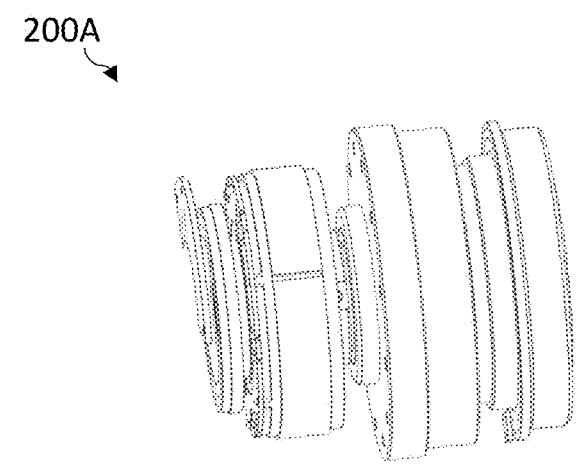
FIGS. 40A-40B show a load encoder at the output of the gearbox according to one embodiment.
Figure 40B:
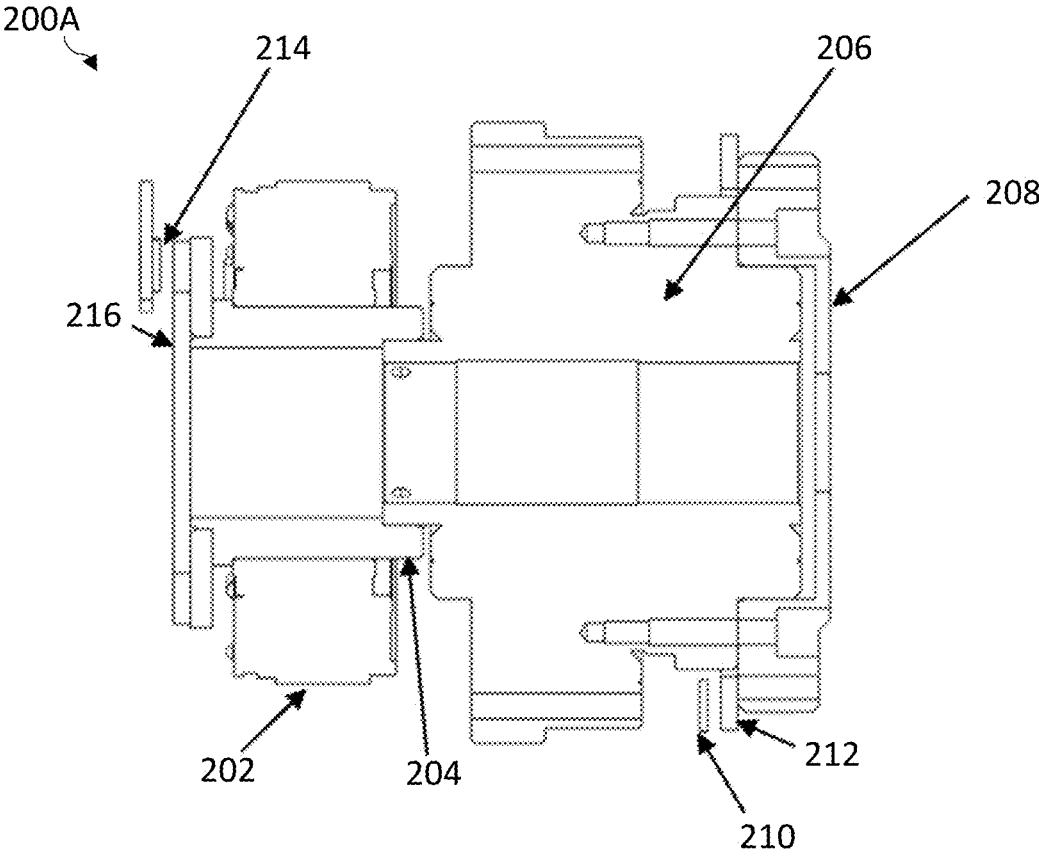
Figure 41A:
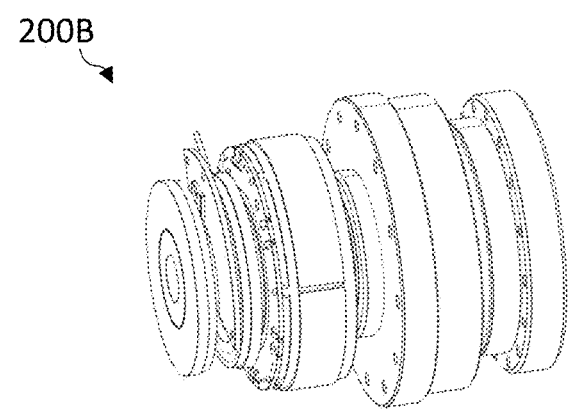
FIGS. 41A-41B show a load encoder before the motor according to one embodiment.
Figure 41B:
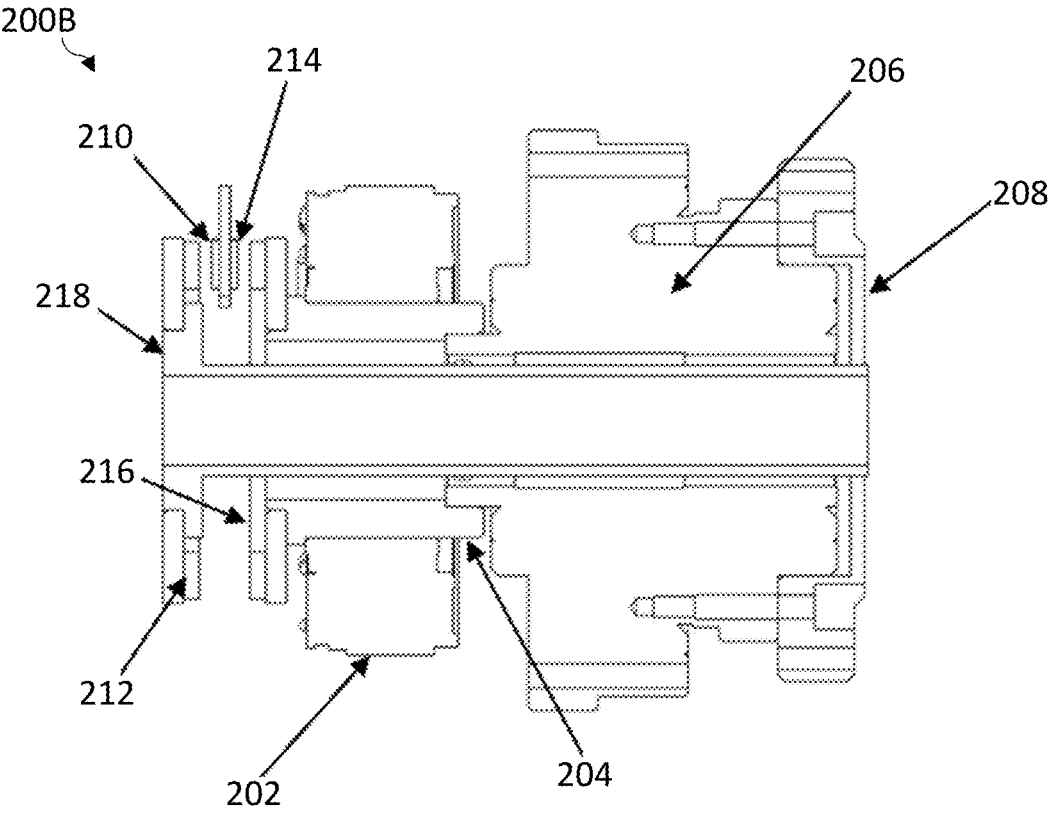

The load encoder may be located at the joint interface, directly measuring the output of the gearbox. Alternatively, the output of the gearbox can be extended back through the bore of the actuator, and measured inside the body of the previous link. The arrangement can save space and give the opportunity to collocate the encoder with the motor encoder. FIGS. 40A-40B show an example of a load encoder system 200A with the load encoder at the output of the gearbox, and FIGS. 41A-41B show an example of a load encoder system 200B before the motor via an extension through the bore.

The encoder systems 200A, 200B may include a motor 202 having a motor shaft 204, which acts as the primary source of mechanical power, a gearbox 206 attached to the motor 202, and an output plate 208, which applies the load. The encoder may be mounted before the gearbox 206 (e.g., on the motor shaft 204) or after the gearbox 206 (e.g., on the load side). In FIGS. 40A-40B, a load encoder sensor 210 for measuring the rotational position, speed, or direction of the load and a load encoder scale 212 for quantifying the load are mounted on the load side of the system 200A. In FIGS. 41A-41B, the load encoder sensor 210 and load encoder scale 212 are attached to the output extension 218, which extends from the output plate 208.

The systems 200A, 200B may also include a motor encoder to provide commutation feedback and accurate control of the motor 202. For example, a motor encoder sensor 214 and a motor encoder scale 216 may be attached to the motor 202. Using an absolute encoder on the motor 202, supports a safety architecture that can achieve a Safety Integrity Level of 3 (SIL 3), enabling active motion in the patient space.

Incorporating zero-backlash harmonic gearboxes into the robotic arm 16 yields greater positional accuracy and minimizes noise during motion. This may be beneficial for surgeons when performing delicate procedures so that they are more confident in the placement of tools and are not distracted or discouraged by the overwhelming sound of motors at work. The use of absolute encoders with each motor allow the arm position to be known without requiring an extra step to home the robot. This saves time during surgery preparation and prevents collisions, especially when both arms 16 are active in the field. Using motors with a prevailing torque instead of brakes reduces system heat generation and energy consumption.

Figure 42:
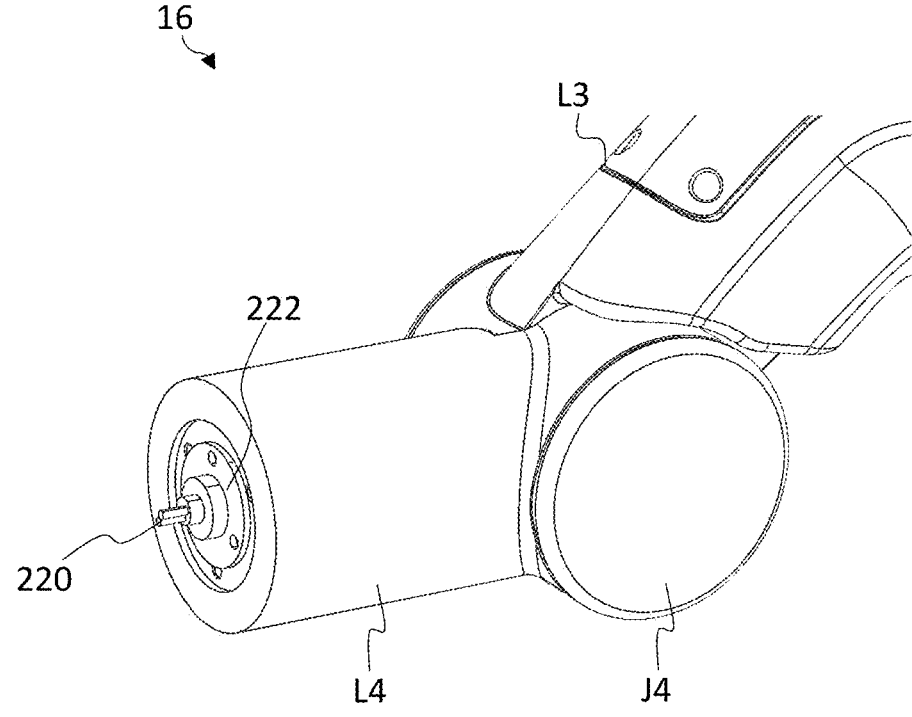
FIG. 42 shows a cable management system including a slip ring through the roll joint of the surgical arm according to one embodiment.

Turning now to FIG. 42, the surgical arm 16 may be configured for cable management. In particular, all arm wires or cables 220 may be routed internally through the arm joints. This avoids externally routed cables entrapping or pulling on drapes and objects while the arm 16 moves through its highly articulated range of motion. The challenge is then to ensure that the internal cables are not damaged from relative motions within the restricted arm volume, for example, from shearing, abrading, fatiguing, pulling, or otherwise. In one embodiment, miniature slip rings 222 are provided at each joint to pass cables 220 through rotating axes. The slip rings 222 may run through the central gearbox and motor bores. When the slip ring stator and rotor are affixed to the joint input and output respectively, relative motion is eliminated and the cable routing becomes effectively static. This eliminates cable wind-up and provides a theoretically infinite rotational range of motion for joints where the link bodies do not collide with one another (e.g., roll joints J1, J3, J5, & J7). Requiring all cabling 220 to be internal to the robotic system 10 makes the draping process more efficient and simpler as well as reduces possible field obstructions. The use of slip rings 222 decreases cable abrasion at the arm joints, which may increase their lifespan past what is expected of external cables or cables withstanding repeated twisting and bending. Overall, internally channeling the cables 220 through the arm 16 enhances the efficiency, safety, and functionality of the system 10.

As described previously with reference to FIG. 31, the surgical arm 16 integrates a 6-axis load cell 44 at the distal end of the arm 16, which is used to measure force inputs from the user and converts the forces to move commands. The load cell 44 may also be used to measure forces applied to the patient to monitor skiving, and generally ensure that there are no unsafe forces applied to the patient. In addition to the distal load cell 44, the arm 16 integrates a proximal load cell 46 at the base of each arm 16, before joint J1. The proximal load cell 46 is configured to monitor external forces on the arm 16, distinct from external forces on the end effector 26. External forces on the arm 16 are isolated from forces on the end effector 23 by subtracting the distal load cell measurements from the proximal load cell measurements. The system may also factor in the kinematic pose, arm geometry, and weight distribution and subtract the corresponding expected measurement from the actual load cell reading. This net reading may be used to back-calculate the resultant force/torque vector and the location it must be applied along the arm 16 to give the net measurement. With this information, the system may move the arm 16 to follow the force vector, letting the user push or pull anywhere on the arm 16 and change the pose while staying locked on trajectory. It can also be used as a collision detection function with automated safety features to move away from collisions with the patient or other objects in the field.

Utilizing dual 6 degree-of-freedom load cells 44, 46 allows the system 10 to calculate the delta force acting on the arm 16. By being able to differentiate between procedural loads and arm loads, the robotic system 10 is able to react to unexpected obstacles and collisions. For instance, if the force a surgeon applies to a tool in the field is acceptable, the system 10 may produce an error or disable movement if it is pushing against an obstacle in the field during trajectory movement. This feature also enables the system 10 to be collaborative such that the user can manually adjust positions of the arm 16 in addition to automated robotic movement of the arms 16.

Brakes on a surgical robot serve as safety and control mechanisms, ensuring stability and precision during surgical procedures. In one embodiment, the system 10 may not use discrete electromechanical brakes. In particular, the surgical arm(s) 16 may not have electromagnets to apply or release mechanical resistance (friction) to the joints. This minimizes arm volume and conserves power by not needing to constantly power the electromagnet holding the brakes open while the arms 16 move. Nonetheless, braking may be needed while the system 10 is unpowered, in active use or active servo mode, and during an E-stop condition.

Instead of using brakes in the static condition, the system 10 may take advantage of friction inherent to high reduction ratio gearboxes 206. The friction is enough to support the self-weight of the arm 16 in an unpowered state, meaning that the arm 16 holds its static pose, even without power. In the case where the system 10 needs a higher static holding force than the gearbox 206 can provide, the joint(s) may be augmented with a prevailing torque mechanism. The additional torque may be incrementally increased until the desired holding force is achieved. The tradeoff is that the motor 202 must be powerful enough to constantly drive through this additional torque. Some examples of prevailing torque augmentations may include a spring-loaded clutch plate, a compression fit nylon or bronze sleeve, radial nylon-tipped set screws, and/or a friction hinge in-line with gearbox output.

During active use or under active servo mode, precise positioning of the surgical arm(s) 16 may be achieved through active control. While under power, the primary operation mode is to actively servo-in-place such that the servo motors 202 actively control and maintain the position of the arm(s) 16. The servo motors 202 are capable of precise position control due to feedback mechanisms (e.g., from the encoders) that constantly monitor and adjust the motor's position. In this active mode, the motor power holds position, rather than brake power. If a joint is ever back driven, the feedback systems recognize this movement, and the arm(s) 16 correct their respective positions.

During an emergency stop or E-stop condition, power to the motors 202 is cut off in the event of an emergency. If a surgical arm 16 is moving while the E-stop is engaged, the arm 16 needs to halt motion within a safe stopping distance. Since the motor power is cut, this must be done without servo control. The friction in the gearboxes alone is not enough to accomplish this safe stopping distance while the arm 16 has momentum. To achieve the safe stopping distance on E-stop, the motor phases are shorted together, electromechanically locking the rotor and the stator together. This occurs because when the phases are unpowered and shorted together, any arm motion induces an electrical current and corresponding magnetic field which opposes the original motion. The more motion, the higher the restoring force, creating a motion stop with fast response time. By utilizing a robotic arm 16 that does not use discrete electromechanical brakes, the arm volume may be minimize and power can be conserved. A minimal arm volume helps to ensure that the user's direct line of sight is not obstructed and also reduces the occurrence of potential collisions.

Figure 43:
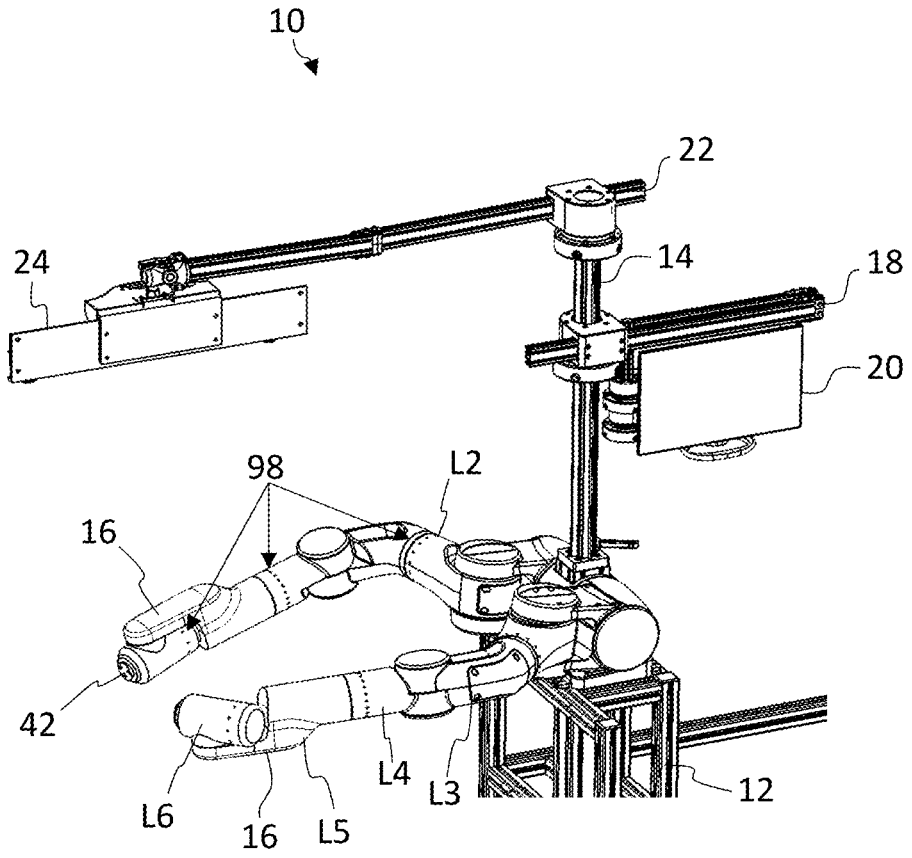
FIG. 43 shows an embodiment of machined fiducials for gross arm tracking.

Turning now to FIG. 43, the surgical arm(s) 16 may be directly tracked by the navigation system, for example, as a redundancy and safety mechanism in addition to tracking the end effector 26. For example, one or more tracking elements or markers 98 may be incorporated into the robotic arms 16 to support gross tracking. The tracking markers 98 may be provided on one or more individual arm links L1-L7. In the embodiment shown, the tracking markers 98 may be provided on links L2, L4, and L6, respectively. The tracking markers 98 may include machined fiducials, reflective discs, reflective spheres, and/or active LEDs that are all visible through a sterile drape with machine vision. In one embodiment, a ring of machined fiducials may be provided around the periphery of a given arm link (e.g., links L2, L4, & L6) to aid in accurate and reliable positioning of the arm(s) 16. Fine tracking elements may also be incorporated into the end effector 26 and tools 28 outside of the drape.

By tracking the individual arm links (e.g., one or more of links L1-L7) in addition to the end effector 26, the system 10 can continue navigating for a period of time if the end effector 26 is occluded. In such cases, the system 10 relies on kinematics from the distal most, tracked link, bridging the navigation gap until the end effector 26 is in line of sight again and can be directly tracked. This greatly improves the workflow of the system 10 as it reduces the disruptions of navigation loss and allows the user to proceed during a case seamlessly. Gross arm tracking may help to improve tracking accuracy as there is more positional data collected via machine vision than only from the end effector or tool array. This additional positional information streamlines the workflow and may result in less disruptions during the procedure as the system can continue movement even if there are small obstructions in the line of sight during procedures.

Figure 44A:
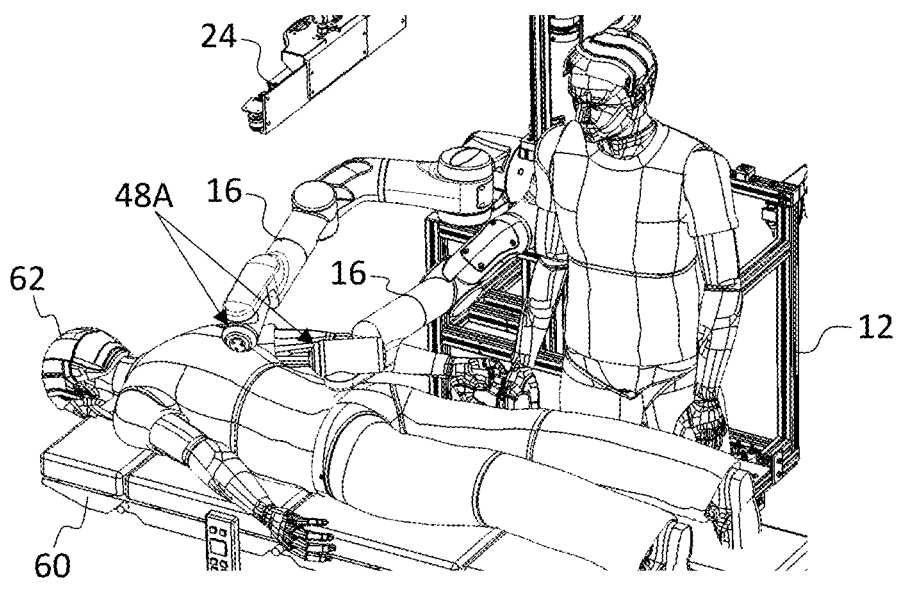
FIGS. 44A-44B show examples of rings of information positioned on the surgical arms and/or end effector to visually communicate status information for each respective arm.
Figure 44B:
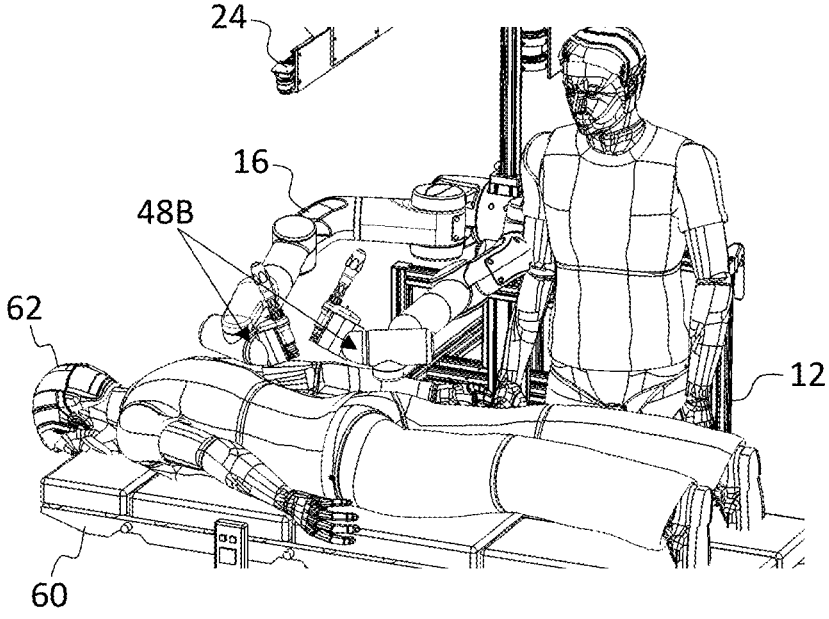

Turning now to FIGS. 44A-44B, rings of information (ROI) 48 may be integrated into the robotic platform 10 to visually communicate arm status to users. The rings of information 48 may be used to display active/not active arm status in cases of dual arm use. Other states may include off, boot up, servo, moving, in position, error, user force input mode, and trajectory mode. These states may be communicated through color (e.g., green, red, yellow, blue, etc.) and brightness sequences (e.g., off, on, blink, pulse, comet, etc.). The rings of information 48 may also communicate active and passive modes. As shown in FIG. 44A, one ring of information 48A may be located toward the distal end of each surgical arm 16 to ensure they are in the line of sight of the surgeon(s) during use. Alternatively, as shown in FIG. 44B, the rings of information 48B may be integrated into the end effector 26. This location is ideal for states of efficient use, which may be effectively communicated in direct line of sight of the surgeon(s) outside of the drape. The arm state communication provides visual cues to the user(s), which indicate the status of each surgical arm 16, thereby enhancing operational safety and efficiency by allowing the user to quickly assess the system's state and respond appropriately.

Displaying arm status clearly and noticeably allows for safe and efficient use of the robotic platform 10. It gives the user actionable information and reduces the unknown when using computer-assisted technology. Introducing the second arm 16 into the configuration also creates new status cases such as arm active/not active and having clear differentiation between the arms 16, for example, when using two player mode. Clear status communication helps the surgeons and OR staff to efficiently use and monitor the system.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference in its entirety, as if each such patent or publication were individually incorporated by reference herein. Various features and advantages of the invention are set forth in the following claims.

What is claimed is:

1. An active fixation method of a surgical robotic system having a moveable base station, including an on-board computer, a navigation camera mounted to the base station with a camera arm, a display mounted to the base station with a display arm, and a pair of surgical arms mounted to the base station, each surgical arm having an end effector, the method comprising:

identifying a first portion of bone, attaching the end effector of a first surgical arm to a first identified location, and leaving the first surgical arm rigidly attached to the first identified location; and identifying a second portion of bone, attaching the end effector of a second surgical arm to a second identified location while the first surgical arm remains rigidly attached to the first identified location, and once attached, removing the first surgical arm while leaving the second surgical arm rigidly attached to the second identified location, wherein at least one of the first and second surgical arms remain attached to bone at all times to act as a navigation source for enhanced navigation of the surgical robotic system.

2. The method of claim 1, wherein the bone is one or more vertebrae.

3. The method of claim 1, wherein the first identified location is a vertebral osteophyte.

4. The method of claim 3, wherein after the second surgical arm is rigidly attached to the second identified location, the osteophyte is removed with the first surgical arm.

5. The method of claim 1, wherein the first identified location is a facet.

6. The method of claim 5, wherein after the second surgical arm is rigidly attached to the second identified location, the facet is removed with the first surgical arm.

7. The method of claim 1, wherein the first identified location is a lamina.

8. The method of claim 7, wherein after the second surgical arm is rigidly attached to the second identified location, the lamina is removed with the first surgical arm.

9. The method of claim 1, wherein the first or second identified location is a pedicle.

10. The method of claim 1, further comprising sequentially performing a procedure while always leaving one surgical arm rigidly affixed to the last location, thereby enhancing navigation.

11. An active fixation method of a surgical robotic system having a moveable base station, including an on-board computer, a navigation camera mounted to the base station with a camera arm, a display mounted to the base station with a display arm, and a pair of surgical arms mounted to the base station, the method comprising:

guiding a first surgical arm of the surgical robotic system to a location on bone of a patient and attaching the first surgical arm to the location on the bone;

navigating a second surgical arm of the surgical robotic system based on the first attached surgical arm; and performing a surgical task while one surgical arm remains rigidly attached to the bone to act as a fixation anchor point for the bone and for providing spatial information about the location of the bone to the surgical robotic system, wherein the surgical task includes a decompression procedure.

12. The method of claim 11, wherein the first surgical arm is guided to a facet, and the second surgical arm navigates off the facet.

13. The method of claim 11, wherein the first surgical arm is guided to a lamina, and the second surgical arm navigates off the lamina.

14. The method of claim 11, wherein the first surgical arm is guided to an osteophyte, and the second surgical arm navigates off the osteophyte.

15. The method of claim 11, wherein the decompression procedure includes an osteotomy, laminectomy, or facetectomy.

16. An active fixation method of a surgical robotic system having a moveable base station, including an on-board computer, a navigation camera mounted to the base station with a camera arm, a display mounted to the base station with a display arm, and a pair of surgical arms mounted to the base station, each surgical arm having an end effector, the method comprising:

identifying an osteophyte, attaching the end effector of a first surgical arm to the osteophyte, and leaving the first surgical arm rigidly attached to the osteophyte;

navigating the end effector of a second surgical arm based on the first surgical arm while the first surgical arm remains rigidly attached to the osteophyte, and attaching the end effector of the second surgical arm to another location, and once attached, removing the first surgical arm while leaving the second surgical arm rigidly attached; and removing the osteophyte while leaving the second surgical arm rigidly attached to bone.

17. The method of claim 16, wherein the end effector includes a powered end effector for cutting bone.

18. The method of claim 16, wherein the osteophyte is a vertebral osteophyte.

19. The method of claim 16, wherein once the second surgical arm is rigidly attached, navigating the first surgical arm to the osteophyte, and then removing the osteophyte.

\* \* \* \* \*